United States Patent
Sauerberg et al.

(10) Patent No.: US 7,816,385 B2
(45) Date of Patent: Oct. 19, 2010

(54) DIMERIC DICARBOXYLIC ACID DERIVATIVES, THEIR PREPARATION AND USE

(75) Inventors: Per Sauerberg, Farum (DK); Lone Jeppesen, Virum (DK); Zdenek Polivka, Prague (CZ); Karel Sindelar, Prague (CZ)

(73) Assignee: High Point Pharmaceuticals, LLC, High Point, NC (US)

( * ) Notice: Subject to any disclaimer, the term of this patent is extended or adjusted under 35 U.S.C. 154(b) by 700 days.

(21) Appl. No.: 10/734,368

(22) Filed: Dec. 12, 2003

(65) Prior Publication Data

US 2004/0259950 A1    Dec. 23, 2004

Related U.S. Application Data

(60) Provisional application No. 60/439,410, filed on Jan. 10, 2003.

(30) Foreign Application Priority Data

Dec. 20, 2002    (DK) .................... 2002 01966

(51) Int. Cl.
| | |
|---|---|
| A61K 31/421 | (2006.01) |
| A61K 31/216 | (2006.01) |
| A61K 31/192 | (2006.01) |
| A61K 31/194 | (2006.01) |
| C07D 263/30 | (2006.01) |
| C07C 69/00 | (2006.01) |
| C07C 63/331 | (2006.01) |

(52) U.S. Cl. .................. 514/374; 514/533; 514/543; 514/557; 514/571; 548/235; 560/9; 560/59; 560/60; 560/81; 560/83; 562/469; 562/470; 562/488; 562/489

(58) Field of Classification Search ............ 562/469, 562/470, 488, 489, 492
See application file for complete search history.

(56) References Cited

U.S. PATENT DOCUMENTS

| | | | | |
|---|---|---|---|---|
| 4,148,915 | A | 4/1979 | Thuillier et al. | 424/308 |
| 5,063,240 | A | 11/1991 | Hindley | 514/369 |
| 5,306,726 | A | 4/1994 | Hulin | 514/375 |
| 6,028,088 | A * | 2/2000 | Pershadsingh et al. | 514/369 |
| 6,200,995 | B1 * | 3/2001 | De la Brouse-Elwood et al. | 514/347 |
| 7,507,832 | B2 * | 3/2009 | Mantlo et al. | 548/267.8 |
| 7,517,884 | B2 * | 4/2009 | Malecha et al. | 514/255.02 |
| 7,524,882 | B2 * | 4/2009 | Shi et al. | 514/469 |
| 7,528,160 | B2 * | 5/2009 | Conner et al. | 514/365 |
| 7,531,568 | B2 * | 5/2009 | Lin et al. | 514/414 |
| 7,538,135 | B2 * | 5/2009 | Vedananda | 514/407 |
| 7,544,702 | B2 * | 6/2009 | Bergeron et al. | 514/333 |
| 7,544,809 | B2 * | 6/2009 | Holla et al. | 548/235 |
| 7,544,812 | B2 * | 6/2009 | Gibson et al. | 548/319.1 |
| 7,544,835 | B2 * | 6/2009 | Matsuura et al. | 562/489 |
| 7,547,729 | B2 * | 6/2009 | Caumont-Bertrand et al. | 514/557 |
| 7,557,123 | B2 * | 7/2009 | Matsui et al. | 514/307 |
| 2002/0082263 | A1 * | 6/2002 | Lou et al. | 514/252.13 |
| 2002/0120137 | A1 * | 8/2002 | Houze et al. | 540/589 |
| 2002/0169185 | A1 * | 11/2002 | McGee et al. | 514/312 |
| 2003/0109579 | A1 * | 6/2003 | Sauerberg et al. | 514/533 |

FOREIGN PATENT DOCUMENTS

| | | |
|---|---|---|
| EP | 0 032 063 | 7/1981 |
| EP | 0 525 888 | 2/1993 |
| EP | 0597102 A1 | 5/1994 |
| EP | 0696585 B1 | 2/1996 |
| JP | 08/217766 | 8/1996 |
| JP | 09/291031 | 11/1997 |
| WO | WO 91/19702 A1 | 12/1991 |
| WO | WO 94/01420 A1 | 1/1994 |
| WO | WO 94/13650 A1 | 6/1994 |
| WO | WO 94/25448 A1 | 11/1994 |
| WO | WO 95/03038 A1 | 2/1995 |
| WO | WO 95/17394 A1 | 6/1995 |
| WO | WO 96/04260 A1 | 2/1996 |
| WO | WO 97/25042 A1 | 7/1997 |
| WO | WO 97/36579 A1 | 10/1997 |
| WO | WO 99/08501 A2 | 2/1999 |
| WO | WO 99/16758 A1 | 4/1999 |
| WO | WO 99/19313 A1 | 4/1999 |
| WO | WO 99/63983 A1 | 12/1999 |
| WO | 00/63153 | 10/2000 |
| WO | WO 01/00603 A1 | 1/2001 |
| WO | 01/79150 | 10/2001 |
| WO | 03/033453 | 4/2003 |
| WO | 03/053974 | 7/2003 |

OTHER PUBLICATIONS

Berger et al., The Journal of Biological Chemistry, vol. 274, No. 10, pp. 6718-6725 (Mar. 1999).
Leibowitz et al., FEBS Letters 473, pp. 333-336 (2000).
Muoio et al., The Journal of Biological Chemistry, vol. 277, No. 29, pp. 26089-26097 (Jul. 2002).
Oliver et al., PNAS, vol. 98, No. 9, pp. 5306-5311 (Apr. 2001).

* cited by examiner

Primary Examiner—Rosalynd Keys
(74) Attorney, Agent, or Firm—Robert S. Dailey

(57) ABSTRACT

A novel class of dicarboxylic acid derivatives, the use of these compounds as pharmaceutical compositions, pharmaceutical compositions comprising the compounds and methods of treatment employing these compounds and compositions. The present compounds may be useful in the treatment and/or prevention of conditions mediated by Peroxisome Proliferator -Activated Receptors (PPAR).

10 Claims, No Drawings

DIMERIC DICARBOXYLIC ACID DERIVATIVES, THEIR PREPARATION AND USE

CROSS-REFERENCE TO RELATED APPLICATIONS

This application claims priority under 35 U.S.C. 119 of Danish application no. PA 2002 01966 filed Dec. 20, 2002 and U.S. application Ser. No. 60/439,410 filed Jan. 10, 2003, the contents of which are fully incorporated herein by reference.

FIELD OF THE INVENTION

The present invention relates to novel dimeric dicarboxylic acid derivatives, to the use of these compounds as pharmaceutical compositions, to pharmaceutical compositions comprising the compounds and to a method of treatment employing these compounds and compositions. More specifically, the compounds of the invention can be utilised in the treatment and/or prevention of conditions mediated by the Peroxisome Proliferator-Activated Receptors (PPAR), in particular the PPARδ subtype.

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

PPARδ activation was initially reported not to be involved in modulation of glucose or triglyceride levels. (Berger et al., j. Biol. Chem., 1999, Vol 274, pp. 6718-6725). Later it has been shown that PPARδ activation leads to increased levels of HDL cholesterol in db/db mice (Leibowitz et al. FEBS letters 2000, 473, 333-336). Further, a PPARδ agonist when dosed to insulin-resistant middle-aged obese rhesus monkeys caused a dramitic dose-dependent rise in serum HDL cholesterol while lowering the levels of small dense LDL, fasting triglycerides and fasting insulin (Oliver et al. PNAS 2001, 98, 5306-5311) .The same paper also showed that PPARδ activation increased the reverse cholesterol transporter ATP-binding cassette A1 and induced apolipoprotein A1-specific cholesterol efflux. The involvement of PPARδ in fatty acid oxidation in muscles was further substantiated in PPARα knock-out mice. Muoio et al. (J. Biol. Chem. 2002, 277, 26089-26097) showed that the high levels of PPARδ in skeletal muscle can compensate for deficiency in PPARα. Taken together these observations suggest that PPARδ activation is useful in the treatment and prevention of cardiovascular diseases and conditions including atherosclerosis, hypertriglyceridemia, and mixed dyslipidaemia (WO 01/00603).

A number of compounds have been reported to be useful in the treatment of hyperglycemia, hyperlipidemia and hypercholesterolemia (U.S. Pat. No. 5,306,726, WO 91/19702, WO 95/03038, WO 96/04260, WO 94/13650, WO 94/01420, WO 97/36579, WO 97/25042, WO 95/17394, WO 99/08501, WO 99/19313, WO 99/16758 and WO 01/00603).

The following documents disclose various compounds with PPARγ activity: U.S. Pat. No. 5,063,240, EP 0597102, EP 0696585, WO 94/25448, JP 09291031, JP 08217766, WO 99/63983.

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

This indicate that research for compounds displaying various degree of PPARα, PPARγ and PPARδ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome i.e. impaired glucose tolerance, insulin resistance, hypertrigyceridaemia and/or obesity), cardiovascular diseases (including atherosclerosis) and hypercholesteremia.

Definitions

In the structural formulas given herein and throughout the present specification the following terms have the indicated meaning:

The terms "$C_{1-n'}$-alkyl" wherein n' can be from 2 through 6, as used herein, represent a linear or branched, saturated hydrocarbon chain having the indicated number of carbon atoms. Examples of such groups include, but are not limited to methyl, ethyl, n-propyl, isopropyl, butyl, isobutyl, sec-butyl, tert-butyl, pentyl, isopentyl, hexyl, isohexyl and the like.

The term "$C_{3-n'}$-cycloalkyl" wherein n' can be from 4 through 6, as used herein, alone or in combination, represent a saturated monocyclic hydrocarbon group having the indicated number of carbon atoms. Examples of such groups include, but are not limited to cyclopropyl, cyclobutyl, cyclopentyl, cyclohexyl and the like.

The terms "$C_{1-n'}$divalent saturated carbon chain" and "$C_{1-n'}$-alkylene" wherein n' can be from 2 through 6, as used herein, represent a divalent linear or branched, saturated hydrocarbon chain having the indicated number of carbon atoms. Examples of such groups include, but are not limited to methylene, ethylene, trimethylene, tetramethylene, propylene, ethylethylene, methylpropylene, ethylpropylene and the like.

The terms "$C_{4-n'}$-Cycloalkylene" wherein n' can be from 5 through 6, as used herein, represent a divalent saturated monocyclic hydrocarbon group having the indicated number of carbon atoms. Examples of such groups include, but are not limited to cyclopentylene, cyclohexylene and the like.

The term "$C_{2-n'}$-alkenyl" wherein n' can be from 3 through 6, as used herein, represent an olefinically unsaturated branched or straight hydrocarbon group having from 2 to the specified number of carbon atoms and at least one double bond. Examples of such groups include, but are not limited to, vinyl, 1-propenyl, 2-propenyl, allyl, iso-propenyl, 1,3-butadienyl, 1-butenyl, hexenyl, pentenyl and the like.

The term "$C_{2-n'}$-alkenylene" wherein n' can be from 3 through 6, as used herein, represent an divalent olefinically unsaturated branched or straight hydrocarbon group having from 2 to the specified number of carbon atoms and at least one double bond. Examples of such groups include, but are not limited to ethenylene (—CH═CH—), the propenylene isomers (e.g., —CH$_2$CH═CH— and —C(CH$_3$)═CH—), the butenylene isomers (e.g., —CH$_2$CH═C(CH$_3$)—and —CH$_2$CH$_2$CH═CH—) and the like.

The terms "$C_{4-n'}$-alkenynyl" as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like, especially preferred is 1-pentene-4-yne.

The term "$C_{4-n'}$-cycloalkenylene" wherein n' can be from 5 through 6, as used herein, represent an divalent unsaturated monocyclic hydrocarbon group having from 4 to the specified number of carbon atoms and at least one double bond. Examples of such groups include, but are not limited to cyclohexenylene and the like.

The term "$C_{3-n'}$-alkynyl" wherein n' can be from 4 through 6, as used herein, represent an unsaturated branched or straight hydrocarbon group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The term "$C_{2-n'}$-alkynylene" wherein n' can be from 3 through 6, as used herein, represent an divalent unsaturated branched or straight hydrocarbon group having from 2 to the specified number of carbon atoms and at least one triple bond. Examples of such groups include, but are not limited to, propynylene (—CH$_2$C≡C—), the butynylene isomers (e.g., —CH$_2$CH$_2$C≡C—, —CH$_2$C≡C—CH$_2$—), and the like.

The term "$C_{4-n'}$-alkenynylene" wherein n' can be from 5 through 9 as used herein, represent an divalent unsaturated branched or straight hydrocarbon group having from 4 to the specified number of carbon atoms and both at least one double bond and at least one triple bond. Examples of such groups include, but are not limited to, 1-penten-4-ynylene, 3-penten-1-ynylene, 1,3-hexadiene-5-ynylene and the like.

The term "$C_{3-n'}$-divalent unsaturated carbon chain" wherein n' can be from 4 through 9, as used herein, represent an divalent unsaturated branched or straight hydrocarbon group having from 3 to the specified number of carbon atoms and at least one double bound (alkenylen) or at least one triple bound (alkynylene) or a combination hereof (alkenynylene). Examples of such groups include, but are not limited to ethenylene (—CH═CH—), the propenylene isomers (e.g., —CH$_2$CH═CH— and —C(CH$_3$)═CH—), the butenylene isomers (e.g., —CH$_2$CH═C(CH$_3$)— and CH$_2$CH$_2$CH═CH—), propynylene (—CH$_2$C≡C—), the butynylene isomers (e.g., —CH$_2$CH$_2$C≡C—, —CH$_2$C≡C—CH$_2$—), 1-penten-4-ynylene, 3-penten-1-ynylene, 1,3-hexadiene-5-ynylene and the like.

The term "$C_{1-n'}$-alkoxy" wherein n' can be from 2 through 6, as used herein, alone or in combination, refers to a straight or branched configuration linked through an ether oxygen having its free valence bond from the ether oxygen. Examples of such linear alkoxy groups include, but are not limited to methoxy, ethoxy, propoxy, butoxy, pentoxy, hexoxy and the like. Examples of such branched alkoxy include, but are not limited to isopropoxy, sec-butoxy, tert-butoxy, isopentyloxy, isohexyloxy and the like.

The term "$C_{3-n'}$-Cycloalkoxy" wherein n' can be from 4 through 6, as used herein, alone or in combination, represent a saturated monocyclic hydrocarbon group having the indicated number of carbon atoms linked through an ether oxygen having its free valence bond from the ether oxygen. Examples of such cycloalkoxy groups include, but are not limited to cyclopropyloxy, cyclobutyloxy, cyclopentyloxy, cyclohexyloxy and the like.

The term "$C_{1-n'}$-alkylthio" wherein n' can be from 2 through 6, as used herein, alone or in combination, refers to a straight or branched monovalent substituent comprising a $C_{1-6}$-alkyl group linked through a divalent sulfur atom having its free valence bond from the sulfur atom and having 1 to 6 carbon atoms. Examples of such groups include, but are not limited to methylthio, ethylthio, propylthio, butylthio, pentylthio and the like.

The term "$C_{3-n'}$-cycloalkylthio" wherein n' can be from 4 through 6, as used herein, alone or in combination, represent a saturated monocyclic hydrocarbon group having the indicated number of carbon atoms linked through a divalent sulfur atom having its free valence bond from the sulfur atom. Examples of such cycloalkoxy groups include, but are not limited to cyclopropylthio, cyclobutylthio, cyclopentylthio, cyclohexylthio and the like.

The term "aryl" as used herein refers to an aromatic monocyclic or an aromatic fused bi- or tricyclic hydrocarbon group. Examples of such groups include, but are not limited to phenyl, naphthyl, anthracenyl, phenanthrenyl, azulenyl, fluorenyl and the like.

The term "arylene" as used herein refers to divalent aromatic monocyclic or a divalent aromatic fused bi- or tricyclic hydrocarbon group (derived from aryl). Examples of such groups include, but are not limited to phenylene, naphthylene, fluorenylene and the like.

The term "heteroaryl" as used herein, alone or in combination, refers to a divalent substituent comprising a 5-7 membered monocyclic aromatic system or a 8-10 membered bicyclic fused aromatic system containing one or more heteroatoms selected from nitrogen, oxygen and sulfur or a 10-16 membered tricyclic fused aromatic system containing one or more heteroatoms selected from nitrogen, oxygen and sulfur e.g. furyl, thienyl, pyrrolyl, imidazolyl, pyrazolyl, triazolyl, pyridyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinnyl, indolyl, benzimidazolyl, benzofuranyl, pteridinyl, purinyl, carbazolyl, β-carbolinyl, acridinyl, phenanthrolinyl, phenazinyl, phenoxazinyl, phenothiazinyl and the like The term "heteroarylene" as used herein, alone or in combination, refers to a divalent substituent (derived from heteroaryl) comprising a 5-7 membered monocyclic aromatic system or a 8-10 membered bicyclic aromatic system containing one or more heteroatoms selected from nitrogen, oxygen and sulfur or a 10-16 membered tricyclic fused aromatic system containing one or more heteroatoms selected from nitrogen, oxygen and sulfur e.g. furylene, thienylene, pyrrolylene, imidazolylene, pyrazolylene, triazolylene, pyrazinylene, pyrimidinylene, pyridazinylene, isothiazolylene, isoxazolylene, oxazolylene, oxadiazolylene, thiadiazolylene, quinolylene, isoquinolylene, quinazolinylene, quinoxalinnylene, indolylene, benzimidazolylene, benzofuranylene, pteridinylene, purinylene carbazolylene, β-carbolinylene, acridinylene, phenanthrolinylene, phenazinylene, phenoxazinylene, phenothiazinylene and the like.

The term "a divalent polycyclic ringsystem" as used herein refers to a divalent group formed from a polycyclic ringsystem containing indenpending of each other 2 trough 4 aryl or heteroaryl ring systems joined by single bonds. Example of such bi-, ter- and quaterarylylene having 2 through 4 identical aryl ring systems include, but are not limited to biphenylylene, binaphthylylene, terphenylylene, temaphthylylene, quaterphenylylene, quatemaphthylylene and the like. Example of such bi-, ter- and quaterheteroarylylene having 2 through 4 identical heteroaryl ring systems include, but are not limited to bipyridylylene, biindolylylene, terpyridylylene, terindolylylene, quaterpyridylylene, quaterindolylylene and the like. Example of such polycyclic ringsystems having non identical ring systems include, but are not limited to diphenylpyridine and the like.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "aralkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphthyl)ethyl and the like.

The term "halogen" means fluorine, chlorine, bromine or iodine.

The term "treatment" as used herein includes treatment, prevention and management of conditions mediated by Peroxisome Proliferator-Activated Receptors (PPAR).

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

DESCRIPTION OF THE INVENTION

The present invention relates to compounds of the general formula (I):

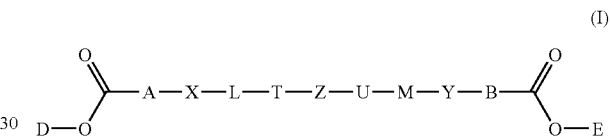

wherein A is $C_{1-3}$-alkylene which is optionally substituted with one or more substituents selected from
  halogen or
  $C_{1-3}$-alkyl, $C_{1-6}$alkoxy, $C_{3-6}$-cycloalkoxy, $C_{1-6}$alkylthio, $C_{3-6}$-cycloalkylthio or aralkoxy each of which is optionally substituted with one or more halogens; or
  $NR_1R_2$ wherein $R_1$ represents hydrogen or $C_{1-3}$-alkyl and $R_2$ represents —$R_3$—(C=O)—$R_4$ wherein:
    $R_3$ represents $C_{1-6}$alkylene, $C_{2-4}$-alkenylene, $C_{4-4}$-cycloalkylene, $C_{4-4}$-cycloalkenylene, or arylene optionally substituted with one or more halogens;
    $R_4$ represents aryl optionally substituted with one or more halogens; or
A is —O -A' or —S-A' wherein —O— or —S— is linked to X in formula (I) and wherein A' is $C_{1-3}$-alkylene which is optionally substituted with one or more substituents selected from
  halogen or
  $C_{1-3}$-alkyl, $C_{1-6}$-alkoxy, $C_{3-6}$-cycloalkoxy, $C_{1-6}$alkylthio, $C_{3-6}$-cycloalkylthio or aralkoxy each of which is optionally substituted with one or more halogens; or
  $NR_1R_2$ wherein $R_1$ represents hydrogen or $C_{1-3}$-alkyl and $R_2$ represents —$R_3$—(C=O)-$R_4$ wherein:
    $R_3$ represents $C_{1-6}$alkylene, $C_{2-6}$-alkenylene, $C_{4-6}$-cycloalkylene, $C_{4-6}$-cycloalkenylene, or arylene optionally substituted with one or more halogens;
    $R_4$ represents aryl optionally substituted with one or more halogens; and
B is $C_{1-3}$-alkylene which is optionally substituted with one or more substituents selected from
  halogen or
  $C_{1-3}$-alkyl, $C_{1-6}$alkoxy, $C_{3-6}$-cycloalkoxy, $C_{1-6}$-alkylthio, $C_{3-6}$-cycloalkylthio or aralkoxy each of which is optionally substituted with one or more halogens; or NR$_1$R$_2$ wherein R$_1$ represents hydrogen or C$_{1-3}$-alkyl and R$_2$ represents —R$_3$—(C=O)—R$_4$ wherein:
  R$_3$ represents C$_{1-6}$-alkylene, C$_{2-6}$-alkenylene, C$_{4-6}$-cycloalkylene, C$_{4-6}$-cycloalkenylene, or arylene optionally substituted with one or more halogens;
  R$_4$ represents aryl optionally substituted with one or more halogens; or
B is —O—B' or —S—B' wherein —O— or —S— is linked to Y in formula (I) and wherein B' is C$_{1-3}$-alkylene which is optionally substituted with one or more substituents selected from
  halogen or
  C$_{1-3}$-alkyl, C$_{1-6}$alkoxy, C$_{3-6}$-cycloalkoxy, C$_{1-6}$alkylthio, C$_{3-6}$-cycloalkylthio or aralkoxy each of which is optionally substituted with one or more halogens; or
  NR$_1$R$_2$ wherein R$_1$ represents hydrogen or C$_{1-3}$-alkyl and R$_2$ represents —R$_3$—(C=O)—R$_4$ wherein:
    R$_3$ represents C$_{1-6}$-alkylene, C$_{2-6}$-alkenylene, C$_{4-6}$-cycloalkylene, C$_{4-6}$-cycloalkenylene, or arylene optionally substituted with one or more halogens;
    R$_4$ represents aryl optionally substituted with one or more halogens; and
D is H, C$_{1-6}$alkyl or C$_{3-6}$-cycloalkyl; and
E is H, C$_{1-6}$-alkyl or C$_{3-6}$-cycloalkyl; and
L and M are independently —O— or —S—; and
T is C$_{1-6}$divalent saturated carbon chain optionally substituted with one or more substituents selected from
  halogen or hydroxy; or
  aryl, aralkoxy or C$_{1-3}$-alkoxy which is optionally substituted with halogen; or
T is —NR$_1$-T' wherein —NR$_1$— is linked to Z in formula (I) and wherein T' is C$_{1-6}$ alkylene which is optionally substituted with one or more halogen and R$_1$ represents hydrogen or C$_{1-3}$ alkyl; and
U is C$_{1-6}$ divalent saturated carbon chain optionally substituted with one or more substituents selected from
  halogen or hydroxy; or
  aryl, aralkoxy or C$_{1-3}$-alkoxy which is optionally substituted with halogen; or
U is —NR$_1$-U' wherein —NR$_1$— is linked to Z in formula (I) and wherein U' is C$_{1-6}$ alkylene which is optionally substituted with one or more halogen and R$_1$ represents hydrogen or C$_{1-3}$ alkyl; and
X is arylene or heteroarylene each of which is optionally substituted with one or more substituents selected from
  halogen or hydroxy; or
  C$_{1-6}$-alkyl, C$_{3-6}$-cycloalkyl, C$_{1-6}$-alkoxy, C$_{3-6}$-cycloalkoxy, C$_{1-6}$alkylthio, C$_{3-6}$-cycloalkylthio, aryl, aralkyl each of which is optionally substituted with one or more halogen; and
Y is arylene or heteroarylene each of which is optionally substituted with one or more substituents selected from
  halogen or hydroxy; or
  C$_{1-6}$-alkyl, C$_{3-6}$-cycloalkyl, C$_{1-6}$-alkoxy, C$_{3-6}$-cycloalkoxy, C$_{1-6}$alkylthio, C$_{3-6}$-cycloalkylthio, aryl, aralkyl each of which is optionally substituted with one or more halogen; and
Z is arylene, heteroarylene or a divalent polycyclic ringsystem each of which is optionally substituted with one or more substituents selected from
  halogen, oxo or hydroxy; or
  C$_{1-6}$-alkyl, C$_{3-6}$-cycloalkyl, C$_{1-6}$-alkoxy, C$_{3-6}$-cycloalkoxy, C$_{1-6}$alkylthio, C$_{3-6}$-cycloalkylthio each of which is optionally substituted with one or more halogen; or a pharmaceutically acceptable salt thereof, or a pharmaceutically acceptable solvate thereof, or any tautomeric forms, stereoisomers, mixture of stereoisomers including a racemic mixture, or polymorphs.

In one embodiment, the present invention is concerned with compounds of formula (I) wherein A is C$_{1-3}$-alkylene which is optionally substituted with one or more substituents selected from
  methyl, C$_{1-3}$-alkoxy, C$_{3-6}$-cycloalkoxy or benzyloxy each of which is optionally substituted with one or more halogen; or
  NR$_1$R$_2$ wherein R$_1$ represents hydrogen and R$_2$ represents —R$_3$—(C=O)—R$_4$ wherein:
    R$_3$ represents C$_{1-6}$-alkylene, C$_{2-6}$-alkenylene, C$_{4-6}$-cycloalkylene, C$_{4-6}$-cycloalkenylene, or phenylene optionally substituted with one or more halogens;
    R$_4$ represents phenyl optionally substituted with one or more halogens.

In another embodiment, the present invention is concerned with compounds of formula (I) wherein A is methylene or ethylene each of which is optionally substituted with one or more substituents selected from
  methoxy or ethoxy; or
  NR$_1$R$_2$ wherein R$_1$ represents hydrogen and R$_2$ represents —R$_3$—(C=O)—R$_4$ wherein R$_3$ and R4 represents phenyl.

In another embodiment, the present invention is concerned with compounds of formula (I) wherein A is ethylene which is optionally substituted with ethoxy.

In another embodiment, the present invention is concerned with compounds of formula (I) wherein A is —O-A' or —S-A' wherein —O— or —S— is linked to X in formula (I) and wherein A' is C$_{1-3}$-alkylene which is optionally substituted with one or more substituents selected from
  halogen or
  C$_{1-3}$-alkyl, C$_{1-6}$alkoxy, C$_{3-6}$-cycloalkoxy or aralkoxy each of which is optionally substituted with halogen.

In another embodiment, the present invention is concerned with compounds of formula (I) wherein A is —O-A' or —S-A' wherein —O— or —S— is linked to X in formula (I) and wherein A' is methylene or ethylene each of which is optionally substituted with one or more substituents selected from methyl, methoxy or ethoxy.

In another embodiment, the present invention is concerned with compounds of formula (I) wherein A is —O-A' wherein —O— or is linked to X in formula (I) and wherein A' is methylene or ethylene.

In another embodiment, the present invention is concerned with compounds of formula (I) wherein B is C$_{1-3}$-alkylene, which is optionally substituted with one or more substituents selected from
  methyl, C$_{1-3}$-alkoxy, C$_{3-6}$-cycloalkoxy or benzyloxy each of which is optionally substituted with one or more halogen; or
  NR$_1$R$_2$ wherein R$_1$ represents hydrogen and R$_2$ represents —R$_3$—(C=O)—R$_4$ wherein:
    R$_3$ represents C$_{1-6}$alkylene, C$_{2-6}$-alkenylene, C$_{4-6}$-cycloalkylene, C$_{4-6}$-cycloalkenylene, or phenylene optionally substituted with one or more halogens;
    R$_4$ represents phenyl optionally substituted with one or more halogens.

In another embodiment, the present invention is concerned with compounds of formula (I) wherein B is methylene or ethylene each of which is optionally substituted with one or more substituents selected from
  methoxy or ethoxy; or
  NR$_1$R$_2$ wherein R$_1$ represents hydrogen and R$_2$ represents —R$_3$—(C=O)—R$_4$ wherein R$_3$ and R4 represents phenyl.

In another embodiment, the present invention is concerned with compounds of formula (I) wherein B is ethylene which is optionally substituted with ethoxy.

In another embodiment, the present invention is concerned with compounds of formula (I) wherein B is —O— B' or —S—B' wherein —O— or —S— is linked to Y in formula (I) and wherein B' is $C_{1-3}$-alkylene which is optionally substituted with one or more substituents selected from
halogen or
$C_{1-3}$-alkyl, $C_{1-6}$alkoxy, $C_{3-6}$-cycloalkoxy or aralkoxy each of which is optionally substituted with halogen.

In another embodiment, the present invention is concerned with compounds of formula (I) wherein B is —O— B' or —S=B' wherein —O— or —S— is linked to Y in formula (I) and wherein B' is methylene or ethylene each of which is optionally substituted with one or more substituents selected from methyl, methoxy or ethoxy.

In another embodiment, the present invention is concerned with compounds of formula (I) wherein B is —O— B' wherein —O— is linked to Y in formula (I) and wherein B' is methylene or ethylene.

In another embodiment, the present invention is concerned with compounds of formula (I) wherein D is H.

In another embodiment, the present invention is concerned with compounds of formula (I) wherein D is methyl.

In another embodiment, the present invention is concerned with compounds of formula (I) wherein D is ethyl.

In another embodiment, the present invention is concerned with compounds of formula (I) wherein D is isopropyl.

In another embodiment, the present invention is concerned with compounds of formula (I) wherein E is H.

In another embodiment, the present invention is concerned with compounds of formula (I) wherein E is methyl.

In another embodiment, the present invention is concerned with compounds of formula (I) wherein E is ethyl.

In another embodiment, the present invention is concerned with compounds of formula (I) wherein E is isopropyl.

In another embodiment, the present invention is concerned with compounds of formula (I) wherein L is —O—.

In another embodiment, the present invention is concerned with compounds of formula (I) wherein L is —S—.

In another embodiment, the present invention is concerned with compounds of formula (I) wherein M is —O—.

In another embodiment, the present invention is concerned with compounds of formula (I) wherein M is —S—.

In another embodiment, the present invention is concerned with compounds of formula (I) wherein T is $C_{1-6}$ divalent saturated carbon chain optionally substituted with one or more substituents selected from phenyl, benzyloxy or $C_{1-3}$-alkoxy which is optionally substituted with halogen.

In another embodiment, the present invention is concerned with compounds of formula (I) wherein T is an unsubstituted $C_{1-6}$ divalent saturated carbon chain.

In another embodiment, the present invention is concerned with compounds of formula (I) wherein T is methylene.

In another embodiment, the present invention is concerned with compounds of formula (I) wherein T is ethylene.

In another embodiment, the present invention is concerned with compounds of formula (I) wherein T is propylene.

In another embodiment, the present invention is concerned with compounds of formula (I) wherein T is —$NR_1$-T' wherein —$NR_1$— is linked to Z in formula (I) and wherein T' is $C_{1-6}$ alkylene which is optionally substituted with one or more halogen and $R_1$ represents hydrogen or $C_{1-3}$ alkyl.

In another embodiment, the present invention is concerned with compounds of formula (I) wherein T is —$NR_1$-T' wherein —$NR_1$— is linked to Z in formula (I) and wherein T' is $C_{1-3}$ alkylene and $R_1$ represents hydrogen or $C_{1-3}$ alkyl.

In another embodiment, the present invention is concerned with compounds of formula (I) wherein T is —$NR_1$-T' wherein —$NR_1$— is linked to Z in formula (I) and wherein T' is ethylene and $R_1$ is methyl.

In another embodiment, the present invention is concerned with compounds of formula (I) wherein U is $C_{1-6}$ divalent saturated carbon chain optionally substituted with one or more substituents selected from phenyl, benzyloxy or $C_{1-3}$-alkoxy which is optionally substituted with halogen.

In another embodiment, the present invention is concerned with compounds of formula (I) wherein U is an unsubstituted $C_{1-6}$ divalent saturated carbon chain.

In another embodiment, the present invention is concerned with compounds of formula (I) wherein U is methylene.

In another embodiment, the present invention is concerned with compounds of formula (I) wherein U is ethylene.

In another embodiment, the present invention is concerned with compounds of formula (I) wherein U is propylene.

In another embodiment, the present invention is concerned with compounds of formula (I) wherein U is —$NR_1$—U' wherein —$R_1$— is linked to Z in formula (I) and wherein U' is $C_{1-6}$ alkylene which is optionally substituted with one or more halogen and $R_1$ represents hydrogen or $C_{1-3}$ alkyl.

In another embodiment, the present invention is concerned with compounds of formula (I) wherein U is —$NR_1$—U' wherein —$NR_1$— is linked to Z in formula (I) and wherein U' is $C_{1-3}$ alkylene and $R_1$ represents hydrogen or $C_{1-3}$ alkyl.

In another embodiment, the present invention is concerned with compounds of formula (I) wherein U is —$NR_1$—U' wherein —$NR_1$— is linked to Z in formula (I) and wherein U' is ethylene and $R_1$ is methyl.

In another embodiment, the present invention is concerned with compounds of formula (I) wherein X is arylene or heteroarylene each of which is optionally substituted with one or more substituents selected from
halogen; or
$C_{1-6}$alkyl, aryl each of which is optionally substituted with one or more halogen.

In another embodiment, the present invention is concerned with compounds of formula (I) wherein X is arylene optionally substituted with one or more substituents selected from
halogen; or
$C_{1-6}$alkyl, aryl each of which is optionally substituted with one or more halogen.

In another embodiment, the present invention is concerned with compounds of formula (I) wherein X is phenylene optionally substituted with one or more substituents selected from
halogen; or
$C_{1-3}$-alkyl, phenyl each of which is optionally substituted with one or more halogen.

In another embodiment, the present invention is concerned with compounds of formula (I) wherein X is phenylene optionally substituted with one or more halogen, methyl or phenyl.

In another embodiment, the present invention is concerned with compounds of formula (I) wherein X is phenylene optionally substituted with one or more trifluoromethyl or methoxy.

In another embodiment, the present invention is concerned with compounds of formula (I) wherein Y is arylene or heteroarylene each of which is optionally substituted with one or more substituents selected from
halogen; or
$C_{1-6}$-alkyl, aryl each of which is optionally substituted with one or more halogen.

In another embodiment, the present invention is concerned with compounds of formula (I) wherein Y is arylene optionally substituted with one or more substituents selected from
halogen; or
$C_{1-6}$alkyl, aryl each of which is optionally substituted with one or more halogen.

In another embodiment, the present invention is concerned with compounds of formula (I) wherein Y is phenylene optionally substituted with one or more substituents selected from
   halogen; or
   $C_{1-3}$-alkyl, phenyl each of which is optionally substituted with one or more halogen.

In another embodiment, the present invention is concerned with compounds of formula (I) wherein Y is phenylene optionally substituted with one or more halogen, methyl or phenyl.

In another embodiment, the present invention is concerned with compounds of formula (I) wherein Y is phenylene optionally substituted with one or more trifluoromethyl or methoxy.

In another embodiment, the present invention is concerned with compounds of formula (I) wherein Z is arylene, heteroarylene or a divalent polycyclic ringsystem each of which is optionally substituted with one or more substituents selected from
   halogen, oxo; or
   $C_{1-6}$alkyl, $C_{1-6}$alkoxy each of which is optionally substituted with one or more halogen.

In another embodiment, the present invention is concerned with compounds of formula (I) wherein Z is selected among the following groups:

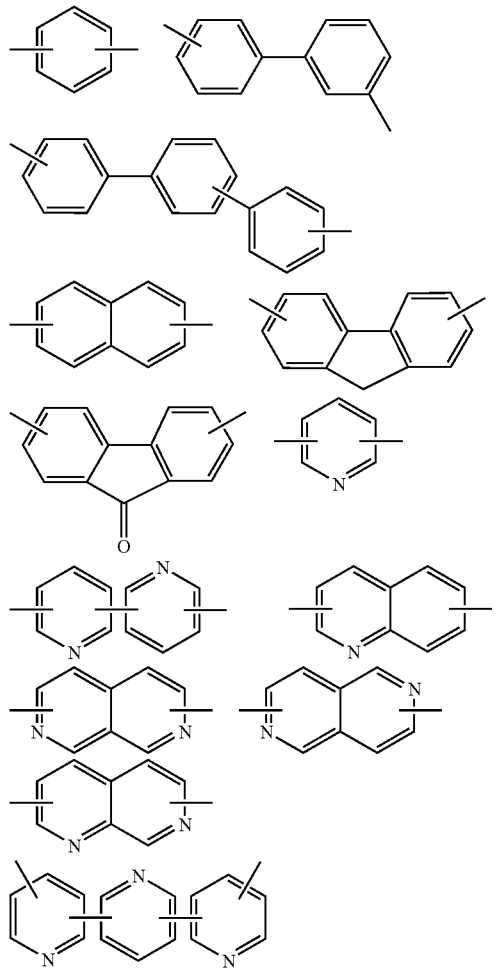

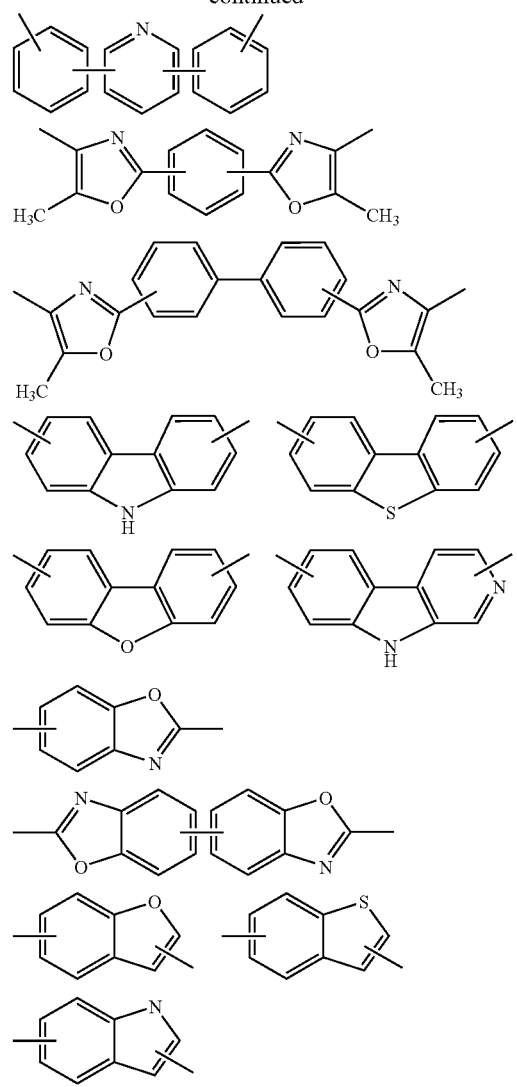

which is optionally substituted with one or more substituents selected from
   halogen or
   $C_{1-6}$-alkyl or $C_{1-6}$-alkoxy each of which is optionally substituted with one or more halogen.

In another embodiment, the present invention is concerned with compounds of formula (I) wherein Z is selected among the following groups:

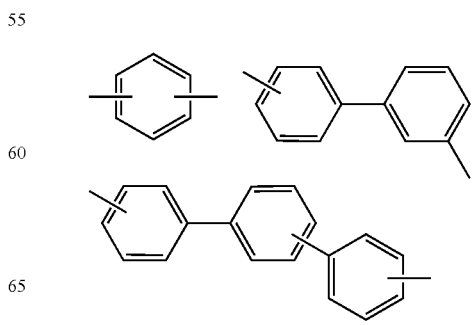

-continued

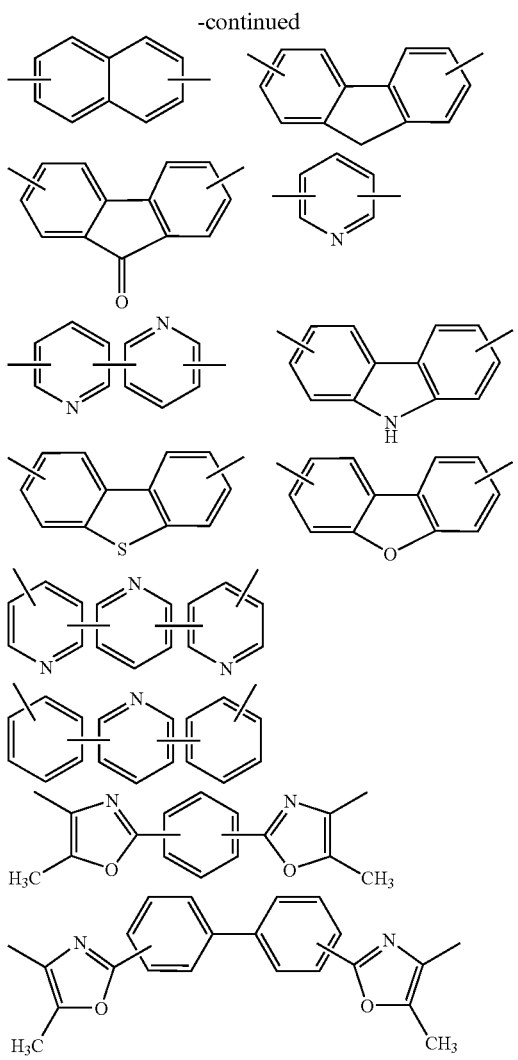
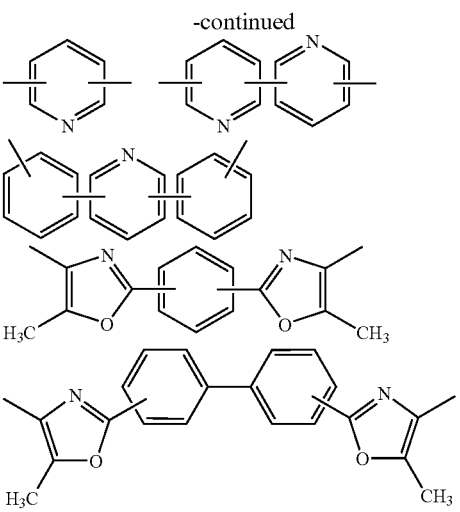

which is optionally substituted with one or more substituents selected from
halogen or
$C_{1-6}$alkyl or $C_{1-6}$-alkoxy each of which is optionally substituted with one or more halogen.

In another embodiment, the present invention is concerned with compounds of formula (I) wherein Z is selected among the following groups:

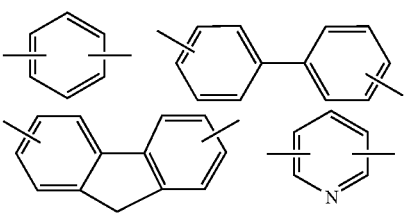

which is optionally substituted with one or more substituents selected from
halogen or
$C_{1-6}$alkyl or $C_{1-6}$alkoxy each of which is optionally substituted with one or more halogen.

In another embodiment, the present invention is concerned with compounds of formula (I) wherein Z is:

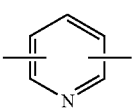

In another embodiment, the present invention is concerned with compounds of formula (I) wherein Z is:

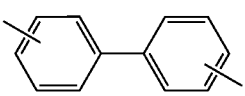

which is optionally substituted with one or more of trifluoromethyl.

which is optionally substituted with one or more substituents selected from
halogen or
$C_{1-6}$-alkyl or $C_{1-6}$-alkoxy each of which is optionally substituted with one or more halogen.

In another embodiment, the present invention is concerned with compounds of formula (I) wherein Z is selected among the following groups:

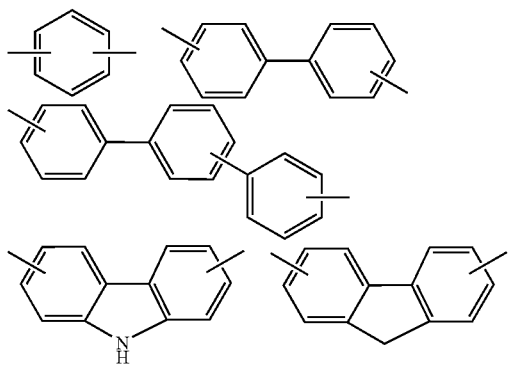

In another embodiment, the present invention is concerned with compounds of formula (I) wherein Z is:

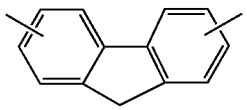

In another embodiment, the present invention is concerned with compounds of formula (I) wherein Z is:

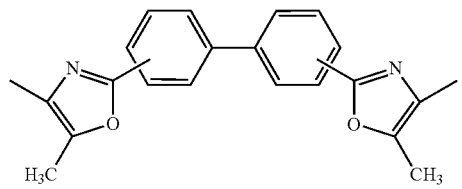

In another embodiment, the present invention is concerned with compounds of formula (I) wherein Z is:

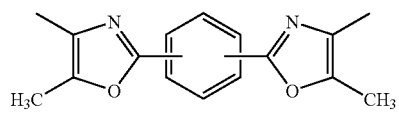

In another embodiment, the present invention is concerned with compounds of the present invention having a (S)-configuration when possible.

In another embodiment, the present invention is concerned with compounds of the present invention which is a mixed PPARα/PPARγ profile.

In another embodiment, the present invention is concerned with compounds of the present invention which is a mixed PPARα/PPARδ profile.

In another embodiment, the present invention is concerned with compounds of the present invention which is a mixed PPARγ/PPARδ profile.

In another embodiment, the present invention is concerned with compounds of the present invention which is a mixed PPARαPPARγ/PPARδ profile.

In another embodiment, the present invention is concerned with compounds of the present invention, which is a selective PPARα profile.

In another embodiment, the present invention is concerned with compounds of the present invention, which is a selective PPARγ profile.

In another embodiment, the present invention is concerned with compounds of the present invention, which is a selective PPARδ profile.

Examples of specific compounds of the invention are:

2-Ethoxy-3-[4-(2-{[6-({2-[4-(2-ethoxy-2-methoxycarbonyl-ethyl)-phenylsulfanyl]-ethyl}-methyl-amino)-pyridin-2-yl]-methyl-amino}-ethylsulfanyl)-phenyl]-propionic acid;

3-[4-(2-{[6-({2-[4-(2-Carboxy-2-ethoxy-ethyl)-2-chloro-phenylsulfanyl]-ethyl}-methyl-amino)-pyridin-2-yl]-methyl-amino}-ethylsulfanyl)-3-chloro-phenyl]-2-ethoxy-propionic acid;

(5'-{2-[(6-{[2-(2'-Ethoxycarbonylmethoxy-[1,1';3',1"]terphenyl-5'-yloxy)-ethyl]-methyl-amino}-pyridin-2-yl)-methyl-amino]-ethoxy}-[1,1';  3',1"]terphenyl-2'-yloxy)-acetic acid;

(5'-{2-[(6-{[2-(2'-Carboxymethoxy-[1,1';3',1"]terphenyl-5'-yloxy)-ethyl]-methyl-amino}-pyridin-2-yl)-methyl-amino]-ethoxy}-[1,1';3',1"]terphenyl-2'-yloxy)-acetic acid;

(S,S)-2-(2-Benzoyl-phenylamino)-3-{4-[2-({6-[(2-{4-[2-(2-benzoyl-phenylamio)-2-methoxycarbonyl-ethyl]-phenoxy}-ethyl)-methyl-amino]-pyridin-2-yl}-methyl-amino)-ethoxy]-phenyl}-propionic acid;

(S,S)-2-(2-Benzoyl-phenylamino)-3-{4-[2-({6-[(2-{4-[2-(2-benzoyl-phenylamino)-2-carboxy-ethyl]-phenoxy}-ethyl)-methyl-amino]-pyridin-2-yl}-methyl-amino)-ethoxy]-phenyl}-propionic acid;

(3-Chloro-4-{2-[(6-{[2-(2-chloro-4-ethoxycarbonylmethyl-phenoxy)-ethyl]-methyl-amino}-pyridin-2-yl)-methyl-amino]-ethoxy}-phenyl)-acetic acid;

(4-{2-[(6-{[2-(4-Carboxymethyl-2-chloro-phenoxy)-ethyl]-methyl-amino}-pyridin-2-yl)-methyl-amino]-ethoxy}-3-chloro-phenyl)-acetic acid;

(3-{2-[(6-{[2-(3-Ethoxycarbonylmethyl-phenoxy)-ethyl]-methyl-amino}-pyridin-2-yl methyl-amino]-ethoxy}-phenyl)-acetic acid;

(3-{2-[(6-{[2-(3-Carboxymethyl-phenoxy)-ethyl]-methyl-amino}-pyridin-2-yl)-methyl-amino]-ethoxy}-phenyl)-acetic acid;

(S,S)-2-Ethoxy-3-[4-(2-{[6-({2-[4-(2-ethoxy-2-ethoxycarbonyl-ethyl)-phenoxy]-ethyl}-methyl-amino)-pyridin-2-yl]-methyl-amino}-ethoxy)-phenyl]-propionic acid;

(S,S)-3-[4-(2-{[6-({2-[4-(2-Carboxy-2-ethoxy-ethyl)-phenoxy]-ethyl}-methyl-amino)-pyridin-2-yl]-methyl-amino}-ethoxy)-phenyl]-2-ethoxy-propionic acid;

(S,S)-2-Ethoxy-3-{4-[3-(4'-{3-[4-(2-ethoxy-2-isopropoxycarbonyl-ethyl)-phenoxy]-propyl}-2,2'-bis-trifluoromethyl-biphenyl-4-yl)-propoxy]-phenyl}-propionic acid;

(S,S)-3-{4-[3-(4'-{3-[4-(2-Carboxy-2-ethoxy-ethyl)-phenoxy]-propyl}-2,2'-bis-trifluoromethyl-biphenyl-4-yl)-propoxy]-phenyl}-2-ethoxy-propionic acid;

(S,S)-2-Ethoxy-3-{4-[3-(4'-{3-[4-(2-ethoxy-2-isopropoxycarbonyl-ethyl)-phenoxy]-propyl}-3,3'-bis-trifluoromethyl-biphenyl-4-yl)-propoxy]-phenyl}-propionic acid;

(S,S)-3-{4-[3-(4'-{3-[4-(2-Carboxy-2-ethoxy-ethyl)-phenoxy]-propyl}-3,3'-bis-trifluoromethyl-biphenyl-4-yl)-propoxy]-phenyl}-2-ethoxy-propionic acid;

(S,S)-3-{3-Bromo-4-[3-(4'-{3-[2-bromo-4-(2-ethoxy-2-isopropoxycarbonyl-ethyl)-phenoxy]-propyl}-2,2'-bis-trifluoromethyl-biphenyl-4-yl)-propoxy]-phenyl}-2-ethoxy-propionic acid;

(S,S)  -3-{3-Bromo-4-[3-(4'-{3-[2-bromo-4-(2-carboxy-2-ethoxy-ethyl)-phenoxy]-propyl}-2,2'-bis-trifluoromethyl-biphenyl-4-yl)-propoxy]-phenyl}-2-ethoxy-propionic acid;

(S,S)-3-{3-Bromo-4-[3-(4'-{3-[2-bromo-4-(2-ethoxy-2-isopropoxycarbonyl-ethyl)-phenoxy]-propyl}-3,3'-bis-trifluoromethyl-biphenyl-4-yl)-propoxy]-phenyl}-2-ethoxy-propionic acid;

(S,S)-3-{3-Bromo-4-[3-(4'-{3-[2-bromo-4-(2-carboxy-2-ethoxy-ethyl)-phenoxy]-propyl}-3,3'-bis-trifluoromethyl-biphenyl-4-yl)-propoxy]-phenyl}-2-ethoxy-propionic acid;

(S,S)-3-{3-Bromo-4-[3-(7-{3-[2-bromo-4-(2-ethoxy-2-isopropoxycarbonyl-ethyl)-phenoxy]-propyl}-9H-fluoren-2-yl)-propoxy]-phenyl}-2-ethoxy-propionic acid isopropyl ester;

(S,S)-3-{3-Bromo-4-[3-(7-{3-[2-bromo-4-(2-carboxy-2-ethoxy-ethyl)-phenoxy]-propyl}-9H-fluoren-2-yl)-propoxy]-phenyl}-2-ethoxy-propionic acid;

(S,S)-2-Ethoxy-3-{4-[3-(7-{3-[4-(2-ethoxy-2-isopropoxycarbonyl-ethyl)-phenoxy]-propyl}-9H-fluoren-2-yl)-propoxy]-phenyl}-propionic acid isopropyl ester;

(S,S)-3-{4-[3-(7-{3-[4-(2-Carboxy-2-ethoxy-ethyl)-phenoxy]-propyl}-9H-fluoren-2yl)-propoxy]-phenyl}-1-ethoxy-propionic acid;

[4-(3-{4'-[3-(4-Methoxycarbonylmethoxy-3-methyl-phenylsulfanyl)-propyl]-2,2'-bis-trifluoro-methyl-biphenyl-4-yl}-propylsulfanyl)-2-methyl-phenoxy]-acetic acid;

[4-(3-{4'-[3-(4-Methoxycarbonylmethoxy-3-methyl-phenylsulfanyl)-propyl]-3,3'-bis-trifluoro-methyl-biphenyl-4-yl}-propylsulfanyl)-2-methyl-phenoxy]-acetic acid;

[4-(3-{4'-[3-(4-Carboxymethoxy-3-methyl-phenylsulfanyl)-propyl]-3,3'-bis-trifluoromethyl-biphenyl-4-yl}-propyl-sulfanyl)-2-methyl-phenoxy]-acetic acid;

[4-(3-{7-[3-(4-Methoxycarbonylmethoxy-3-methyl-phenylsulfanyl)-propyl]-9H-fluoren-2-yl}-propylsulfanyl)-2-methyl-phenoxy]-acetic acid;

[4-(3-(7-[3-(4-Carboxymethoxy-3-methyl-phenylsulfanyl)-propyl]-9H-fluoren-2-yl)-propylsulfanyl)-2-methyl-phenoxy]-acetic acid;

(4-{2-[2-(3-{4-[2-(4-Methoxycarbonylmethoxy-3-methyl-phenylsulfanyl)-ethyl]-5-methyl-oxazol-2-yl}-phenyl)-5-methyl-oxazol-4-yl]-ethylsulfanyl}-2-methyl-phenoxy)-acetic acid;

(4-{2-[2-(3-{4-[2-(4-Carboxymethoxy-3-methyl-phenylsulfanyl)-ethyl]-5-methyl-oxazol-2-yl}-phenyl)-5-methyl-oxazol-4-yl]-ethylsulfanyl}-2-methyl-phenoxy)-acetic acid;

(S,S)-2-Ethoxy-3-[4-(2-{2-[4'-(4-{2-[4-(2-ethoxy-2-isopropoxycarbonyl-ethyl)-phenoxy]-ethyl}-5-methyl-oxazol-2-yl)-biphenyl-4-yl]-5-methyl-oxazol-4-yl}-ethoxy)-phenyl]-propionic acid;

(S,S )-3-[4-(2-{2-[4'-(4-{2-[4-(2-Carboxy-2-ethoxy-ethyl)-phenoxy]-ethyl}-5-methyl-oxazol-2-yl)-biphenyl-4-yl]-5-methyl-oxazol-4-yl}-ethoxy)-phenyl]-2-ethoxy-propionic acid;

(S,S)-2-Ethoxy-3-[4-(2-{2-[3-(4-{2-[4-(2-ethoxy-2-isopropoxycarbonyl-ethyl)-phenoxy]-ethyl}-5-methyl-oxazol-2-yl)-phenyl]-5-methyl-oxazol-4-yl}-ethoxy)-phenyl]-propionic acid;

(S,S)-3-[4-(2-{2-[3-(4-{2-[4-(2-Carboxy-2-ethoxy-ethyl)-phenoxy]-ethyl}-5-methyl-oxazol-2-yl)-phenyl]-5-methyl-oxazol-4-yl}-ethoxy)-phenyl]-2-ethoxy-propionic acid; or a salt thereof with a pharmaceutically acceptable acid or base, or any optical isomer or mixture of optical isomers, including a racemic mixture, or any tautomeric forms.

Other examples of specific compounds of the invention are:

[4-(3-{4'-[3-(4-Carboxymethylsulfanyl-3-chloro-phenylsulfanyl)-propyl]-3,3'-bis-rifluoromethyl-biphenyl-4-yl}-propylsulfanyl)-2-chloro-phenylsulfanyl]-acetic acid;

[4-[3-[4'-[3-(4-Carboxymethoxy-3-trifluoromethylphenylsulfanyl)propyl]biphenyl-4-yl]-propyl-sulfanyl]-2-trifluoromethylphenoxy]acetic acid;

[4-[3-[4'-[3-(4-Carboxymethoxy-3-chlorophenylsulfanyl)propyl]-3,3'-bis-trifluoromethylbiphenyl-4-yl]propylsulfanyl]-2-chlorophenoxy]acetic acid;

[4-(3-{4'-[3-(4-Carboxymethoxy-3-chloro-phenylsulfanyl)-propyl]-biphenyl-4-yl}-propyl-sulfanyl)-2-chloro-phenoxy]-acetic acid;

[4-(3-{4'-[3-(4-Carboxymethoxy-3-methoxy-phenylsulfanyl)-propyl]-biphenyl-4-yl}-propyl-sulfanyl)-2-methoxy-phenoxy]-acetic acid;

{4-[3-(4-{4-[3-(4-Carboxymethoxy-3-trifluoromethyl-phenylsulfanyl)-propyl]-2-trifluoromethyl-phenylsulfanyl}-3-trifluoromethyl-phenyl)-propylsulfanyl]-2-trifluoromethyl-phenoxy}-acetic acid; or a salt thereof with a pharmaceutically acceptable acid or base, or any optical isomer or mixture of optical isomers, including a racemic mixture, or any tautomeric forms.

Other examples of specific compounds of the invention are:

3-[4-(2-{[6-({2-[4-(2-Carboxy-2-ethoxy-ethyl)-phenoxy]-ethyl}-methyl-amino)-pyridin-2-yl]-methyl-amino}ethoxy)-phenyl]-2-ethoxy-propionic acid;

(3-{2-[(6-{[2-(3-Carboxymethyl-phenoxy)-ethyl]-methyl-amino}pyridin-2-yl)-methyl-amino]-ethoxy}-phenyl)-acetic acid;

2-(2-Benzoyl-phenylamino)-3-{4-[2-({6-[(2-{4-[2-(2-benzoyl-phenylamino)-2-carboxy-ethyl]-phenoxy}-ethyl)-methyl-amino]-pyridin-2-yl}-methyl-amino)-ethoxy]-phenyl}-propionic acid;

(5'-{2-[(6-{[2-(2'-Carboxymethoxy-[1,1';3',1'']terphenyl-5'-yloxy)-ethyl]-methyl-amino}-pyridin-2-yl)-methyl-amino]-ethoxy}-[1,1';3',1'']terphenyl-2'-yloxy)-acetic acid;

3-[4-(2-{[6-({2-[4-(2-Carboxy-2-ethoxy-ethyl)-phenylsulfanyl]-ethyl}-methyl-amino)-pyridin-2-yl]-methyl-amino}-ethylsulfanyl)-phenyl]-2-ethoxy-propionic acid;

(4-{2-[(6-{[2-(4-Carboxymethyl-2-chloro-phenoxy)-ethyl]-methyl-amino}-pyridin-2-yl)-methyl-amino]-ethoxy}-3-chloro-phenyl)-acetic acid;

(4-{2-[(6-{[2-(4-Carboxymethyl-2-bromo-phenoxy)-ethyl]-methyl-amino}-pyridin-2-yl)-methyl-amino]-ethoxy}-3-bromo-phenyl)-acetic acid;

(4-{2-[(6-{[2-(4-Carboxymethoxy-3-methyl-phenylsulfanyl)-ethyl]-methyl-amino}-pyridin-2-yl)-methyl-amino]-ethylsulfanyl}-2-methyl-phenoxy)-acetic acid;

(4-{2-[(6-{[2-(4-Carboxymethoxy-phenylsulfanyl)-ethyl]-methyl-amino}-pyridin-2-yl)-methyl-amino]-ethylsulfanyl}-phenoxy)-acetic acid;

(3-{2-[(6-{[2-(3-Carboxymethyl-phenylsulfanyl)-ethyl]-methyl-amino}-pyridin-2-yl)-methyl-amino]-ethylsulfanyl}-phenyl)-acetic acid;

(4-{2-[(6-{[2-(4-Carboxymethyl-phenylsulfanyl)-ethyl]-methyl-amino}-pyridin-2-yl)-methyl-amino]-ethylsulfanyl}-phenyl)-acetic acid;

2-(2-Benzoyl-phenylamino)-3-{4-[2-({6-[(2-{4-[2-(2-benzoyl-phenylamino)-2-carboxy-ethyl]-phenylsulfanyl}-ethyl)-methyl-amino]-pyridin-2-yl}-methyl-amino)-ethylsulfanyl]-phenyl}-propionic acid;

3-{4-[2-({6-[(2-{4-[2-Carboxy-2-(1-methyl-3-oxo-3-phenyl-propenylamino)-ethyl]-phenyl-sulfanyl}-ethyl)-methyl-amino]-pyridin-2-yl}-methyl-amino)-ethylsulfanyl]-phenyl}-2-(1-methyl-3-oxo-3-phenyl-propenylamino)-propionic acid;

3-{4-[2-({6-[(2-{4-[2-Carboxy-2-( 1 -methyl-3-oxo-3-phenyl-propenylamino)-ethyl]-phenoxy}-ethyl)-methyl-amino]-pyridin-2-yl}-methyl-amino)-ethoxy]-phenyl}-2-(1-methyl-3-oxo-3-phenyl-propenylamino)-propionic acid;

(4-{2-[(6-{[2-(4-Carboxymethyl-2-chloro-phenylsufanyl)-ethyl]-methyl-amino}-pyridin-2-yl)-methyl-amino]-ethylsulfanyl}-3-chloro-phenyl)-acetic acid;

(4-{2-[(6-{[2-(4-Carboxymethyl-2-bromo-phenylsulfanyl)-ethyl]-methyl-amino}-pyridin-2-yl)-methyl-amino]-ethylsulfanyl}-3-bromo-phenyl)-acetic acid;

3-[4-(2-{2-[3-(4-{2-[4-(2-Carboxy-2-ethoxy-ethyl)-phenoxy]-ethyl}-5-methyl-oxazol-2yl)-phenyl]-5-methyl-oxazol-4-yl}-ethoxy)-phenyl]-2-ethoxy-propionic acid;

(4-{2-[2-(3-{4-[2-(4-Carboxymethoxy-3-methyl-phenylsulfanyl)-ethyl]-5-methyl-oxazol-2-yl}-phenyl)-5-methyl-oxazol-4-yl]-ethylsulfanyl}-2-methyl-phenoxy)-acetic acid;

(4-{2-[2-(3-{4-[2-(4-Carboxymethoxy-3-methyl-phenoxy)-ethyl]-5-methyl-oxazol-2-yl}-phenyl)-5-methyl-oxazol-4-yl]-ethoxy}-2-methyl-phenoxy)-acetic acid;

(4-{2-[2-(3-{4-[2-(4-Carboxymethoxy-phenylsulfanyl)-ethyl]-5-methyl-oxazol-2-yl}-phenyl)-5-methyl-oxazol-4-yl]-ethylsulfanyl}-phenoxy)-acetic acid;

(4-{2-[2-(3-{4-[2-(4-Carboxymethoxy-phenylsulfanyl)-ethyl]-5-methyl-oxazol-2-yl}-phenyl)-5-methyl-oxazol-4-yl]-ethylsulfanyl}-phenoxy)-acetic acid;

3-[4-(2-{2-[3-(4-{2-[4-(2-Carboxy-2-ethoxy-ethyl)-phenylsulfanyl]-ethyl}-5-methyl-oxazol-2-yl)-phenyl]-5-methyl-oxazol-4-yl}-ethylsulfanyl)-phenyl]-2-ethoxy-propionic acid;

3-{4-[3-(7-{3-[4-(2-Carboxy-2-ethoxy-ethyl)-phenoxy]-propyl}-9H-fluoren-2-yl)-propoxyl]-phenyl}-2-ethoxy-propionic acid;

3-{4-[3-(7-{3-[4-(2-Carboxy-2-ethoxy-ethyl)-phenylsulfanyl]-propyl}-9H-fluoren-2-yl)-propylsulfanyl]-phenyl}-2-ethoxy-propionic acid;

[4-(3-{7-[3-(4-Carboxymethoxy-3-methyl-phenylsulfanyl)-propyl]-9H-fluoren-2-yl}-propyl-sulfanyl)-2-methyl-phenoxy]-acetic acid;

[4-(3-{7-[3-(4-Carboxymethoxy-phenylsulfanyl)-propyl]-9H-fluoren-2-yl}-propylsulfanyl)-phenoxy]-acetic acid;

3-{3-Bromo-4-[3-(7-{3-[2-bromo-4-(2-carboxy-2-ethoxy-ethyl)-phenoxy]-propyl}-9H-fluoren-2-yl)-propoxy]-phenyl}-2-ethoxy-propionic acid;

3-{3-Bromo-4-[3-(7-{3-[2-bromo-4-(2-carboxy-2-ethoxy-ethyl)-phenylsulfanyl]-propyl}-9H-fluoren-2-yl)-propylsulfanyl]-phenyl}-2-ethoxy-propionic acid;

3-{4-[3-(4'-{3-[4-(2-Carboxy-2-ethoxy-ethyl)-phenoxy]-propyl}-2,2'-bis-trifluoromethyl-biphenyl-4-yl)-propoxy]-phenyl}-2-ethoxy-propionic acid;

3-{4-[3-(4'-{3-[4-(2-Carboxy-2-ethoxy-ethyl)-phenoxy]-propyl}-3,3'-bis-trifluoromethyl-biphenyl-4-yl)-propoxy]-phenyl}-2-ethoxy-propionic acid;

3-{3-Bromo-4-[3-(4'-{3-[2-bromo-4-(2-carboxy-2-ethoxy-ethyl)-phenoxy]-propyl}-2,2'-bis-trifluoromethyl-biphenyl-4-yl)-propoxy]-phenyl}-2-ethoxy-propionic acid;

3-{3-Bromo-4-[3-(4'-{3-[2-bromo-4-(2-carboxy-2-ethoxy-ethyl)-phenoxy]-propyl}-3,3'-bis-trifluoromethyl-biphenyl-4-yl)-propoxy]-phenyl}-2-ethoxy-propionic acid;

[4-(3-{4'-[3-(4-Carboxymethoxy-3-methyl-phenylsulfanyl)-propyl]-3,3'-bis-trifluoromethyl-biphenyl-4-yl}-propylsulfanyl)-2-methyl-phenoxy]-acetic acid;

[4-(3-{4'-[3-(4-Carboxymethoxy-phenylsulfanylypropyl]-3,3'-bis-trifluoromethyl-biphenyl-4-yl}-propylsulfanyl)-phenoxy]-acetic acid;

[4-(3-{4'-[3-(4-Carboxymethoxy-phenoxy)-propyl]-3,3'-bis-trifluoromethyl-biphenyl-4-yl}-propoxy)-phenoxy]-acetic acid;

[4-(3-{4'-[3-(4-Carboxymethoxy-3-methyl-phenoxy)-propyl]-3,3'-bis-trifluoromethyl-biphenyl-4-yl}-propoxy)-2-methyl-phenoxy]-acetic acid;

[4-(3-{4'-[3-(4-Carboxymethoxy-3-methyl-phenylsulfanyl)-propyl]-2,2'-bis-trifluoromethyl-biphenyl-4-yl}-propylsulfanyl)-2-methyl-phenoxy]-acetic acid;

[4-(3-{4'-[3-(4-Carboxymethoxy-3-methyl-phenoxy)-propyl]-2,2'-bis-trifluoromethyl-biphenyl-4-yl}-propoxy)-2-methyl-phenoxy]-acetic acid;

3-[4-(2-{2-[4'-(4-{2-[4-(2-Carboxy-2-ethoxy-ethyl)-phenoxy]-ethyl}-5-methyl-oxazol-2-yl)-biphenyl-4-yl]-5-methyl-oxazol-4-yl}-ethoxy)-phenyl]-2-ethoxy-propionic acid; or a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the present compound with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the present compound may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of the compound of the present invnetion may be prepared by hydrolysing the pure diastereomeric amide.

Various polymorphs of compound of the present invention forming part of this invention may be prepared by crystallization of compound of the invention under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the the present invention. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the present invention or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the present invention or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

In another aspect, the present invention relates to a method of treating and/or preventing Type I or Type II diabetes.

In a still further aspect, the present invention relates to the use of one or more compounds of the present invention or pharmaceutically acceptable salts thereof for the preparation of a pharmaceutical composition for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

In yet another aspect, the invention also relates to the use of the present compounds, which after administration lower the bio-markers of atherosclerosis like, but not limited to, c-reactive protein (CRP), TNFα and IL-6.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, fenofibrate, bezafibrate, tesaglitazar, EML-4156, LY-518674, LY-519818, MK-767, atorvastatin, fluvastatin, lovastatin, pravastatin, simvastatin, cerivastin, acipimox, ezetimibe, probucol, dextrothyroxine or nicotinic acid.

In yet another embodiment the present compounds are administered in combination with a thiazolidinedione e.g. troglitazone, ciglitazone, pioglitazone or rosiglitazone.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, $19^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of the present invention or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the invention dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

If desired, the pharmaceutical composition of the invention may comprise the compound of the present invention in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

Any novel feature or combination of features described herein is considered essential to this invention.

The present invention is further illustrated in the following representative examples which are, however, not intended to limit the scope of the invention in any way.

EXAMPLES

The following examples and general procedures refer to intermediate compounds and final products identified in the specification and in the synthesis schemes. The preparation of the compounds of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed nuclear magnetic resonance (NMR). NMR shifts ($\delta$) are given in parts per million (ppm). Mp is melting point and is given in ° C.

The abbreviations as used in the examples have the following meaning:

| THF: | tetrahydrofuran |
|---|---|
| DMSO: | dimethylsulfoxide |
| CDCl$_3$: | deutorated chloroform |
| DMF: | N,N-dimethylformamide |
| min: | minutes |
| h: | hours |

General Procedure (A)

Step A:

Reacting a compound of formula (a)

Hlg-Z-Hlg       (a)

wherein Z is defined as above and wherein Hlg is bromine or iodine, with an appropriate compound P, where P is an unsaturated alcohol or an unsaturated ester, through a cross-coupling reaction employing a Pd catalyst such as Pd(PPh$_3$)$_2$ or PdCl$_2$(PPh$_3$)$_2$ and a catalytic amount of in example copper(I) iodide and an organic amine base, such as and if needed a co-solvent to give a compound of formula (b)

P-Z-Hlg       (b)

wherein Z and P are defined as above and wherein Hlg is bromine or iodine.

Step B:
Reacting a compound of formula (b) wherein Z and P are defined as above and wherein Hlg is bromine or iodine, with a appropriate compound of formula P', wherein P' is an unsaturated alcohol or an unsaturated ester, through a cross-coupling reaction employing a Pd catalyst such as Pd(PPh$_3$)$_2$ or PdCl$_2$(PPh$_3$)$_2$ and a catalytic amount of in example copper(I) iodide and an organic amine base, such as and if needed a co-solvent to give a compound of formula (c)

P-Z-P'                                               (c)

wherein Z, P and P' are defined as above.

Step C:
Reacting a compound of formula (c), wherein P, Z and P' are as defined above, with a reducing agent such as NaBH$_4$ or LiBH$_4$ to give a compounds of formula (d)

HO-T-Z-U—OH                            (d)

wherein T, Z and U are defined as above.

Step D:
Reacting a compound of formula (d), wherein T, Z and U are defined as above, with a compound of formula (e)

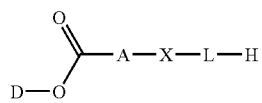

wherein A, X and D are defined as above except that D is not hydrogen, under Mitsunobu conditions, using a reagent such as triphenylphosphine/diethylazodicarboxylate and the like, to obtain a compound of formula (f)

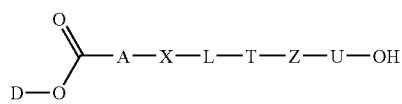

wherein A, D, L, T, U, X, and Z are defined as above, except that D is not hydrogen.

Step E:
Reacting a compound of formula (f), wherein A, D, L, T, U, X, and Z are defined as above, except that D is not hydrogen, with a compound of formula (g)

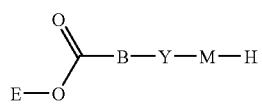

wherein B, M, Y and E are defined as above except that E is not hydrogen, under Mitsunobu conditions, using a reagent such as triphenylphosphine/diethylazodicarboxylate and the like, to obtain a compound of formula (I), wherein A, B, D, E, L, M, T, U, X, Y and Z are defined as above, except that D and E are not hydrogen.

Step D and E may be carried out in one step giving a compound of formula (I), wherein A and B are identical, D and E are identical, L and M are identical and X and Y are identical.

General Procedure (B)

Step A:
Converting the —OH functionality in the compound of formula (d), wherein T, Z and U are defined as above, to an appropriate leaving group (Q) such as p-toluenesulfonate, methanesulfonate, halogen (for example by methods according to: Houben-Weyl, Methoden der organischen Chemie, Alkohole III, 6/1b, Thieme-Verlag 1984, 4th Ed., pp. 927-939; Comprehensive Organic Transformations. A guide to functional group preparations, VCH Publishers 1989, 1$^{st}$ Ed., pp. 353-363 and *J. Org. Chem.*, Vol. 36 (20), 3044-3045, 1971), triflate and the like, to give a compound of formula (h)

Q-T-Z-U-Q                                         (h)

wherein Q, T, U and Z are defined as above.

Step B:
Reacting the compound of formula (h) wherein Q is a leaving group such as p-toluenesulfonate, methanesulfonate, halogen, triflate and the like and wherein T, U and Z are defined as above with a compound of formula (e), wherein A, L, X and D are defined as above except that D is not hydrogen, to give a compound of formula (i)

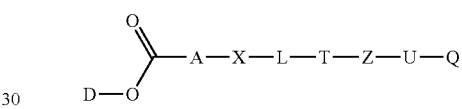

wherein A, D, L, Q, T, U, X, and Z are defined as above, except that D is not hydrogen.

Step C:
Reacting the compound of formula (i) wherein Q is a leaving group such as p-toluenesulfonate, methanesulfonate, halogen, triflate and the like and wherein A, D, L, Q, T, U, X, and Z are defined as above with a compound of formula (g), wherein B, M, Y and E are defined as above except that E is not hydrogen, to give a compound of formula (I) wherein A, B, D, E, L, M, T, U, X, Y and Z are defined as above, except that D and E is not hydrogen.

Step B and C may be carried out in one step giving a compound of formula (I), wherein A and B are identical, D and E are identical, L and M are identical and X and Y are identical.

General Procedure (C)

Step A:
By chemical or enzymatic saponification of a compound of formula (I) wherein A, B, D, E, L, M, T, U, X, Y and Z are defined as above, except that D and E are not hydrogen, to give a compound of formula (I) wherein A, B, L, M, T, U, X, Y and Z are defined as above, and wherein D and E is hydrogen.

General Procedure (D)

Step A:
Hydrolyze a compound of formula (I), wherein A, B, D, E, L, M, T, U, X, Y and Z are defined as above, except that D and E are not hydrogen, to give a compound of formula (I) wherein A, B, L, M, T, U, X, Y and Z are defined as above, and wherein D and E is hydrogen, using aqueous NaOH or the like.

General Procedure (E)

Step A:

Reacting a compound of formula (a), wherein Z is defined as above and wherein Hlg is bromine or iodine, with a compound of formula HO-T'-HNR$_1$, wherein T' and R$_1$ are as defined, above, to give a compound of formula (j)

HO-T'-NR$_1$·Z-Hlg     (j)

wherein T', R$_1$ and Z is defined as above and wherein Hlg is bromine or iodine.

Step B:

Reacting a compound of formula (J), wherein T', R$_1$ and Z is defined as above and wherein Hlg is bromine or iodine, with a compound of formula HO—U'—HNR$_1$, wherein U' and R$_1$ are as defined above, to give a compound of formula (k)

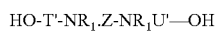
HO-T'-NR$_1$·Z-NR$_1$U'—OH     (k)

wherein T', R$_1$, U', Z are as defined above.

Step C:

Reacting a compound of formula (k), wherein T', Z and U' are defined as above, with a compound of formula (e), wherein A, X and D are defined as above except that D is not hydrogen, under Mitsunobu conditions, using a reagent such as triphenylphosphine/diethylazodicarboxylate and the like, to obtain a compound of formula (m)

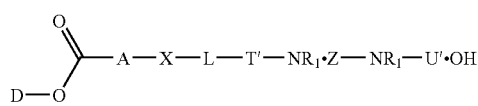

wherein A, D, L, R$_1$, T', U', X, and Z are defined as above, except that D is not hydrogen.

Step D:

Reaction a compound of formula (m), wherein A, D, L, T', R$_1$, U', X, and Z are defined as above, except that D is not hydrogen, with a compound of formula (g), wherein B, M, Y and E are defined as above except that E is not hydrogen, under Mitsunobu conditions, using a reagent such as triphenylphosphine/diethylazodicarboxylate and the like, to obtain a compound of formula (n),

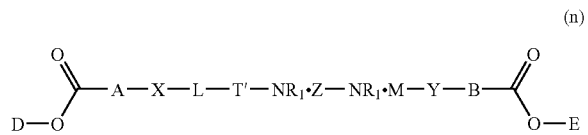

wherein A, B, D, E, L, M, T, R$_1$, U', X, Y and Z are defined as above, except that D and E are not hydrogen.

Step D and E may be carried out in one step giving a compound of formula (n), wherein A and B are identical, D and E are identical, L and M are identical and X and Y are identical.

Intermediate 1

(4-Mercapto-2-methyl-phenoxy)-acetic acid methyl ester

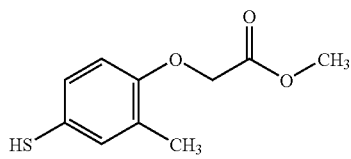

Step 1:

o-Cresol (100 g, 0.925 mol) was dissolved in 2-butanone (1200 ml), potassium carbonate (191.7 g, 1.5 mol) and ethyl bromoacetate (162.2 g, 0.971 mol) were added and the mixture was refluxed under stirring for 24 h and then left to stand overnight. The solid was filtered off, the filtrate was evaporated and dissolved in benzene (400 ml). The solution was washed with water (200 ml), 5% solution of sodium carbonate (100 ml) and dried over MgSO$_4$. The residue (ca 200 g) was distilled in vacuo. This afforded 161.9 g (90.1 %) of (2-methyl-phenoxy)-acetic acid ethyl ester, b.p. 120-130° C./2 kPa.

Step 2:

Chlorosulfonic acid (180.9 g, 104 ml, 1.553 mol) was cooled to −2-0° C. and then the above (2-methyl-phenoxy)-acetic acid ethyl ester (75.35 g, 0.388 mol) was added dropwise under stirring at such rate that the temperature of the reaction mixture did not exceed 0° C. (20 min). The mixture was left to warm to ambient temperature (1 h) and then poured on crushed ice (1 kg). The crystalline product was filtered off, washed with water (500 ml) and dried on air to constant weight. This gave 108.4 g (95.5%) crude (4-chlorosulfonyl-2-methylphenoxy)-acetic acid ethyl ester. The product was crystallized from cyclohexane (500 ml) affording 73.3 g (64.6%) pure product. M.p. 86-89° C.

$^1$H NMR (300 MHz, CDCl$_3$): δ 7.84 (m, 2 H); 6.80 (m, 1 H); 4.76 (s, 2 H); 4.29 (q, J=7.1 Hz); 2.37 (s, 3 H); 1.31 (s, 3 H).

Step 3:

To the mixture of above sulfochloride (97.7 g, 0.333 mol), tin (189.9 g, 1.59 mol) and methanol (170 ml) concentrated hydrochloric acid was added dropwise under vigorous stirring during 20 min. The reaction became exothermic and began to reflux spontaneously.

The reaction mixture was further heated to reflux for 3 hours, then cooled and poured to crushed ice (1 kg). The mixture was extracted with diethyl ether (3×200 ml), the ethereal solutions were washed with water (2×80 ml), dried over MgSO$_4$ and evaporated in vacuo. The residue (97.7 g) was dissolved in benzene (300 ml), passed trough column of silica gel (Fluka 60, 800 g) and the column was washed with benzene (2500 ml). Collected benzene solutions were evaporated and the residue was distilled in vacuo. This afforded 41.3 g (58.4%) of (4-mercapto-2-methylphenoxy)-acetic acid methyl ester as oil, b.p. 136.5-137° C./133 Pa.

$^1$H NMR (250 MHz, CDCl$_3$): δ 7.04 (m)+7.04 (m), Σ 2 H; 6.54 (m, 1 H); 2.20 (m, 3 H); 4.56 (s, 2 H); 3.73 (s, 3 H); 3.34 (s, 1 H).

Intermediate 2

2-Ethoxy-3-(4-mercapto-phenyl)-propionic acid methyl ester

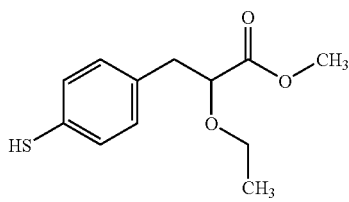

Method A:

Step 1:

A mixture of ethyl 3-(4-hydroxyphenyl)-2-ethoxypropanoate (100.8 g, 0.423 mol), triethylamine (83.4 g, 115 ml, 0.824 mol), 4-dimethylaminopyridine (5.2 g, 42.3 mmol) and dimethylthiocarbamoyl chloride (62.6 g, 0.507 mol) in dioxane (640 ml) was stirred and heated at 100° C. for 10 h in nitrogen atmosphere. The solid was filtered off, washed with dioxane and the filtrates were evaporated in vacuo. The residue was dissolved in dichloromethane (600 ml), the solution was washed with water (3×250 ml), dried (MgSO$_4$) and passed through column of silica gel (Fluka 60, 500 g). The column was washed with 500 ml dichloromethane, collected dichloromethane solutions were evaporated to yield 140.1 g (~100%) of 3-(4-dimethylthiocarbamoyloxy-phenyl)-2-ethoxy-propionic acid ethyl ester as an oil, which was used to next step.

Step 2:

The mixture the above compound (140 g, 0.423 mol) and tetradecane (1000 ml) was vigorously stirred under argon atmosphere at 230-245° C. for 8 h. The reaction mixture was cooled, tetradecane layer was separated and the residue was decanted with n-hexane (2×150 ml). The residue was dissolved in benzene (150 ml) and passed through a column of silica gel (Fluka 60, 600 g). The column was washed with benzene (4000 ml) and collected benzene solutions were evaporated in vacuo. This afforded 90.2 g (65.5%) of 3-(4-dimethyl-carbamoylsulfanyl-phenyl)-2-ethoxypropionic acid ethyl ester as an oil.

$^1$H NMR (300 MHz, CDCl$_3$): δ 7.41 (d, J=4.5 Hz, 2 H); 7.26 (d, J=4.5 Hz, 2 H); 4.15 (a, J=7.2 Hz, 2 H); 3.99 (t, J=5.8 Hz, 1 H); 3.59 (quint, 1 H); 3.33 (quint, 1 H); 2.99 (m, 6 H); 1.23 (t, J=7.1 Hz, 3 H); 1.17 (t, J=7.1 Hz, 3 H).

Step 3:

The solution of above ester (90.0 g, 0.2765) in tetrahydrofuran (370 ml) was cooled to 10° C. The solution of 85% potassium hydroxide (58.4 g, 0.885 mol) in methanol (150 ml) was added dropwise and the reaction mixture was stirred at ambient temperature for 15 h. Diethyl ether (250 ml) and water (250 ml) were added and the mixture was acidified under cooling and stirring with 15% hydrochloric acid (pH=1). The ethereal layer was separated. and water the layer was extracted with diethyl ether (3×250 ml). Collected organic solutions were washed with water (2×100 ml), brine (80 ml), dried (MgSO$_4$) and evaporated in vacuo. The residue was purified by chromatography (silica gel Fluka 60, 600 g). Elution with chloroform (2000 ml) and then with mixture of chloroform/methanol 95: 5 (1000 ml) yielded 64 g (~100%) of 2-ethoxy-3-(4-mercapto-phenyl)-propionic acid as an oil.

$^1$H NMR (300 MHz, CDCl$_3$): δ 7.17 (m, 2 H); 7.11 (m, 2 H); 4.01 (dd, 1 H); 3.62 (dq, 1 H); 3.38 (dq, 1 H); 3.42 (s, 1 H); 2.98 (m, 2 H); 1.15 (t, 3 H).

Step 4:

A stream of gaseous hydrogen chloride was introduced to the solution of above acid (56.1 g, 0.248 mol) in methanol (450 ml) and benzene (90 ml) at 30-35° C. for 6 h. The reaction mixture was left to stand overnight, diluted with benzene (400 ml) and poured to crushed ice (500 g). The benzene layer was separated and the water layer was extracted with diethyl ether (2×200 m). Collected organic layers were washed with water (4×150 ml), dried over MgSO$_4$, filtrated through silica gel (60 g) and evaporated. The residue vas distilled in vacuo to yield 48.4 g (81.2%) of the title compound. B.p.130° C./200 Pa.

$^1$H NMR (250 MHz, CDCl$_3$): δ 7.18 (m, 2 H); 7.09 (m, 2 H); 3.43 (s, 1 H); 2.94 (m, 2 H); 3.99 (dd, J=5.6 and 7.4 Hz, 1 H); 3.68 (s, 3 H); 3.32 (dqua, J=7.0 and 9.10 Hz, 1 H); 3.59 (dqua, J=7.0 and 9.14 Hz, 1 H); 1.14 (t, J=7.0 Hz, 3 H).

Method B:

Step 1:

A solution of ethyl 2-ethoxycinnamate (53.9 g, 0.267 mol; prepared as described in Justus Liebigs Ann. Chem. 699, 53 (1966)) in ethanol (500 ml) was hydrogenated in the presence of 5% palladium on activated charcoal (5.0 g) at ambient temperature under pressure 10 atm until absorption of hydrogen ceased. The catalyst was filtered off and the filtrate was evaporated to give 52.8 g (97%) of ethyl 2-ethoxy-3-phenyl-propionate as an oil.

Step 2:

Chlorosulfonic acid (110.8 g, 0.95 mol) was cooled to −2-0° C. and then the above ester (52.8 g, 0.238 mol) was added dropwise under stirring at such rate that the temperature of the reaction mixture did not exceed 0° C. (20 min). The mixture was stirred for 1 h, poured on crushed ice (1 kg) and extracted with dichloromethane (300 ml). The organic layer was dried (MgSO$_4$) and evaporated. This gave 36.6 g (43.7%) of crude 3-(4-chlorosulfonyl-phenyl)-2-ethoxypropionic acid ethyl ester, which was used for the next step without purification.

Step 3:

To the mixture of above sulfochloride (36.6 g, 0.114 mol), tin (65.4 g, 0.55 gat) and methanol (60 ml) concentrated hydrochloric acid was added dropwise under vigorous stirring during 20 min. The reaction became exothermic and began to reflux spontaneously.

The reaction mixture was further heated to reflux for 3 hours, then cooled and poured to crushed ice (1 kg). The mixture was extracted with dichloromethane (2×200 ml), organic layer was washed with water (2×80 ml), dried over MgSO$_4$ and evaporated in vacuo. The residue was dissolved in benzene (100 ml), passed trough column of silica gel (Fluka 60, 300 g) and the column was washed with benzene (750 ml). Collected benzene solutions were evaporated and the residue was distilled in vacuo. This afforded 14 g (51%) of the title compound as oil B.p. 136.5-137° C./133 Pa.

Intermediate 3

Ethyl 2,6-diphenyl-4-hydroxyphenoxyacetate

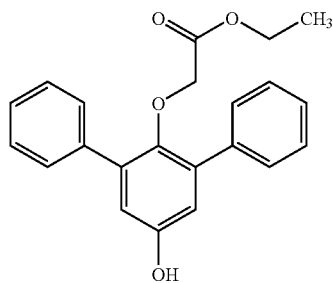

Step 1:

A mixture of 4-acetoxy-2,6-diphenylphenol (6.1 g, 20 mmol; prepared as described in Ber. 101, 2519 (1968)), ethyl bromoacetate (4.0 g, 24 mmol), potassium carbonate (3.3 g, 24 mmol) and 2-butanone (150 ml) was refluxed for 24 h, then filtered and the solvent evaporated. The residue was purified by chromatography on silica gel (120 g, eluent benzene) to give 7.2 g (92%) of oily ethyl 4-acetoxy-2,6-diphenylphenoxyacetate.

$^1$H NMR (300 MHz, CDCl$_3$): δ 7.64 (m, 4 H); 7.37 (m, 6 H); 7.08 (s, 2 H); 3.93 (q, J=7.1, 2 H); 3.79 (s, 2 H); 1.07 (t, J=7.1, 3 H).

Step 2:

The above ester (7.2 g, 18.5 mmol) was dissolved in wet toluene (400 ml) and a catalyst (25 g SiO$_2$ treated with a solution of 2 g 4-toluenesulfonic acid in 10 ml acetone and evaporated in vacuo) was added. The mixture was stirred and heated at 100° C. for 6 h, cooled and filtered through a column of silica gel (50 g). Elution with benzene afforded 3.6 g (56%) of the title compound as white crystals, which were recrystallized from benzene/petroleum ether. M.p. 91-93° C.

$^1$H NMR (250 MHz, CDCl$_3$): δ 1.05 (t, J=7.2 Hz, 3 H); 3.92 (q, J=7.2 Hz, 2 H); 3.73 (s, 2 H); 6.82 (s, 2 H); 7.60 (m, 4 H); 7.35 (m, 6 H).

Intermediate 4

General Procedure E

2-({6-[(2-hydroxy-ethyl)-methyl-amino]-pyridin-2-yl}-methyl-amino)-ethanol

Step A-B:

A mixture of 2,6-dibromopyridine (82.9 g, 0.35 mol) and 2-(methylamino)ethanol (525.8 g, 7 mol) was stirred at 120-140° C. for 20 h. Ethyl acetate (900 ml) and water (600 ml) were added under stirring, organic layer was separated and water layer was extracted with ethyl acetate (5×250 ml). Collected organic layers were washed with brine (80 ml), dried over MgSO$_4$, evaporated to volume 500 ml and passed through a column of silica gel (Fluka 60, 600 g). The column was washed with ethyl acetate (2.5 l), collected solutions were evaporated and dried in vacuo. This afforded 68.6 g (86.2%) of the title compound as an oil.

$^1$H NMR (250 MHz, CDCl$_3$): δ 7.26 (t, J=8.0 Hz, 1 H); 5.79 (d, J=8.1 Hz, 2 H); 4.49 (bs, 2 H); 3.74 (m, 4 H); 3.61 (m, 4 H); 2.97 (s, 6 H).

Intermediate 5

General Procedure A

3-[4'-(3-Hydroxy-propyl)-2,2'-bis-trifluoromethyl-biphenyl-4-yl]-propan-1-ol

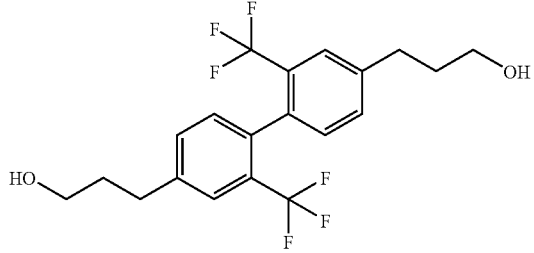

Step 1:

2,2'-Bistrifluoromethyl-4,4'-diaminobiphenyl (42,6 g, 133 mmol; prepared as described in J.Chem.Soc 1951, 3459) was dissolved in acetic acid (300 ml) and concentrated sulphuric acid (50 ml) was added. The resulted suspension was diazotized with NaNO$_2$ (20.2 g, 293 mmol) in 50 ml water at 5° C. for 1 h, then filtered and poured into a solution of KI (220 g, 1.35 mol) in 800 ml water. The mixture was stirred for 3 h, extracted with benzene (300 ml), washed with 5% NaHSO$_3$, dried (MgSO$_4$) and benzene was evaporated in vacuo. The residue was purified by chromatography on silica gel to give 56.5 g (78.4%) of 2,2'-bistrifluoromethyl-4,4'-diiodobiphenyl. M.p. 119-120° C.

Step A-B:

A mixture of the above diiododerivative (56.5 g, 104.3 mmol), palladium(II)acetate (0.7 g, 3.1 mmol), triphenylphosphine (2.1 g, 8 mmol), triethylamine (20 g, 198 mmol) and methyl acrylate (28 g, 325 mmol) in 120 ml dimethylformamide was heated at 110° C. for 5 h. The reaction mixture was poured in water, extracted with benzene, dried (MgSO$_4$) and evaporated in vacuo. The residue was submitted to chromatography on silica gel (benzene/chloroform). First fraction afforded 10.7 g (27.4%) of methyl 3-(2, 2'-bistrifluoromethylbiphenyl-4-yl)acrylate, M.p. 97-98° C. (cyclohexane).

Next fraction yielded 18.3 g (38.3%) of 2,2'-bistrifluoromethylbiphenyl-4,4'-diacrylic acid dimethyl ester. M.p.158-161° C. (cyclohexane).

Step C:

2,2'-Bistrifluoromethylbiphenyl-4,4'-diacrylic acid dimethyl ester (11.5 g, 25.1 mmol) was dissolved in 200 ml polyethylene glycol (PEG 400) and sodium borohydride (6.5 g, 172 mmol) was added gradually during 30 min at 130° C. The mixture was heated at this temperature for 6 h. After cooling water was added, the mixture was extracted with chloroform, dried (MgSO$_4$) and evaporated to give a residue which was submitted to chromatography on silica gel. Elution with ethyl acetate afforded 3.57 g (35%) of the title compound as an oil.

$^1$H NMR (250 MHz, CDCl$_3$): δ 7.55 (d, J=1.4 Hz, 2 H); 7.35 (dd, J=1.4 and 7.7 Hz, 2 H); 7.18 (d, J=7.7 Hz, 2 H); 3.72 (t, J=6.3 Hz, 4 H); 2.83 (t, J=7.8 Hz, 4 H); 1.96 (m, 4 H); 1.65 (bs, 2 H).

Intermediate 6

General Procedure A

3-[4'-(3-Hydroxy-propyl)-3,3'-bis-trifluoromethyl-biphenyl-4-yl]-propan-1-ol

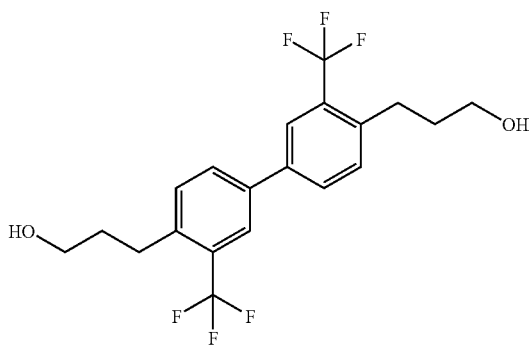

Step C:

3,3'-Bistrifluoromethylbiphenyl-4,4'-diacrylic acid dimethyl ester (12.3 9, 26.8 mmol; prepared the same manner as 2,2'-isomer, intermediate 5, step A-B) was dissolved in 200 ml polyethylene glycol (PEG 400) and sodium borohydride (7.4 g, 196 mmol) was added gradually during 30 min at 130° C. The mixture was heated at this temperature for 6 h, after cooling water was added and the mixture was extracted with chloroform. Chloroform extract was dried (MgSO$_4$) and evaporated to give a residue which was submitted to chromatography on silica gel. Elution with ethyl acetate afforded 1.85 g of the title compound as white crystals.

M.p. 87.5-90° C. (cyclohexane).

$^1$H NMR (300 MHz, CDCl$_3$): δ 7.78 (s, 2 H); 7.63 (d, J=8.2 Hz, 2 H); 7.42 (d,J=8.2 H); 3.75 (t, J=6.4 Hz, 4 H); 2.92 (t, J=7.9 Hz, 4 H); 2.17 (bs, 2 H); 1.93 (m, 4 H).

Intermediate 7

(S)-3-(3-Bromo-4-hydroxy-phenyl)-2-ethoxy-propionic acid isopropyl ester

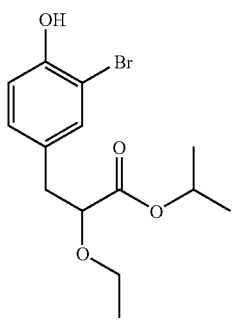

To a solution of (S)-2-ethoxy-3-(4-hydroxy-phenyl)-propionic acid isopropyl ester (7.56 g, 30 mmol) in methylene chloride (75 ml) was added drop wise under nitrogen a solution of Br$_2$ in methylene chloride (30 ml) at room temperature. The reaction was stirred for 60 min after which a saturated aqueous solution of Na$_2$SO$_3$ (50 ml) was added. Methylene chloride (100 ml) was added and the methylene phase was isolated. The organic phase was washed with brine (50 ml), dried and evaporated. The residue was purified by column chromatography using heptane: ethyl acetate (3:1) as eluent. The title compound was isolated in 8.91 g (90%) yield.

$^1$H NMR (300 MHz, CDCl$_3$): δ 7.37 (s, 1H); 7.10 (d, J=8 Hz, 1H); 6.93 (d, J=8 Hz, 1H); 5.05 (m, 1H); 3.93 (t, J=6Hz, 1H); 3.63 (m, 1H); 3.35 (m, 1H); 2.92 (d, J=6 Hz, 2H); 1.30-1.14 (m, 9H).

Intermediate

General Procedure A

3-[7-(3-Hydroxy-propyl)-9H-fluoren-2-yl]-propan-1-ol

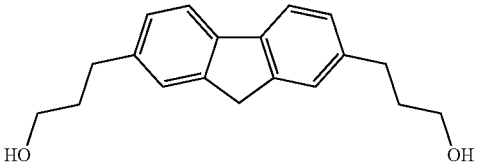

Step A-B:

A mixture of 2,7-dibromofluorene (48.6 g, 0.15 mol, Ber. 53, 1236 (1920) ), palladium(II)acetate (1.0 g, 4.45 mmol), triphenylphosphine (3.0 g, 11.4 mmol), triethylamine (30.3 g, 0.3 mol), methyl acrylate (38.7 9, 0.45 mol) and dimethylformamide (150 ml) was stirred and heated at 110° C. for 7 h. The mixture was poured into water (1000 ml), the resulted solid was filtered off and recrystallized from chloroform to give 36.8 g (73.9%) of fluorene-2,7-diacrylic acid dimethyl ester. M.p. 206-209° C.

$^1$H NMR (300 MHz, DMSO-d$_6$) δ 7.96 (m, 4 H); 7.75 (m, 2 H); 7.73 (d, J=15.9 Hz, 2 H); 6.69 (d, J=15.9 Hz, 2 H); 3.98 (s, 2 H); 3.73 (s, 6 H).

Step C:

A mixture of sodium borohydride (3.7 g, 98 mmol) and lithium chloride (4.2 g, 101 mmol) in ethanol (70 ml) was stirred at 5° C. for 15 min, 9H-fluorene-2,7-diacrylic acid dimethyl ester (5.0 g, 15 mmol) in diglyme (150 ml) was added portionwise at 20-50° C. and the mixture was refluxed for 18 h. Diluted hydrochloric acid was added dropwise after cooling and the mixture was extracted with diethyl ether. Organic layer was separated, dried (MgSO$_4$) and evaporated to give a residue, which was purified by chromatography on silica gel. Elution with ethyl acetate afforded 1.85 g (44%) of the title compound as white crystals.

M.p. 160-180° C.

$^1$H NMR (300 MHz, CDCl$_3$): δ 7.65 (d, J=7.0 Hz, 2 H); 7.35 (s, 2 H); 7.18 d, J=7.7 Hz, 2 H); 3.84 (s, 2 H); 3.71 (t, J=6.3 Hz, 4 H); 2.78 (t, J=7.6 Hz, 4 H); 1.95 (m, 4 H); 1.59 (bs, 2 H).

Intermediate 9

2-(2-{3-[4-(2-Hydroxy-ethyl)-5-methyl-oxazol-2-yl]-phenyl}-5-methyl-oxazol-4-yl)-ethanol

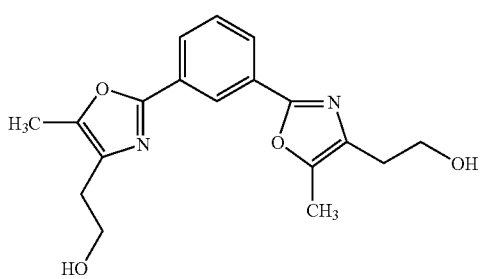

Step 1:

A solution of sodium carbonate (62.8 g, 0.592 mol) in water (1 500 ml) was added to the suspension of 4-benzyl L-aspartate (89.6 g, 0.4 mol) in dioxane (600 ml) and the mixture was stirred until a clear solution was obtained (30 min). A solution of terephtaloyl chloride (40.4 g, 0.199 mol)

in dioxane (400 ml) was added dropwise at ambient temperature during 2 h, the reaction mixture was stirred at ambient temperature for the next 3 h and then left to stand overnight. The solution was washed with diethyl ether (2×500 ml), acidified with 10% hydrochloric acid to pH=2 and the product was extracted with dichloromethane (3×500 ml). Collected filtrates were washed with water (200 ml), brine (100 ml), dried with MgSO$_4$ and evaporated in vacuo to yield 128.8 g (56.7%) of 2-[3-(2-benzyloxycarbonyl-1-carboxy-ethylcarbamoyl)-benzoylamino]-succinic acid 4-benzyl ester as a white solid.

$^1$H NMR (250 MHz, DMSO-d$_6$): δ 9.03 (d, J=8.0 Hz, 2 H); 8.37 (m, 1 H); 8.00 (dd, J=1.6 and 7.8 Hz, 2 H); 7.63 (m); 5.14 (s, 4 H); 4.89 (m, 2 H); 3.05 (dd, J=5.7 and 16.2 Hz, 2 H); 2.9 (dd, J=8.4 and 16.2 Hz, 2 H).

Step 2:

Acetanhydride (600 ml) was added dropwise to the solution of above diester (110.5 g, 0.191 mol) in pyridine (600 ml) during 1.5 h and the reaction mixture was stirred at 95° C. for 2 h. The dark solution was cooled to 80° C., water (325 ml) was added dropwise at such a rate that the mixture refluxed vigorously (30 min), warmed to reflux for the next 30 min and left to stand overnight. The reaction mixture was acidified with 10% hydrochloric acid (1800 ml), extracted with ethyl acetate (1000 ml, 2×500 ml), collected extracts were washed with water (200 ml), dried MgSO$_4$ and evaporated in vacuo to yield 97.1 g (88.8%) of crude 3-[3-(1-benzyloxycarbonylmethyl-2-oxo-propylcarbamoyl)-benzoylamino]-4-oxo-pentanoic acid benzyl ester as an oil which was used directly to next step.

Step 3:

The above compound (95.0 g, 0.166 mol) was dissolved in toluene (1000 ml) phosphorus oxychloride (320 ml) was added and the mixture was stirred at reflux temperature for 4 h. After standing overnight the mixture was poured on ice (3 kg) and neutralized with solid potassium carbonate (1.6 kg) under stirring. The mixture was extracted with diethyl ether (3×600 ml), the extracts were washed with brine (2×200 ml), dried (MgSO$_4$) and evaporated in vacuo. The residue (106 g) was chromatographed on the column of SiO$_2$ (Fluka 60, 1000 g).

Elution with benzene gave by-products (10.5 g), elution with benzene/ethyl acetate (9:1) afforded 22.8 g (25.6%) of {2-[3-(4-benzyloxycarbonylmethyl-5-methyl-oxazol-2-yl)-phenyl]-5-methyl-oxazol-4-yl}-acetic acid benzyl ester, m.p. 98-100° C.

Step 4:

A solution of the above diester (21.4 g, 39.8 mmol) in tetrahydrofuran (800 ml) was added dropwise to a suspension of lithium aluminum hydride (3.0 g, 79.7 mmol) in diethyl ether (200 ml) at 0° C. during 60 min. The mixture was stirred 30 min at the same temperature, 4 h at ambient temperature and then left to stand overnight. The reaction mixture was decomposed by successive addling water (3 ml), 15% solution of sodium hydroxide (3 ml) and water (10 ml). The suspension was stirred at ambient temperature for 3 h, the solid was filtered off, washed with tetrahydrofuran (100 ml) and ethyl acetate (300 ml). The collected filtrates were dried (MgSO$_4$) and evaporated. The residue (23 g) was submitted to chromatography (silica gel Fluka 60, 500 g). Elution with ethyl acetate and ethanol (95:5) gave the title product (10.1 g, 77.2%), m.p. 134-135° C.

$^1$H NMR (250 MHz, DMSO-d$_6$): δ 8.41 (s, 1 H); 7.98 (d, J=7.8 Hz, 2 H); 7.67 (t, J=7.7 Hz, 1 H); 4.68 (t, J=5.4 Hz, 2 H); 3.67 (q, J=6.6 Hz, 4 H); 2.64 (t, J=6.7 Hz, 4 H); 2.38 )s, 6 H).

Intermediate 10

2-(2-{4'-[4-(2-Hydroxy-ethyl)-5-methyl-oxazol-2-yl]-biphenyl-4-yl}-5-methyl-oxazol-4-yl)-ethanol

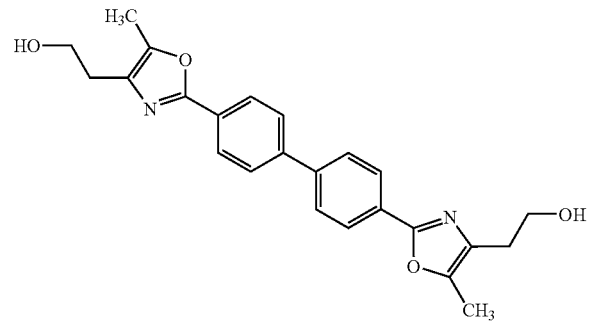

Step 1:

L-Aspartic acid 4-benzylester (78.1 g, 0.35 mol) was suspended in dioxane (1000 ml), the solution of sodium carbonate (56 g, 0.52 mol) in water (1200 ml) and the mixture was stirred for 1 h. Biphenyl-4,4'-dicarbonyl dichloride (48.9 g, 0.175 mol) was added portion-wise to this mixture during 2 h and the reaction mixture was stirred at ambient temperature for 3 h. Water was added (350 ml), and the mixture was left to stand overnight and then washed with diethyl ether (3×350 ml). The water layer was acidified with 10% hydrochloric acid, the precipitated solid was filtered, washed with water and dried. Yield of crude 2-{[4'-(2-benzyloxycarbonyl-1-carboxy-ethylcarbamoyl)-biphenyl-4-carbonyl]-amino}-succinic acid 4-benzyl ester was 69.5 g (60.8%). M.p. 204-207° C.

$^1$H NMR (250 MHz, DMSO-d$_6$): δ 8.97 (d, 2 H); 7.99 (m, 4 H); 7.90 (m, 4 H); 7.36 (m, 10 H); 5.15 (s, 4 H); 4.90 (m, 2 H); 3.20 (bs); 2.99 (m, Σ 4 H).

Step 2:

The above compound (68.9 g, 0.145 mol) was dissolved in absolute pyridine (300 ml) and then acetic anhydride (300 ml) was added drop-wise. The reaction mixture was warmed up to 95° C., stirred for 3.5 h, and cooled to 80° C. Water (160 ml) was added (temperature between 100-120° C.) and then the reaction mixture was stirred at 90° C. for 1 h and left to stand overnight. Hydrochloric acid (10%, 900 ml) was added under ice cooling, and the precipitated solid was filtered off and washed with water (3×250 ml). This afforded, after drying on air, 58.5 g (85.5%) crude 3-{[4'-(1-benzyloxycarbonylmethyl-2-oxo-propylcarbamoyl)-biphenyl-4-carbonyl]-amino}-4-oxo-pentanoic acid benzyl ester. M.p.165-168° C.

$^1$H NMR (250 MHz, DMSO-d$_6$): δ 9.25 (d, 2 H); 8.03 (m, 4 H); 7.91 (m, 4 H); 7.35 (m, 10 H); 5.14 (s, 4 H); 4.82 (m, 2 H); 3.12 and 3.78 (m, Σ 4 H); 2.20 (s, 6 H).

Step 3:

The mixture of above compound (57.4 g, 0.123 mol), toluene (600 ml) and phosphorus oxychloride (160 ml) was stirred at reflux temperature for 4 h. The mixture was cooled to 50° C., poured on ice (1500 g) and neutralized with solid potassium carbonate (600 g) under stirring. The mixture was extracted with diethyl ether (3×500 ml) and chloroform (3×200), the extracts were combined, powdery polymers were filtered off and the filtrate was washed with water (100 ml), brine (80 ml), dried (MgSO$_4$) and evaporated in vacuo. The residue (41 g) was chromatographed on the column of SiO$_2$ (Fluka 60, 800 g). Elution with benzene/ethyl acetate (9:1) afforded 6.2 g (12.5%) of {2-[4'-(4-benzyloxycarbonylmethyl-5-methyl-oxazol-2-yl)-biphenyl-4-yl]-5-methyl-oxazol-4-yl}-acetic acid benzyl ester, m.p.162-168° C.

$^1$H NMR (300 MHz, DMSO-d$_6$): δ 7.98 (m, 4 H); 7.88 (m, 4 H); 7.35 (m, 10 H); 5.14 (s, 4 H); 3.71 (s, 4 H); 2.36 (s, 6 H).

Step 4:

The solution of above diester (6.0 g, 14.8 mmol) in tetrahydrofuran (500 ml) was added drop-wise to a suspension of lithium aluminum hydride (1.12 g, 29.7 mmol) in diethyl ether (150 ml) at 5° C. during 60 min. The mixture was stirred the next 2 h at the same temperature, and 2 h at ambient temperature. The reaction mixture was decomposed by successive addling water (1.1 ml), 15% solution of sodium hydroxide (1.1 ml) and water (3.5 ml). The suspension was stirred at ambient temperature for 1.5 h, the solid was filtered off, and washed with tetrahydrofuran (50 ml) and chloroform (100 ml). The collected filtrates were dried (MgSO$_4$) and evaporated. The residue (2.9 g) was submitted to chromatography (silica gel Fluka 60, 200 g). Elution with ethyl acetate and ethanol (95:5 and then 40:60) gave the title compound (0.95 g, 15.8%), m.p. 134-135° C.

$^1$H NMR (250 MHz, DMSO-d$_6$): δ 8.01 (m, 4 H); 7.87 (m, 4 H); 4.70 (bt, 2 H); 3.69 (m, 4 H); 2.65 (t, J=7.7 Hz, 4 H); 2.36 (s, 6 H).

Intermediate 11

(4-Mercapto-2-trifluoromethyl-phenoxy)-acetic acid ethyl ester

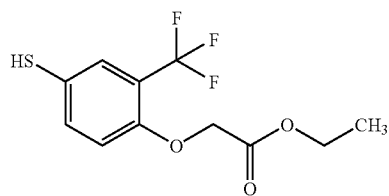

Step 1:

A mixture of 2-trifluoromethyl-4-nitrophenol (73.4 g, 0.354 mol), ethyl bromoacetate (65.2 g, 0.39 mol), potassium carbonate (58.7 g, 0.425 mol) and 2-butanone (400 mL) was refluxed under stirring for 10 h. The solid was filtered off, the filtrate was evaporated and the residue was fractionated yielding 97.8 g (95%) of 2-trifluromethyl-4-nitrophenoxyacetic acid ethyl ester, b.p. 126° C./40 Pa.

Step 2:

The above ester (97.8 g, 0.334 mol) was dissolved in ethanol (450 mL), 5%Pd/C (6.0 g) was added and the mixture was hydrogenated at normal pressure and temperature for 3 h. The catalyst was removed by filtration, ethanol was evaporated and the residual 4-amino-2-trifluoromethyl-phenoxyacetic acid ethyl ester (87.6 g, 0.334 mol) was added to the mixture of conc. hydrochloric acid (65 mL) and water (170 mL). The mixture was cooled to 5° C. and then a solution of sodium nitrite (23.0 g, 0.334 mol) in water (90 mL) was added drop-wise together with cracked ice to keep the temperature below 5° C. This takes about 5 min. In another beaker, 100 mL water was warmed to reflux and then Na$_2$S.3H$_2$O (46.5 g, 0.367 mol) and powdered sulfur (11.7 g, 0.367 mol) were dissolved by heating and stirring. A solution of sodium hydroxide (13.3 g, 0.334) mol in water (30 mL) was then added and the mixture was cooled below 5° C. The solution of diazonium salt was added along with ice to prevent the temperature rising. When addition was complete, the mixture was allowed to warm up to laboratory temperature overnight and filtered. The filtrate was made acidic with conc. hydrochloric acid and extracted with ethyl acetate. To remove the excess sulfur, this solution was extracted with a solution of sodium carbonate, filtered, acidified and extracted again with ethyl acetate. The extract was dried (MgSO$_4$) and the solvent evaporated.

The residual 4,4'-dithiobis-(2-trifluoromethylphenoxyacetic acid ) was refluxed with ethanol (1500 mL) and conc. sulphuric acid (30 mL) for 8 h and then ethanol was evaporated. The residue was dissolved in benzene and the solution was washed with water and the solvent evaporated. The residue was purified by chromatography on silica gel (250 g, benzene/chloroform) yielding 42.0 g (45%) of diethyl ester, m.p. 118-120° C.

Step 3:

The above diethyl ester (20.0 g, 358 mmol) was dissolved in dimethylacetamide (100 mL), sodium borohydride (3.5 g, 926 mmol) was added portionwise at 5° C. and the mixture was stirred for 60 min. Acetone (20 mL) and benzene (300 mL) were added, the mixture was washed with water and the organic layer was evaporated. The residue was fractionated at reduced pressure to yield the title compound (7.5 g, 37%), b.p. 72° C./5 Pa. A considerable amount of high-boiling material remained (starting diethyl ester).

R$_F$ (SiO$_2$, chloroform/methanol 9:1): 0.69.

$^1$H NMR spectrum (300 MHz, CDCl$_3$): 7.56 (d, J=2.2 Hz, 1 H); 7.41 (dd, J=2.2 and 8.5 Hz, 1 H); 6.78 (d, J=8.5 Hz, 1 H); 4.68 (s, 2 H); 4.25 (q, J=7.15 Hz, 2 H); 3.46 (s, 1 H); 1.27 (t, J=7.15 Hz, 3 H).

Intermediate 12

(2-Chloro-4-mercapto-phenoxy)-acetic acid ethyl ester

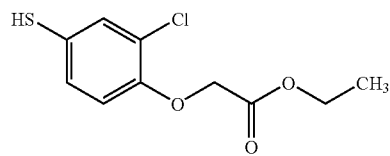

Step 1:

A mixture of 2-chloro-4-nitrophenol (63.6 g, 0.367 mol), ethyl bromoacetate (67.0 g, 0.4 mol), potassium carbonate (60.7 g, 0.44 mol) and 2-butanone (400 mL) was refluxed under stirring for 10 h, then filtered and the solvent was evaporated. The residue was fractionated yielding 61.1 g (64%) of 2-chloro-4-nitrophenoxyacetic acid ethyl ester, b.p. 150° C./40 Pa.

Step 2:

The above ester (61.1 g, 0.236 mol) was dissolved in ethanol (300 mL), 5% Pd/C (4.0 g) was added and the mixture was hydrogenated at atmospheric pressure and laboratory temperature for 3 h. The catalyst was removed by filtration, ethanol was evaporated and the residual 4-amino-2-chloro-phenoxyacetic acid ethyl ester (54.1 g, 0.236 mol) was added to the mixture of conc. hydrochloric acid (50 mL) and water (125 mL) and the mixture was cooled to 5° C. A solution of sodium nitrite (16.3 g, 0.236 mol) in 70 mL water was added dropwise together with cracked ice to keep the temperature below 5° C. This takes about 5 min.

In another beaker, water (75 mL) was warmed to reflux and Na$_2$S.3H$_2$O (33.0 g, 0.26 mol) and powdered sulfur (8.3 g, 0.26 mol) were added and dissolved by heating and stirring. A solution of sodium hydroxide (9.5 g, 0.236) mol in water (25 mL) was then added and the mixture was cooled below 5° C. The solution of diazonium salt was added to this solution along with ice to prevent the temperature rising. When addition was complete, the mixture was allowed to warm up to room temperature overnight and filtered. The filtrate was made acidic with conc. hydrochloric acid and extracted with ethyl acetate. To remove the excess sulfur, this solution was extracted with a solution of sodium carbonate, filtered, acidified and extracted again with ethyl acetate. The extract was dried (MgSO$_4$) and the solvent evaporated.

The residual 4,4'-dithiobis-(2-chlorophenoxyacetic acid) (41.5 g) was refluxed with ethanol (1000 mL) and sulphuric acid (25 mL) for 8 h and ethanol was evaporated. Benzene was added, the mixture washed with water and the solvent was evaporated. The residue was purified by chromatography on silica gel (250 g, benzene/chloroform) yielding 17.7 g (40%) of 2-chloro-4-(3-chloro-4-ethoxycarbonylmethoxyphenyldisulfanyl)-phenoxy]-acetic acid diethyl ester.

Step 3:

The above diethyl ester (13.4 g, 273 mmol) was dissolved in 70 mL dimethylacetamide, sodium borohydride (3.1 g, 820 mmol) was added portionwise at 5° C. and the mixture was stirred for 30 min. Acetone (15 mL) and benzene (200 mL) were added, The solution was washed with water, the organic layer was evaporated and the residue fractionated at reduced pressure. This afforded (2.5 g, 19%) of the title compound, b.p. 120° C./10 Pa. A considerable amount of high-boiling material remained (starting diethyl ester).

R$_F$ (SiO$_2$, chloroform/methanol 9:1): 0.73.

$^1$H NMR spectrum (300 MHz, CDCl$_3$): 7.35 (d, J=2.2 Hz, 1 H); 7.12 (dd, J=2.2 and 8.5 Hz, 1 H); 6.72 (d, J=8.5 Hz, 1 H); 4.65 (s, 2 H); 4.24 (q, J=7.15 Hz, 2 H); 3.41 (s, 1 H); 1.27 (t, J=7.15 Hz, 3 H).

Intermediate 13

(2-Chloro-4-mercapto-phenylsulfanyl)-acetic acid ethyl ester

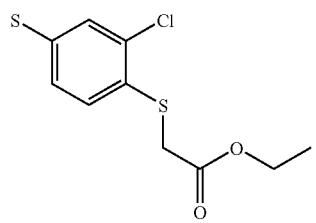

Step 1:

4-Amino-2-chloro-phenylthioacetic acid hydrate (109.3 g, 0.49 mol, prepared according FR Pat. 1489916) was added to the mixture of conc. hydrochloric acid (100 mL) and water (200 mL) and the mixture was cooled to 5° C. A solution of sodium nitrite (34.5 g, 0.5 mol) in water (150 mL) was added dropwise together with cracked ice to keep the temperature below 5° C. This takes about 5 min. In another beaker, 200 mL water was heated to boil and Na$_2$S.9H$_2$O (72.6 g, 0.55 mol) and powdered sulfur (17.0 g, 0.53 mol) were dissolved by heating and stirring. A solution of sodium hydroxide (20 g, 0.5) mol in water (50 mL) was then added and the mixture cooled below 5° C. The solution of diazonium salt was added to this solution along with ice to prevent the temperature rising. When addition was complete, the mixture was allowed to warm up to room temperature overnight and filtered. The filtrate was made acidic with conc. hydrochloric acid and extracted with ethyl acetate. To remove the excess sulfur, this solution was extracted with a solution of sodium carbonate, filtered, acidified and extracted again with ethyl acetate. The extract was dried (MgSO$_4$) and the solvent was evaporated. The mixture of this residual crude 4,4'-dithiobis-(2-chlorophenylthioacetic acid) (49 g), ethanol (500 mL) and conc. sulphuric acid (30 mL) was refluxed for 8 h. Ethanol was evaporated, the residue was dissolved in diethyl ether and the solution was washed with water, 5% solution of sodium hydrogen carbonate and the solvent was evaporated in vacuo. The residue was purified by chromatography on silica gel (250 g, benzene/chloroform). Yield of diethyl ester was 29 g (23%).

Intermediate 14

General Procedure A

3-[4'-(3-Hydroxy-propyl)-biphenyl-4-yl]-propan-1-ol

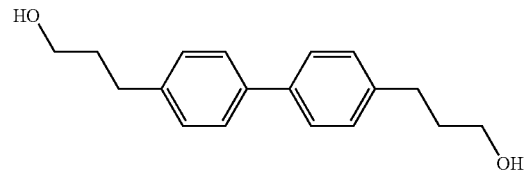

Step A-B:

A mixture of 3,3'-dichloro-4,4'-diiodobiphenyl (44.5 g, 95 mmol; prepared according to J.Chem.Soc. 85, 7 (1904)), triphenylphosphine (2.0 g, 7.6 mmol), palladium(II)acetate (0.67 g, 3 mmol), methyl acrylate (25.8 g, 300 mmol) and triethylamine (18.0 g, 178 mmol) in N,N-dimethylformamide (90 mL) was stirred and heated to 110° C. for 9 h and then allowed to stand overnight. The crystals of contaminated 3,3'-dichlorobiphenyl-4,4'-diacrylic acid di-methyl ester were filtered, washed with water and benzene and dried.

Crude yield: 22.5 g.

Step C:

The mixture of the above crude diester (22.5 g), dioxane (300 mL) and 5% aqueous solution of sodium hydroxide (150 mL) was refluxed for 4 h. Dioxane was evaporated and the residue was dissolved in water (900 mL). Palladium (5% on charcoal, 4.3 g) was added and the mixture was hydrogenated at atmospheric pressure and ambient temperature for 6 h. The catalyst was filtered off, contaminated biphenyl-4,4'-dipropionic acid was precipitated by the addition of conc. hydrochloric acid, filtered, washed with water and dried.

Crude yield: 15.0 g.

The above crude acid (14.1 g) was dissolved in tetrahydrofuran (150 mL), sodium borohydride (4.35 g, 115 mmol) was added portionwise during 30 min followed by dropwise addition of boron trifluoride etherate (22.0 g, 155 mmol). The mixture was refluxed for 8 h, quenched with 5% aqueous solution of sodium hydroxide (100 mL) and extracted with ether (4×25 mL). The organic layer was dried with anhydrous potassium carbonate, evaporated and the residue was crystallized from methanol giving pure 4,4'-biphenyidipropanol.

Yield: 5.1 g (20%, calculated on 3,3'-dichloro-4,4'-diiodobiphenyl).

M.p. 154-158° C.

$^1$H NMR spectrum (CDCl$_3$) 7.51 (d, J=8.1 Hz, 4 H); 7.26 (d, J=8.1 Hz, 4 H); 3.71 (t, J=6.5 Hz, 4 H); 2.75 (t, J=8.0 Hz, 4 H); 1.95 (m, 4 H).

Intermediate 15

(4-Mercapto-2-methoxyphenoxy)acetic acid methyl ester

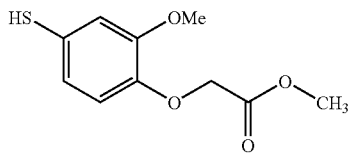

Step 1:

To a solution of (2-methoxy-4-nitrophenoxy)acetic acid ethyl ester (107.0 g, 0.42 mol, prepared as described in J.Chem.Soc. 1955, 3681) in ethanol (800 mL) a slurry of 5% palladium (5.0 g) on carbon in ethanol (50 mL) was added. The mixture was hydrogenated in a Parr apparatus for 3 h. Removal of the catalyst and solvent left oily crude (4-amino-2-methoxyphenoxy)acetic acid ethyl ester.

Yield: 93.7 g, 99%.

Step 2:

The above crude ester (91.7 g, 0.405 mol) was added to a mixture of conc. hydrochloric acid (78 mL) and water (195 mL) and the resulting mixture was cooled to 5° C. A solution of sodium nitrite (27.0 g, 0.391 mol) in water (100 mL) was added dropwise together with cracked ice to keep the reaction temperature below 5° C. (5 min). The solution of diazo compound was stirred for 30 min and then added dropwise to a solution of potassium ethyl xanthogenate (90 g, 0.56 mol) in water (100 mL) maintaining the reaction temperature between 45 and 50° C. The mixture was stirred for 2 h, cooled and extracted with ether (4×50 mL). The combined organic layers were evaporated and the residue dissolved in ethanol (300 mL). Potassium hydroxide pellets (100 g, 1.79 mol) were added to this warm solution so quickly to maintain reflux which was then continued for 8 h. Ethanol was evaporated, the residue dissolved in water, made acidic with conc. hydrochloric acid and extracted with ethyl acetate (3×75 mL). The collected extracts were dried with anhydrous magnesium sulfate and evaporated in vacuo. The obtained residue was crystallized from chloroform yielding hemihydrate of 4-mercapto-2-methoxyphenoxyacetic acid.

Yield: 22.5 g (25%).

M.p. 138-140° C.

$^1$H NMR spectrum (CDCl$_3$):6.86 (m, 2 H); 6.78 (d, J=8.8 Hz, 1 H); 4.66 (s, 2 H); 3.87 (s, 3 H); 3.45 (s, 1 H).

Step 3:

A solution of the above acid (20 g, 0.09 mol) methanol (200 mL) was saturated with gaseous hydrogen chloride for 1 h. The resulting mixture was refluxed for 8 h and subsequently evaporated in vacuo. Ether (100 mL) was added and the solution was washed with water (2×20 mL) and 5% aqueous solution of sodium hydrogen carbonate (2×20 mL). The collected organic layers were dried with anhydrous sodium sulfate, evaporated in vacuo and the residue was distilled at reduced pressure yielding the title compound.

Yield: 10 g (49%)

R$_F$ (SiO$_2$, hexane/ethyl acetate, 70:30) 0.45.

$^1$H NMR spectrum (300 MHz, CDCl$_3$): 6.83 (m, 2 H); 6.71 (d, J=8.0 Hz, 1 H); 4.65 (s, 2 H); 3.85 (s, 3 H); 3.78 (s, 3 H); 3.42 (s, 1 H).

Intermediate 16

3-{4-[4-(3-Hydroxy-propyl)-2-trifluoromethyl-phenylsulfanyl]-3-trifluoromethyl-phenyl}-propan-1-ol

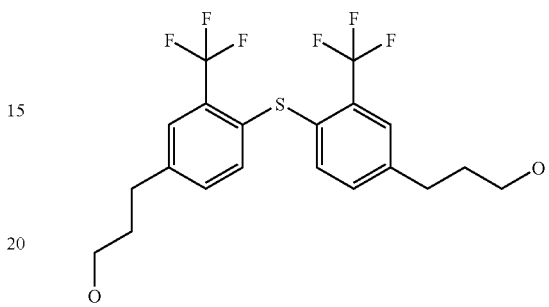

Step 1:

A solution of sodium sulfide nonahydrate (300 g, 1.25 mol) in water (300 mL) was added to the mixture of 4-chloro-3-trifluoromethylnitrobenzene (113 g, 0.5 mol) and 250 mL water dropwise at 100° C. The reaction mixture was heated under stirring for next 6 h. The oily phase was decanted, dissolved in benzene and the solvent evaporated in vacuo to yield 75.6 oily residue. This oil (66.4 g) was dissolved in ethanol (300 mL), hydrazine hydrate (25 g), activated charcoal (5 g) and ferric chloride hexahydrate (1.0 g) were added and the mixture was refluxed for 32 h, then filtered and evaporated. The residue was submitted to chromatography on silica gel (Fluka 60, 400 g). An elution with benzene afforded 22.6 g of 4-amino-2-trifluoromethylbenzenethiol, m.p. 35-36.5° C.

$^1$H NMR spectrum (300 MHz, CDCl$_3$): 7.22 (d, J=8.5 Hz, 1 H); 6.95 (d, J=2.75 Hz, 1 H); 6.72 (dd, J=2.75 and 8.5 Hz, 1 H); 3.83 (bs, 3 H).

Continuing of chromatography with chloroform afforded 35.4 g of 4,4'-diamino-2,2'-bis(trifluoromethyl)diphenylsulfide, m.p. 65-70° C.

$^1$H NMR spectrum (300 MHz, CDCl$_3$): 7.05 (m, 4 H); 6.72 (d, J=8.5 Hz, 2 H); 4.25 (bs, 4 H).

Step 2:

A solution of sodium nitrite (12.2 g, 177 mmol) in 30 mL water was added dropwise with stirring to a mixture of the above sulfide (33.5 g, 95 mmol), conc. hydrochloric acid (100 mL) and cracked ice (150 g) at 0° C. The resulting cold bis-diazonium salt solution was added slowly to a stirred solution of potassium iodide (90 g, 338 mmol) in 300 mL water. Benzene (300 mL) was added and after stirring the mixture at ambient temperature for 3 h the layers were separated. The organic layer was washed with 5% sodium hydrogen sulfite, dried and evaporated to yield 50 g (91%) of 4,4'-diiodo-2,2'-bis(trifluoromethyl)diphenylsulfide.

M.p. 75-87° C. This product was used in the next step without purification.

General Procedure A:

Step A-B:

A mixture of the above sulfide (49.7 g, 86.6 mmol), triphenylphosphine (1.8 g, 6.9 mmol), palladium(II)acetate (0.6 g, 2.67 mmol), methyl acrylate (22.1 g, 257 mmol) and triethylamine (17 g, 168 mmol) in 80 mL dimethylformamide was stirred and heated to 110° C. for 9 h. After standing overnight water and benzene were added, the organic layer was separated, washed with water, evaporated and the residue was purified by chromatography on silica gel (Fluka, 300 g, benzene and chloroform). The yield of 3-{4-[4-(2-carboxyvinyl)-2-trifluoromethyl-phenylsulfanyl]-3-trifluoromethyl-phenyl}-acrylic acid dimethyl ester was 20.1 g (47%).

M.p. 169-174° C.

$^1$H NMR spectrum (300 MHz, CDCl$_3$): 7.86 (d, J=1.6 Hz, 2 H); 7.65 (d, J=16.2 Hz, 2 H); 7.54 (dd, J=1.6 and 8.25 Hz, 2 H); 7.24 (d, J=8.25 Hz, 2 H); 6.48 (d, J=16.2 Hz, 2 H); 3.82 (s, 6 H).

Step C:

Step 1:

The mixture of the above ester (14.1 g, 28.8 mmol) in 100 mL methanol and 20% sodium hydroxide (25 mL) was heated to reflux and then stirred without heating for 4 h. Methanol was evaporated, the residue was dissolved in water, acidified with conc. hydrochloric acid and the precipitate filtered and dried. The yield of 3-{4-[4-(2-carboxyvinyl)-2-trifluoromethyl-phenylsulfanyl]-3-trifluoromethyl-phenyl}-acrylic acid was 13.3 g (quant.).

Step 3:

The above acid (4.4 g, 9.4 mmol)) was dissolved in 50 mL tetrahydrofuran, sodium borohydride (0.80 g, 21.1 mmol) was added portionwise during 30 min and then boron trifluoride etherate (4.9 g, 34.5 mmol) dropwise. The mixture was diluted with diethyl ether (100 mL) and then stirred at laboratory temperature for 48 h. The reaction mixture was quenched with 10% hydrochloric acid, the organic layer was dried (K$_2$CO$_3$) and evaporated to give 4.1 g (99%) of 3-{4-[4-(3-hydroxy-propyl)-2-trifluoromethyl-phenylsulfanyl]-3-trifluoromethyl-phenyl}-propan-1-ol.

M.p. 96-102° C.

$^1$H NMR spectrum (300 MHz, CDCl$_3$): 7.55 (s, 2 H); 7.24 (dd, 2 H); 7.13 (d, J=8.0 Hz, 2 H); 3.68 (t, 4 H); 2.75 (t, J=7.8 Hz, 4 H); 1.89 (m, 4 H); 1.60 (bs,1 H); 1.38 (bs, 1 H).

Example 1

General Procedure E

2-Ethoxy-3-[4-(2-{[6-({2-[4-(2-ethoxy-2-methoxy-carbonyl-ethyl)-phenylsulfanyl]-ethyl}-methyl-amino)-pyridin-2-yl]-methyl-amino}-ethylsulfanyl)-phenyl]-propionic acid methyl ester

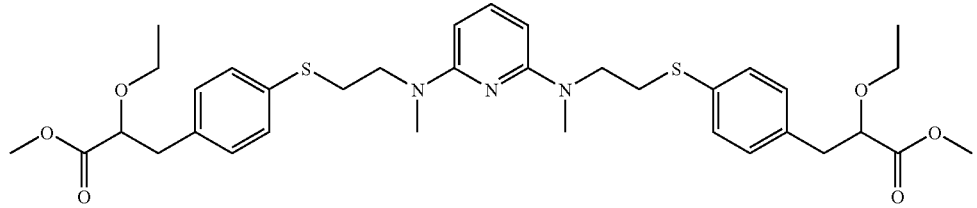

M.p. 227-247° C.

$^1$H NMR spectrum (300 MHz, DMSO): 12.25 (bs, 2 H); 8.17 (s, 2 H); 7.96 (d, J=8.0 Hz, 2 H); 7.66 (d, J=16.2 Hz, 2 H); 7.28 (d, J=8.0 Hz, 2 H); 6.68 (d, J=16.2 Hz, 2 H).

Step 2:

The above acid (7.2 g, 156 mmol) was dissolved in 200 mL ethanol, hydrazine hydrate (40 mL) was added and then a solution of sodium (meta)periodate (15.0 g, 70 mmol) in 80 mL water was added dropwise at room temperature during 5 h. The mixture was filtered, diluted with water, acidified with conc. hydrochloric acid and extracted with chloroform. The organic extract was dried (MgSO$_4$), evaporated and the residue was purified by chromatography on silica gel (Fluka 60, 85 g, chloroform/diethyl ether) yielding 4.5 g (62%) of 3-{4-[4-(2-carboxy-ethyl)-2-trifluoromethyl-phenylsulfanyl]-3-trifluoromethyl-phenyl}-propionic acid.

M.p. 175-178° C.

$^1$H NMR spectrum (300 MHz, DMSO-d$_6$): 12.20 (s, 2 H); 7.71 (s, 2 H); 7.48 (d, J=8.2 Hz, 2 H); 7.13 (d, J=8.2 Hz, 2 H); 2.87 (t, J=7.4 Hz, 4 H); 2.56 (t, J=7.4 Hz, 4 H).

Step C-D:

To a stirred solution of 2-({6-[(2-hydroxy-ethyl)-methyl-amino]-pyridin-2-yl}-methyl-amino)-ethanol (intermediate 4) (38 mg, 0.17 mmol) in dry THF (3.5 ml) was added at 0° C. under nitrogen tributylphosphine (100 mg, 0.50 mmol) and 2-ethoxy-3-(4-mercapto-phenyl)-propionic acid methyl ester (intermediate 2) (98 mg, 0.41 mmol). The reaction mixture was stirred for 15 min. and azodicarboxylic dipiperidine (126 mg, 0.50 mmol) was added. The reaction was stirred for 6 h, after which water (5 ml) was added and the mixture was extracted with methylene chloride (3×20 ml). The combined organic phases were dried (MgSO$_4$), filtered and evaporated. The crude product was purified on column chromatograph using heptanes: ethyl acetate (3:1) as eluent to give the title compound in 85 mg (75%) yield.

$^1$H NMR (300 MHz, CDCl$_3$): δ 7.3-7.2 (m, 5H); 7.15 (d, J=8 Hz, 4H); 5.72 (d, J=8 Hz, 2H); 4.01 (t, J=6 Hz, 2H); 3.71 (s, 6H); 3.7-3.55 (m, 6H); 3.40-3.27 (m, 2H); 3.10 (t, J=7 Hz, 4H); 2.98 (m, 4H); 2.95 (s, 6H); 1.15 (t, J=6 Hz, 6H).

Example 2

General Procedure D

3-[4-(2-{[6-({2-[4-(2-Carboxy-2-ethoxy-ethyl)-2-chloro-phenylsulfanyl]-ethyl}-methyl-amino)-pyridin-2-yl]-methyl-amino}-ethylsulfanyl)-3-chloro-phenyl]-2-ethoxy-propionic acid

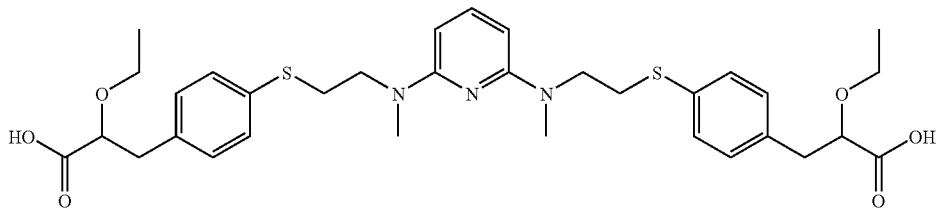

Step A:

2-Ethoxy-3-[4-(2-{[6-({2-[4-(2-ethoxy-2-methoxycarbonyl-ethyl)-phenylsulfanyl]-ethyl}-methyl-amino)-pyridin-2-yl]-methyl-amino}-ethylsulfanyl)-phenyl]-propionic acid methyl ester (example 1) (85 mg, 0.13 mmol) was dissolved in ethanol (5 ml) by heating to 60° C. 1N aqueous NaOH was added to the warm solution and the reaction mixture was stirred at 60° C. for 5 h. The reaction mixture was evaporated and the residue suspended in water (2 ml). The suspension was extracted with methylene chloride (2×25 ml), and the combined organic phases were dried, filtered and evaporated to give the title compound in 71 mg (86%) yield.

$^1$H NMR (300 MHz, CDCl$_3$): δ 7.26 (m, 5H); 7.15 (d, J=8 Hz, 4H); 5.73 (d, J=8 Hz, 2H); 4.05 (m, 2H); 3.74-3.55 (m, 6H); 3.46-3.34 (m, 2H); 3.12-2.94 (m, 8H); 2.93 (s, 6H); 1.15 (t, J=6 Hz, 6H).

Example 3

General Procedure E (5'-{2-[(6-{[2-(2'-Ethoxycarbonylmethoxy-[1,1';3',1"]terphenyl-5'-yloxy)-ethyl]-methyl-amino}-pyridin-2-yl)-methyl-amino]-ethoxy}-[1,1';3',1"]terphenyl-2'-yloxy)-acetic acid ethyl ester

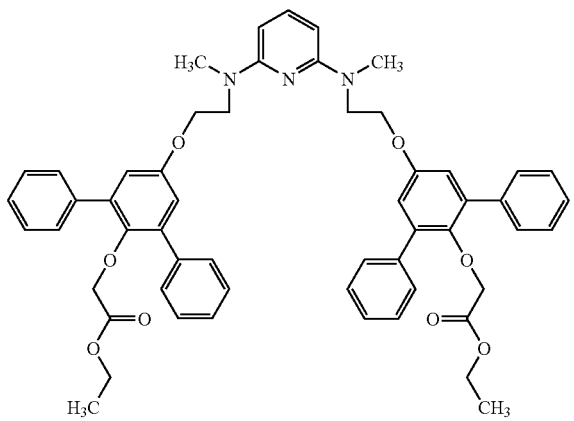

Step C-D:

Was synthesized as described under example 1, step C-D, using ethyl 2,6-diphenyl-4-hydroxyphenoxyacetate (intermediate 3) (143 mg, 0.41 mmol) in stead of 2-ethoxy-3-(4-mercapto-phenyl)-propionic acid methyl ester giving the title compound in 26 mg (17%) yield.

$^1$H NMR (300 MHz, CDCl$_3$): δ 7.58 (m, 8H); 7.43-7.27 (m, 13H); 6.85 (s, 4H); 5.83 (d, J=8 Hz, 2H); 4.20 (t, J=6 Hz, 4H); 5.93 (m, 8H); 5.73 (s, 4H); 3.07 (s, 6H); 1.06 (t, J=7 Hz).

Example 4

General Procedure D (5'-{2-[(6-{[2-(2'-Carboxymethoxy-[1,1';3',1"]terphenyl-5'-yloxy)-ethyl]-methyl-amino}-pyridin-2-yl)-methyl-amino]-ethoxy}-[1,1';3',1"]terphenyl-2'-yloxy)-acetic acid

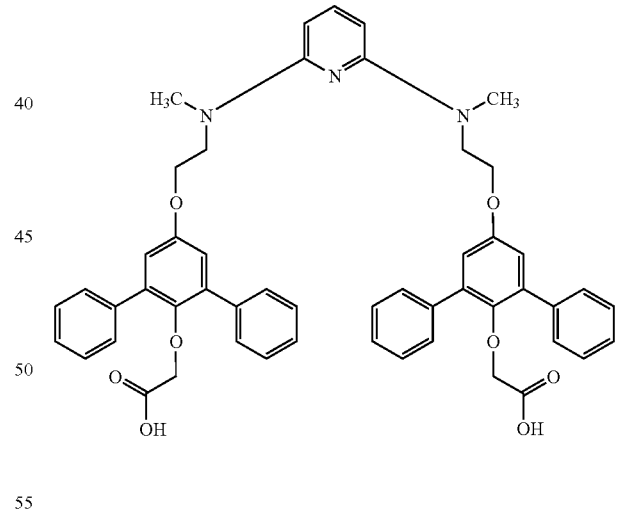

Step A:

Was synthesized as described under example 2, step A from (5'-{2-[(6-{[2-(2'-ethoxycarbonylmethoxy-[1,1';3',1"]terphenyl-5'-yloxy)-ethyl]-methyl-amino}-pyridin-2-yl)-methyl-amino]-ethoxy}-[1,1';3',1"]terphenyl-2'-yloxy)-acetic acid ethyl ester (example 3) in 15 mg (60%) yield.

$^1$H NMR (300 MHz, CDCl$_3$): δ 7.60-7.25 (m, 21 H); 6.84 (s, 4H); 5.86 (d, J=8 Hz, 2H); 4.19 (t, J=6 Hz, 4 H); 3.92 (t, J=6 Hz, 4H); 3.72 (s, 4H); 3.10 (s, 6H).

Example 5

General Procedure E (S,S)-2-(2-Benzoyl-phenylamino)-3-{4-[2-({6-[(2-{4-[2-(2-benzoyl-phenylamino)-2-methoxycarbonyl-ethyl]-phenoxy}-ethyl)-methyl-amino]-pyridin-2-yl}-methyl-amino)-ethoxy]-phenyl}-propionic acid methyl ester

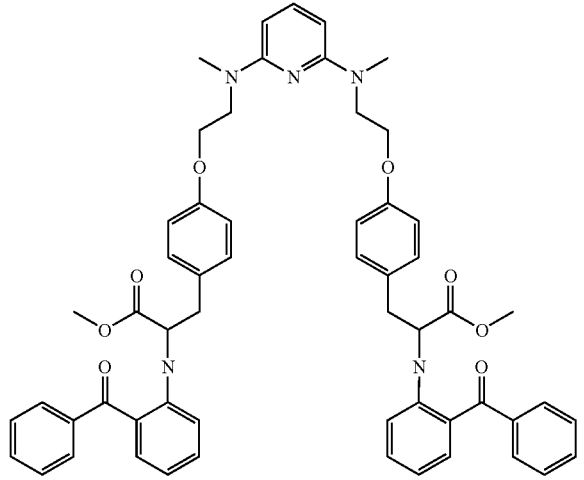

Step C-D:

Was synthesized as described under example 1, step C-D, using (S)-2-(2-benzoyl-phenylamino)-3-(4-hydroxy-phenyl)-propionic acid methyl ester (J. Med. Chem. 1998, 41, 5020-5036) (154 mg, 0.41 mmol) in stead of 2-ethoxy-3-(4-mercapto-phenyl)-propionic acid methyl ester giving the title compound in 46 mg (29%) yield.

$^1$H NMR (300 MHz, CDCl$_3$): δ 8.91 (d, J=7 Hz, 2H); 7.60 (d, J=7 Hz, 4H); 7.55-7.25 (m, 11H); 7.15 (d, J=8 Hz, 4H); 6.76 (d, J=8 Hz, 4H); 6.56-6.53 (m, 4H); 5.80 (d, J=8 Hz, 2H); 4.37 (q, J=6 Hz, 2H); 4.08 (t, J=6 Hz, 4H); 3.87 (t, J=6 Hz, 4H); 3.67 (s, 6H); 3.24-3.06 (m, 4H); 3.05 (s, 6H).

Example 6

General Procedure D (S,S)-2-(2-Benzoyl-phenylamino)-3-{4-[2-({6-[(2-{4-[2-(2-benzoyl-phenylamino)-2-carboxy-ethyl]-phenoxy}-ethyl)-methyl-amino]-pyridin-2-yl}-methyl-amino)-ethoxy]-phenyl}-propionic acid

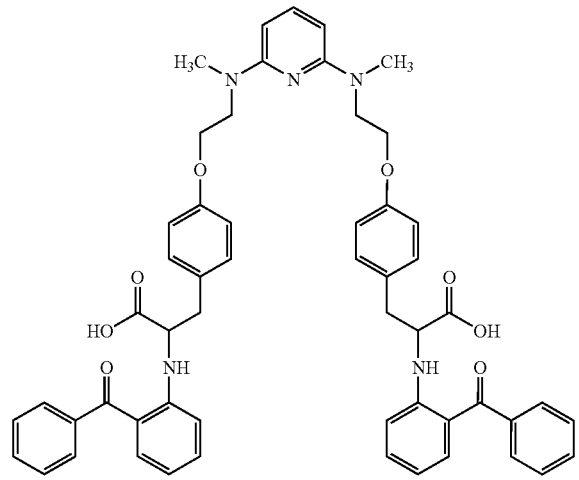

Step A:

Was synthesized as described under example 2, step A from (S,S)-2-(2-benzoyl-phenylamino)-3-{4-[2-({6-[(2-{4-[2-(2-benzoyl-phenylamino)-2-methoxycarbonyl-ethyl]-phenoxy}-ethyl)-methyl-amino]-pyridin-2-yl}-methyl-amino)ethoxy]-phenyl}-propionic acid methyl ester (example 5) in 42 mg (93%) yield.

$^1$H NMR (300 MHz, CDCl$_3$): δ 8.80 (br. s, 2H); 7.62-7.27 (m, 15 H); 7.10 (t, J=7 Hz, 4H); 6.72 (d, J=8 Hz, 6H); 6.60 (q, J=7 Hz, 2H); 5.84 (d, J=8 Hz, 2H); 4.48 (br s, 2H); 4.08 (t, J=6 Hz, 4H); 3.95 (t, J=6 Hz, 4H); 3.30-3.12 (m, 4H); 3.04 (d, J=5 Hz, 6H).

Example 7

General Procedure E (3-Chloro-4-{2-[(6-{[2-(2-chloro-4-ethoxycarbonyl-methyl-phenoxy)-ethyl]-methyl-amino}-pyridin-2-yl)-methyl-amino]-ethoxy}-phenyl)-acetic acid ethyl ester

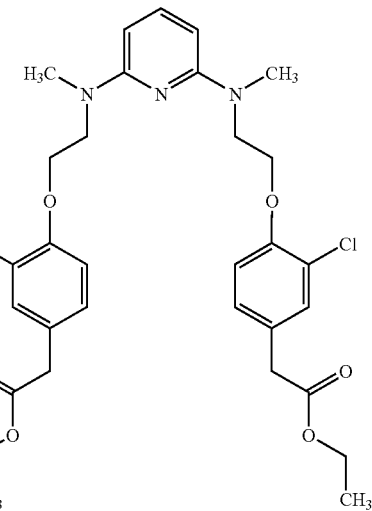

Step C-D:

Was synthesized as described under example 1, step C-D, using (3-chloro-4-hydroxy-phenyl)-acetic acid ethyl ester (US 6,090,836) (88 mg, 0.41 mmol) in stead of 2-ethoxy-3-(4-mercapto-phenyl)-propionic acid methyl ester giving the title compound in 45 mg (43%) yield.

$^1$H NMR (300 MHz, CDCl$_3$): δ 7.32-7.00 (m, 5H); 6.75 (d, J=8 Hz, 2H); 5.83 (d, J=8 Hz, 2H); 4.15 (m, 8H); 3.97 (t, J=6 Hz); 5.50 (s, 4H); 3.14 (s, 6H); 1.24 (t, J=6 Hz

Example 8

General Procedure D (4-{2-[(6-{[2-(4-Carboxymethyl-2-chloro-phenoxy)-ethyl]-methyl-amino}-pyridin-2-yl)-methyl-amino]-ethoxy}-3-chloro-phenyl)-acetic acid

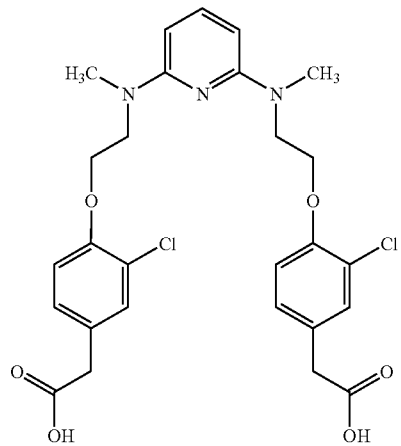

Step A:

Was synthesized as described under example 2, step A from (3-chloro-4-{2-[(6-{[2-(2-chloro-4-ethoxycarbonylmethyl-phenoxy)-ethyl]-methyl-amino}-pyridin-2-yl)-methyl-amino]-ethoxy}-phenyl)-acetic acid ethyl ester (example 7) in 90 mg (73%) yield.

$^1$H NMR (300 MHz, CDCl$_3$): δ 7.25 (m, 2H); 7.10-6.93 (m, 5H); 6.68 (d, J=8 Hz, 2H); 5.82 (d, J=8 Hz, 2H); 4.15 (t, J=6 Hz, 4H); 3.98 (t, J=6 Hz, 4H); 3.50 (s, 4H);

Example 9

General Procedure E (3-{2-[(6-{[2-(3-Ethoxycarbonylmethyl-phenoxy)-ethyl]-methyl-amino}-pyridin-2-yl)-methyl-amino]-ethoxy}-phenyl)-acetic acid ethyl ester

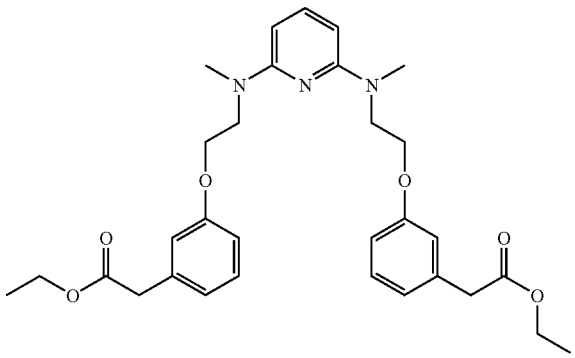

Step C-D:

Was synthesized as described under example 1, step C-D, using (3-hydroxy-phenyl)-acetic acid ethyl ester (U.S. Pat. No. 6,090,836) (74 mg, 0.41 mmol) in stead of 2-ethoxy-3-(4-mercapto-phenyl)-propionic acid methyl ester giving the title compound in 30 mg (32%) yield.

$^1$H NMR (300 MHz, CDCl$_3$): δ 7.34-7.14 (m, 3H); 6.87-6.70 (m, 6H); 5.84 (d, J=8 Hz, 2H); 4.15 (m, 8H); 3.93 (t, J=6 Hz, 4H); 3.54 (s, 4H); 3.10 (s, 6H); 1.24 (t, J=7 Hz, 6H).

Example 10

General Procedure D (3-{2-[(6-{[2-(3-Carboxymethyl-phenoxy)-ethyl]-methyl-amino}-pyridin-2-yl)-methyl-amino]-ethoxy}-phenyl)-acetic acid

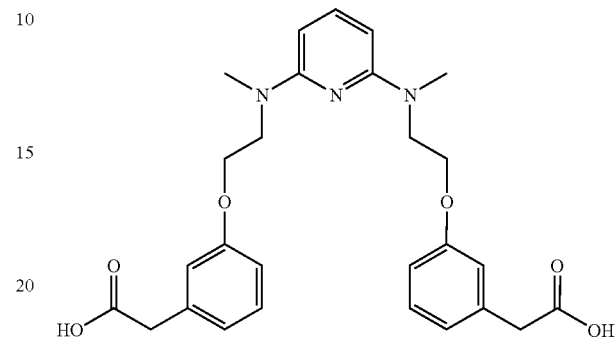

Step A:

Was synthesized as described under example 2, step A using (3-{2-[(6-{[2-(3-ethoxycarbonylmethyl-phenoxy)-ethyl]-methyl-amino}-pyridin-2-yl)-methyl-amino]-ethoxy}-phenyl)-acetic acid ethyl ester (example 9) in 26 mg (88%) yield.

$^1$H NMR (300 MHz, CDCl$_3$): δ 7.28-1.14 (m, 3H); 6.80 (m, 6H); 5.82 (d, J=8 Hz, 2H); 4.12 (t, J=6 Hz, 4H); 3.93 (t, J=6 Hz, 4H); 3.57 (s, 4H); 3.13 (s, 6H).

Example 11

General Procedure E (S,S)-2-Ethoxy-3-[4-(2-{[6-({2-[4-(2-ethoxy-2-ethoxycarbonyl-ethyl)-phenoxy]-ethyl}-methyl-amino)-pyridin-2-yl]-methyl-amino}-ethoxy)-phenyl]-propionic acid ethyl ester

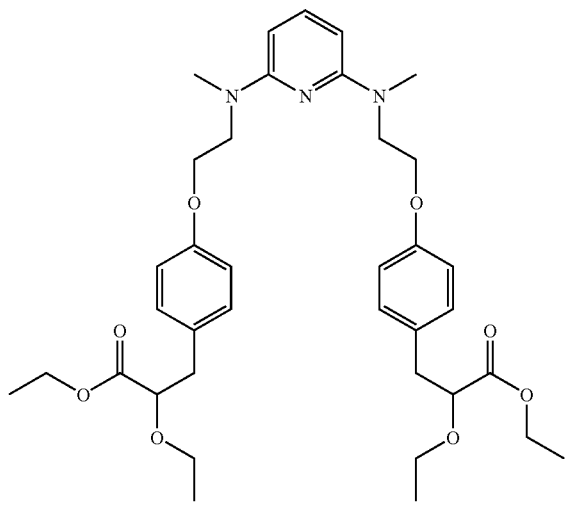

Step C-D:

Was synthesized as described under example 1, step C-D, using (S)-2-ethoxy-3-(4-hydroxy-phenyl)-propionic acid methyl ester (501 mg, 2.11 mmol) in stead of 2-ethoxy-3-(4-mercapto-phenyl)-propionic acid methyl ester giving the title compound in 106 mg (30%) yield.

$^1$H NMR (300 MHz, CDCl$_3$): δ 7.29 (t, J=8 Hz, 1H); 7.12 ( d, J=8 Hz, 4H); 6.77 (d, H=8 Hz, 4H); 5.82 (d, J=8 Hz, 2H); 4.14 (m, 8H); 5.93 (m, 6H); 3.60 (m, 2H); 3.35 (m, 2H); 3.07 (s, 6H); 2.94 (d, J=7 Hz, 4H); 1.22 (t, J=7 Hz, 6H); 1.14 (t, J=7 Hz, 6 H).

Example 12

General Procedure D (S,S)-3-[4-(2-{[6-({2-[4-(2-Carboxy-2-ethoxy-ethyl)-phenoxy]-ethyl}-methyl-amino)-pyridin-2-yl]-methyl-amino}-ethoxy)-phenyl]-2-ethoxy-propionic acid ethoxycarbonyl-ethyl)-phenoxy]-ethyl}-methyl-amino)-pyridin-2-yl]-methyl-amino}-ethoxy)-phenyl]-propionic acid ethyl ester (example 11) in 91 mg (93%) yield.

$^1$H NMR (300 MHz, CDCl$_3$): δ 7.29 (t, J=7 Hz, 1 H); 7.09 (d, J=8 Hz, 4H); 6.75 (d, J=8 Hz, 4H); 5.80 ( d, J=7 Hz, 2 H); 4.12 ( t, J=6 Hz, 4H); 4.04 (t, J=7 Hz, 2H); 3.94 (t, J=7 Hz, 4H); 3.62 (m, 2H); 3.42 (m, 2H); 3.07 (s, 6H); 3.05-2.92 (m, 4H); 1.17 (t, J=7 Hz, 6 H).

Example 13

General Procedure A (S,S)-2-Ethoxy-3-{4-[3-(4'-{3-[4-(2-ethoxy-2-iso-propoxycarbonyl-ethyl)-phenoxy]-propyl}-2,2'-bis-trifluoromethyl-biphenyl-4-yl)-propoxy]-phenyl}-propionic acid isopropyl ester

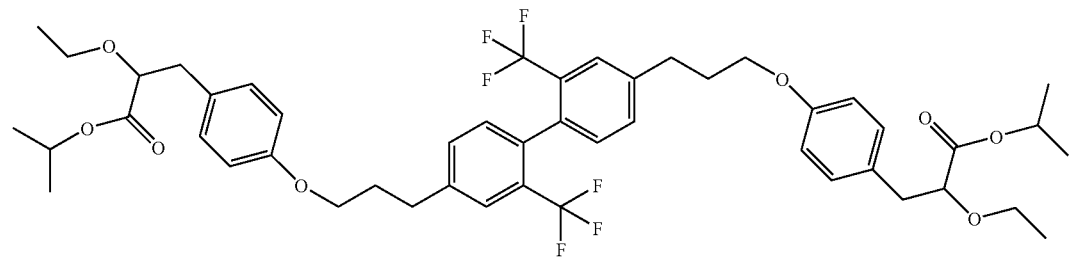

Step D-E:

To a stirred solution of 3-[4'-(3-hydroxy-propyl)-2,2'-bis-trifluoromethyl-biphenyl-4-yl]-propan-1-ol (intermediate 5) (102 mg, 0.25 mmol) in dry THF (10 ml) was added at 0° C. under nitrogen triphenylphosphine (252 mg, 1.0 mmol) and (S)-2-ethoxy-3-(4-hydroxy-phenyl)-propionic acid isopropyl ester (252 mg, 1.0 mmol). The reaction mixture was stirred for 15 min. and diethylazodicarboxylate (174 mg, 1.0 mmol) was added. The reaction was stirred for 6 h, after which water (10 ml) was added and the mixture was extracted with methylene chloride (3×20 ml). The combined organic phases were dried (MgSO$_4$), filtered and evaporated. The crude product was purified on column chromatograph using methylene chloride:THF (100:1) as eluent to give the title compound in 150 mg (69%) yield.

$^1$H NMR (400 MHz, CDCl$_3$): δ 7.57 (s, 2H); 7.37 (d, J=8 Hz, 2H); 7.18 (m, 6H); 6.83 (d, J=8 Hz, 4H); 5.04 (m, 2H); 3.98 (m, 6H); 3.61 (m, 2H); 3.36 (m, 2H); 2.93 (m, 8H); 2.15 (m, 4H); 1.25 (d, J=6 Hz, 12 H); 1.17 (t, J=6 Hz, 6H).

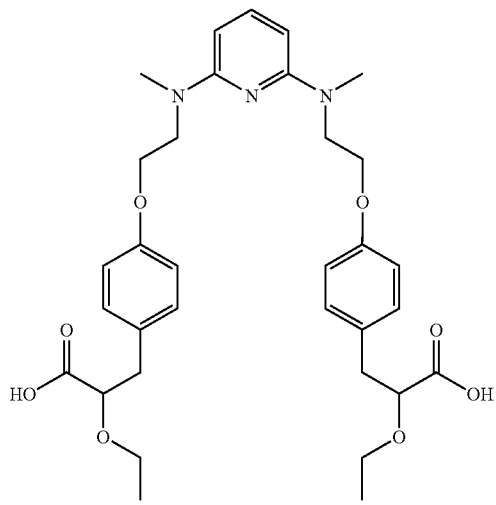

Step A:
Was synthesized as described under example 2, step A using (S,S)-2-ethoxy-3-[4-(2-{[6-({2-[4-(2-ethoxy-2-

Example 14

General Procedure D (S,S)-3-{4-[3-(4'-{3-[4-(2-Carboxy-2-ethoxy-ethyl)-phenoxy]-propyl}-2,2'-bis-trifluoromethyl-biphenyl-4-yl)-propoxy]-phenyl}-2-ethoxy-propionic acid

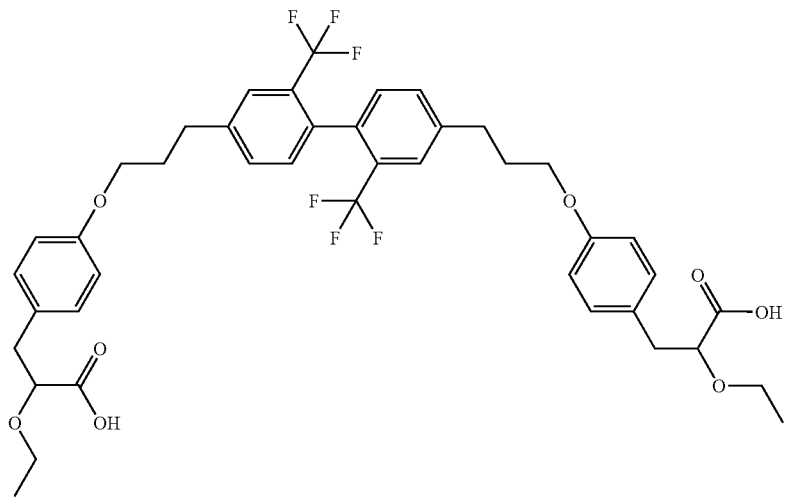

Step A:

To a solution of (S,S)-2-ethoxy-3-{4-[3-(4'-{3-[4-(2-ethoxy-2-isopropoxycarbonyl-ethyl)-phenoxy]-propyl}-2,2'-bis-trifluoromethyl-biphenyl-4-yl)-propoxy]-phenyl}-propionic acid isopropyl ester (example 13) in ethanol (4 ml) was added 1 N NaOH (0.6 ml) at room temperature. The reaction was stirred for 48 hours at room temperature and evaporated. The residue was treated with 1 N HCl and extracted with methylene chloride (2×15 ml). The combined organic phases were dried and evaporated to give the title compound in 105 mg (78%) yield.

$^1$H NMR (400 MHz, CDCl$_3$): δ 7.56 (s, 2H); 7.47 (d, J=8 Hz; 2H); 7.18 (m, 6H); 6.84 (d, J=8 Hz, 4H); 4.05 (m, 2H); 4.00 (t, J=6 Hz, 4H); 3.63 (m, 2H); 3.41 (m, 2H); 3.07 (m, 2H); 2.96 (m, 2H); 2.91 (t, J=6 Hz, 4H); 2.15 (m, 4H); 1.17 (t, J=6 Hz, 6H).

Example 15

General Procedure A (S,S)-2-Ethoxy-3-{4-[3-(4'-{3-[4-(2-ethoxy-2-isopropoxycarbonyl-ethyl)-phenoxy]-propyl}-3,3'-bis-trifluoromethyl-biphenyl-4-yl)-propoxy]-phenyl}-propionic acid isopropyl ester

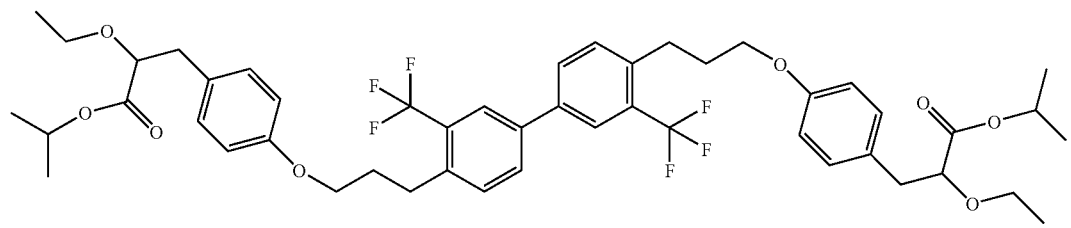

Step D-E:

Was synthesized as described under example 13 step C-A using 3-[4'-(3-hydroxy-propyl)-3,3'-bis-trifluoromethyl-biphenyl-4-yl]-propan-1-ol (intermediate 6) (102 mg, 0.25 mmol) instead of 3-[4'-(3-hydroxy-propyl)-2,2'-bis-trifluoromethyl-biphenyl-4-yl]-propan-1-ol giving the title compound in 205 mg (93%) yield.

$^1$H NMR (400 MHz, CDCl$_3$): δ 7.82 (s, 2H); 7.67 (d, J=8 Hz, 2H); 7.45 (d, J=8 Hz, 2H); 7.16 (d, J=8 Hz, 4H); 6.84 (d, J=8 Hz, 4H); 5.04 (m, 2H); 4.01 (t, J=6 Hz, 4H); 3.96 (t, J=6 Hz, 2H); 3.61 (m, 2H); 3.37 (m, 2H); 3.04 (t, J=6 Hz, 4H); 2.95 (d, J=6 Hz, 4H); 2.14 (m, 4H); 1.28-1.13 (m, 18 H).

Example 16

General Procedure D (S,S)-3-{4-[3-(4'-{3-[4-(2-Carboxy-2-ethoxy-ethyl)-phenoxy]-propyl}-3,3'-bis-trifluoromethyl-biphenyl-4-yl)-propoxy]-phenyl}-2-ethoxy-propionic acid ethyl-biphenyl-4-yl)-propoxy]-phenyl}-propionic acid isopropyl ester (example 15) to give the title compound in 167 mg (90%) yield.

$^1$H NMR (400 MHz, CDCl$_3$): δ 7.83 (s, 2H); 7.67 (d, J=8 Hz, 2H); 7.45 (d, J=8 Hz, 2H); 7.18 (d, J=8 Hz, 4H); 6.85 (d, J=8 Hz, 4H); 4.04 (m, 6H); 3.64 (m, 2H); 3.44 (m, 2H); 3.12-2.93 (m, 8H); 2.14 (m, 4H); 1.19 (t, J=6 Hz, 6H).

Example 17

General Procedure A (S,S)-3-{3-Bromo-4-[3-(4'-{3-[2-bromo-4-(2-ethoxy-2-isopropoxycarbonyl-ethyl)-phenoxy]-propyl}-2,2'-bis-trifluoromethyl-biphenyl-4-yl)-propoxy]-phenyl}-2-ethoxy-propionic acid iso-propyl ester

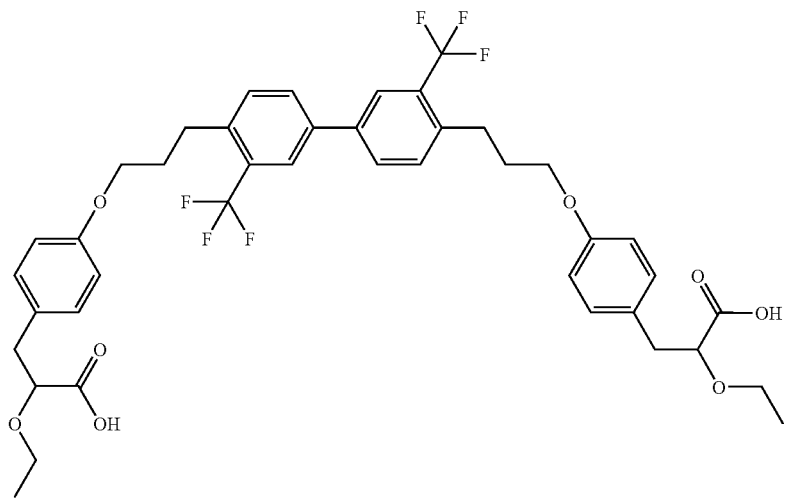

Step A:

Was synthesized as described under example 14 step A using (S,S)-2-ethoxy-3-{4-[3-(4'-{3-[4-(2-ethoxy-2-isopropoxycarbonyl-ethyl)-phenoxy]-propyl}-3,3'-bis-trifluorom-

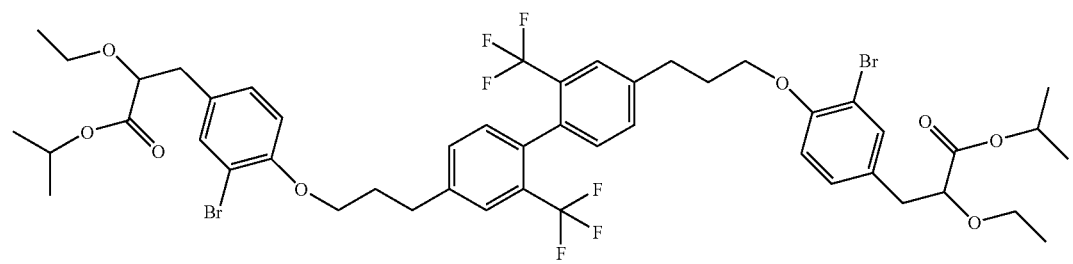

Step D-E:

Was synthesized as described under example 13 step D-E using (S)-3-(3-bromo-4-hydroxy-phenyl)-2-ethoxy-propionic acid isopropyl ester (intermediate 7) (331 mg, 1.0 mmol) instead of 2-ethoxy-3-(4-hydroxy-phenyl)-propionic acid isopropyl ester to give the title compound 160 mg (62%) yield.

$^1$H NMR (400 MHz, CDCl$_3$): δ 7.58 (s, 2H); 7.45 (s, 2H); 7.40 (d, J=8 Hz, 2H); 7.19 (d, J=8 Hz, 2H); 7.14 (d, J=8 Hz, 2H); 6.78 ( d, J=8 Hz, 2H); 5.05 (m, 2H); 4.04 (t, J=6 Hz. 4H); 3.94 ( t, J=6 Hz, 2H); 3.63 (m, 2H); 3.37 (m, 2H); 2.99 (t, J=6 Hz, 4H); 2.93 (d, J=6 Hz, 4H); 2.20 (m, 4H); 1.27-1-14 (m, 18H).

Example 18

General Procedure D (S,S)-3-{3-Bromo-4-[3-(4'-{3-[2-bromo-4-(2-carboxy-2-ethoxy-ethyl)-phenoxy]-propyl}-2,2'-bis-trifluoromethyl-biphenyl-4-yl)-propoxy]-phenyl}-2-ethoxy-propionic acid fluoromethyl-biphenyl-4-yl)-propoxy]-phenyl}-2-ethoxy-propionic acid isopropyl ester (example 17) to give the title compound in 112 mg (76%) yield.

$^1$H NMR (400 MHz, CDCl$_3$): δ 7.58 (s, 2H); 7.47 (s, 2H); 7.39 (d, J=8 Hz, 2H); 7.20 (d, J=8 Hz, 2H); 7.15 (d, J=8 Hz, 2H); 6.78 (d, J=8 Hz, 2H); 4.02 (m, 6H); 3.65 (m, 2H); 3.40 (m, 2H); 3.08-2.90 (m, 8H); 2.20 (m, 4H); 1.19 (t, J=6 Hz, 6H).

Example 19

General Procedure A (S,S)-3-{3-Bromo-4-[3-(4'-{3-[2-bromo-4-(2-ethoxy-2-isopropoxycarbonyl-ethyl)-phenoxy]-propyl}-3,3'-bis-trifluoromethyl-biphenyl-4-yl)-propoxy]-phenyl}-2-ethoxy-propionic acid iso-propyl ester

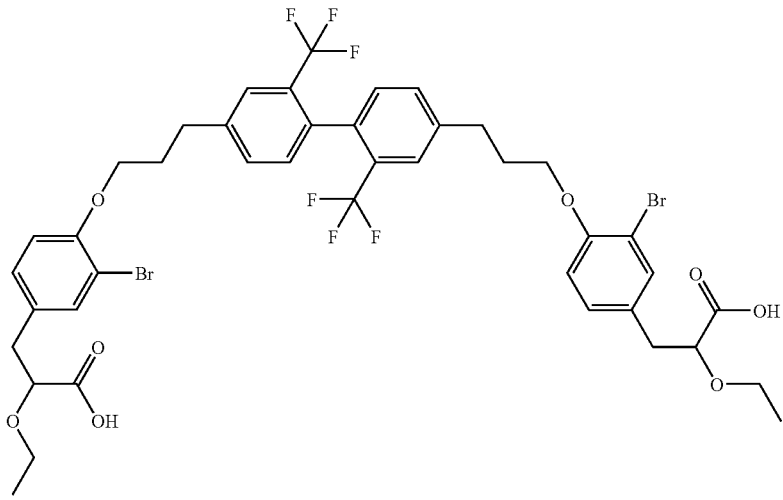

Step A:

Was synthesized as described under example 14 step A using (S,S)-3-{3-bromo-4-[3-(4'-{3-[2-bromo-4-(2-ethoxy-2-isopropoxycarbonyl-ethyl)-phenoxy]-propyl}-2,2'-bis-tri-

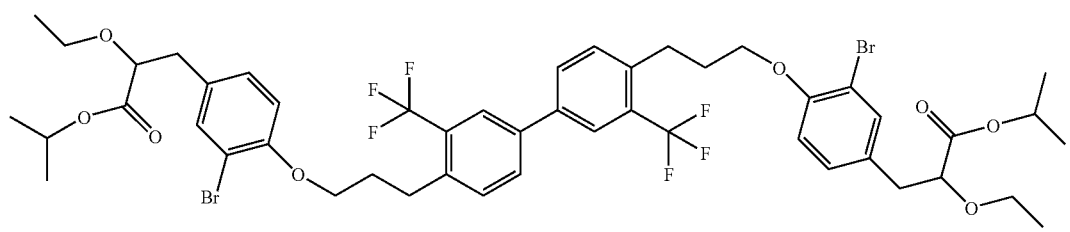

Step D-E:

Was synthesized as described under example 17 step D-E using 3-[4'-(3-hydroxy-propyl)-3,3'-bis-trifluoromethyl-biphenyl-4-yl]-propan-1-ol (intermediate 6) (102 mg, 0.25 mmol) instead of 3-[4'-(3-hydroxy-propyl)-2,2'-bis-trifluoromethyl-biphenyl-4-yl]-propan-1-ol giving the title compound in 132 mg (51%) yield.

$^1$H NMR (400 MHz, CDCl$_3$): δ 7.82 (s, 2H); 7.67 (d, J=8 Hz, 2H); 7.47 (m, 4H); 7.15 (d, J=8 Hz, 2H); 6.80 (d, J=8 Hz, 2H); 5.05 (m, 2H); 4.05 (t, J=6 Hz, 4H); 3.93 (t, J=6 Hz, 2H); 3.63 (m, 2H); 3.37 (m, 2H); 3.10 (t, J=7 Hz, 4H); 2.94 (d, J=6Hz, 4H); 2.17 (m, 4H); 1.28-1.14 (m, 18H).

Example 20

General Procedure D (S,S)-3-{3-Bromo-4-[3-(4'-{3-[2-bromo-4-(2-carboxy-2-ethoxy-ethyl)-phenoxy]-propyl}-3,3'-bis-trifluoromethyl-biphenyl-4-yl)-propoxy]-phenyl}-2-ethoxy-propionic acid

Example 21

General Procedure A (S,S)-3-{3-Bromo-4-[3-(7-{3-[2-bromo-4-(2-ethoxy-2-isopropoxycarbonyl-ethyl)-phenoxy]-propyl}-9H-fluoren-2-yl)-propoxy]-phenyl}-2-ethoxy-propionic acid isopropyl ester

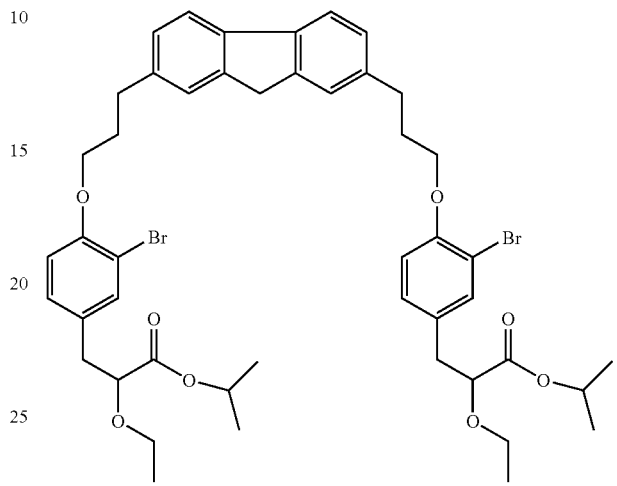

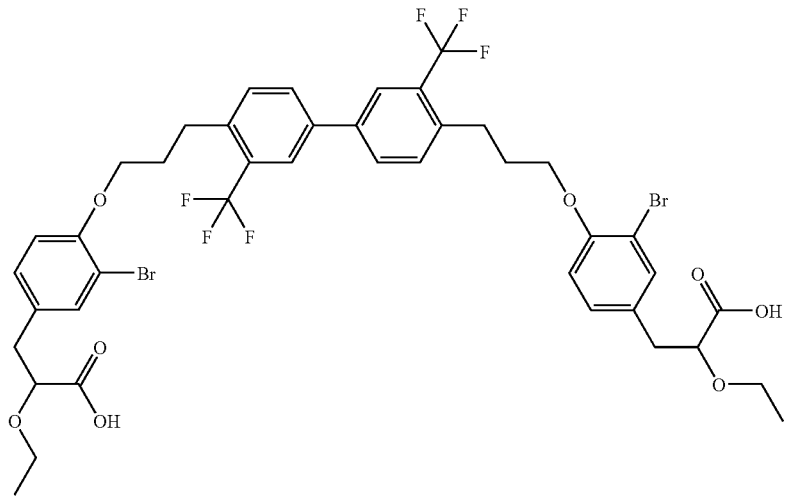

Step A:

Was synthesized as described under example 14 step A using (S,S)-3-{3-bromo-4-[3-(4'-{3-[2-bromo-4-(2-ethoxy-2-isopropoxycarbonyl-ethyl)-phenoxy]-propyl}-3,3'-bis-trifluoromethyl-biphenyl-4-yl)-propoxy]-phenyl}-2-ethoxy-propionic acid isopropyl ester (example 19) to give the title compound in 95 mg (78%) yield.

$^1$H NMR (400 MHz, CDCl$_3$): δ 7.82 (s, 2H); 7.67 (d, J=8 Hz, 2H); 7.49 (m, 4H); 7.15 (d, J=8 Hz, 2H); 6.82 (d, J=8 Hz, 2H); 4.05 (m, 6H); 3.66 (m, 2H); 3.42 (m, 2H); 3.14-2.90 (m, 8H); 2.16 (m, 4H); 1.19 (t, J=6 Hz, 6H).

Step D-E:

Was synthesized as described under example 17 step D-E using 3-[7-(3-hydroxy-propyl)-9H-fluoren-2-yl]-propan-1-ol (intermediate 8) (85 mg, 0.30 mmol) instead of 3-[4'-(3-hydroxy-propyl)-2,2'-bis-trifluoromethyl-biphenyl-4-yl]-propan-1-ol giving the title compound in 100 mg (37%) yield.

$^1$H NMR (400 MHz, CDCl$_3$): δ 7.64 (d, J=8 Hz, 2H); 7.44 (s, 2H); 7.36 (s, 2H); 7.22 (d, J=8 Hz, 2H); 7.10 (d, J=8 Hz, 2H); 6.75 (d, J=8 Hz, 2H); 5.50 (m, 2H); 3.99 (t, J=6 Hz, 4H); 3.94 (t, J=6 Hz, 2H); 3.82 (s, 2H); 3.62 (m, 2H); 3.55 (m, 2H); 2.90 (m, 8H); 2.17-1.14 (m, 18H).

Example 22

General Procedure D (S,S)-3-{3-Bromo-4-[3-(7-{3-[2-bromo-4-(2-carboxy-2-ethoxy-ethyl)-phenoxy]-propyl}-9H-fluoren-2-yl)-propoxy]-phenyl}-2-ethoxy-propionic acid

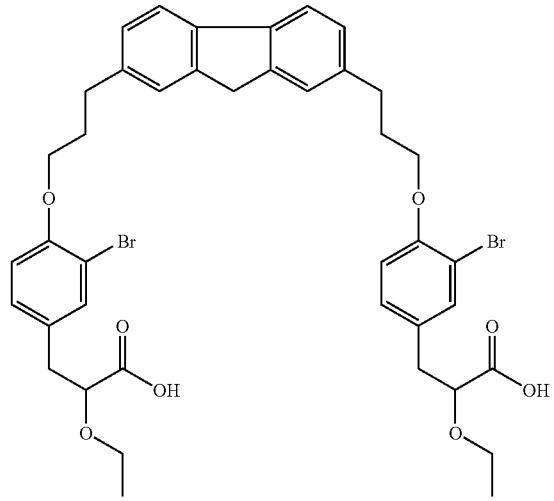

Step A:

Was synthesized as described under example 14 step A using (S,S)-3-{3-bromo-4-[3-(7-{3-[2-bromo-4-(2-ethoxy-2-isopropoxycarbonyl-ethyl)-phenoxy]-propyl}-9H-fluoren-2-yl)-propoxy]-phenyl}-2-ethoxy-propionic acid isopropyl ester (example 21) to give the title compound in 51 mg (56%) yield.

¹H NMR (400 MHz, CDCl₃): δ 7.57 (s, 2H); 7.47 (s, 2H); 7.38 (d, J=8 Hz, 2H); 7.18 (d, J=8 Hz, 2H); 7.14 (d, J=8 Hz, 2H); 6.80 (d, J=8 Hz, 2H); 4.03 (t, J=6 Hz, 6H); 3.65 (m, 2H); 3.40 (m, 2H); 3.07-2.88 (m, 8H); 2.19 (m, 4H); 1.19 (t, J=6 Hz, 6H).

Example 23

General Procedure A (S,S)-2-Ethoxy-3-{4-[3-(7-{3-[4-(2-ethoxy-2-isopropoxycarbonyl-ethyl)-phenoxy]-propyl}-9H-fluoren-2-yl)-propoxy]-phenyl}-propionic acid isopropyl ester

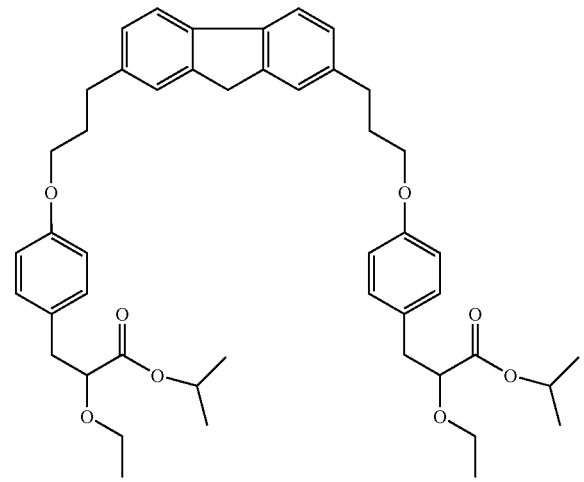

Step D-E:

Was synthesized as described under example 13 step D-E using 3-[7-(3-hydroxy-propyl)-9H-fluoren-2-yl]-propan-1-ol (intermediate 8) (102 mg, 0.25 mmol) instead of 3-[4'-3-hydroxy-propyl)-2,2'-bis-trifluoromethyl-biphenyl-4-yl]-propan-1-ol giving the title compound in 100 mg (45%) yield.

¹H NMR (400 MHz, CDCl₃): 7.64 (d, J=8 Hz, 2H); 7.35 (s, 2H); 7.18 (d, J=8 Hz, 2H); 7.15 (d, J=8 Hz, 4H); 6.80 (d, J=8 Hz, 4H); 5.02 (m, 2H); 3.95 (m, 6H); 3.82 (s, 2H); 3.60 (m, 2H); 3.35 (m, 2H); 2.94 (d, J=7 Hz, 4H); 2.86 (t, J=7 Hz, 4H); 2.12 (m, 4H); 1.25-1.14 (m, 18H).

Example 24

General Procedure D (S,S)-3-{4-[3-(7-{3-[4-(2-Carboxy-2-ethoxy-ethyl)-phenoxy]-propyl}-9H-fluoren-2-yl)-propoxy]-phenyl}-2-ethoxy-propionic acid

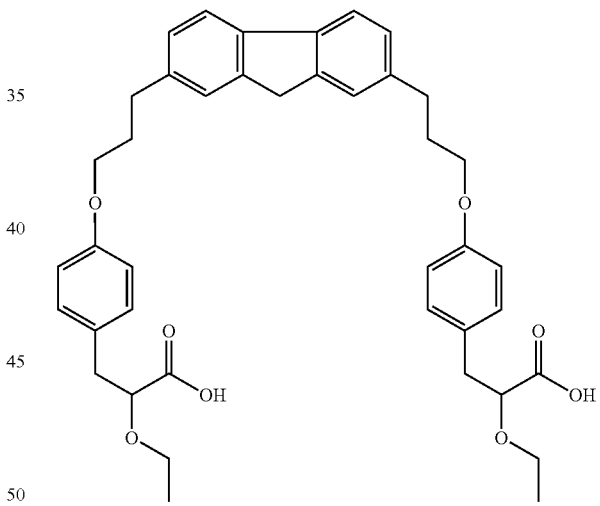

Step A:

Was synthesized as described under example 14 step A using (S,S)-2-ethoxy-3-{4-[3-(7-(3-[4-(2-ethoxy-2-isopropoxycarbonyl-ethyl)-phenoxy]-propyl)-9H-fluoren-2-yl)-propoxy]-phenyl}-propionic acid isopropyl ester (example 23) to give the title compound in 65 mg (73%) yield.

¹H NMR (400 MHz, CDCl₃): δ 7.65 (d, J=8 Hz, 2H); 7.36 (s, 2H); 7.18 (d, J=8 Hz, 2H); 7.16 (d, J=8 Hz, 4H); 6.83 (d, J=8 Hz, 4H); 4.04 (m, 2H); 3.96 (t, J=6 Hz, 4H); 3.82 (s, 2H); 3.63 (m, 2H); 3.44 (m, 2H); 3.06 (m, 2H); 2.96 (m, 2H); 2.86 (t, J=7 Hz, 4H); 2.12 (m, 4H); 1.17 (t, J=6 Hz, 6H).

Example 25

General Procedure A

[4-(3-{4'-[3-(4-Methoxycarbonylmethoxy-3-methyl-phenylsulfanyl)-propyl]-2,2'-bis-trifluoromethyl-biphenyl-4-yl}-propylsulfanyl)-2-methyl-phenoxy]-acetic acid methyl ester

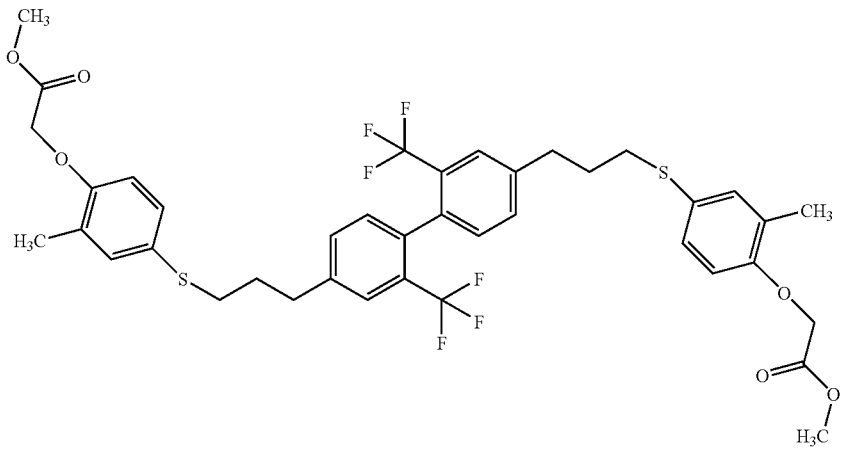

Step D-E:

Under nitrogen, azodicarboxylic dipiperidine (253 mg, 1.0 mmol) was added to a solution of 3-[4'-(3-hydroxy-propyl)-2,2'-bis-trifluoromethyl-biphenyl-4-yl]-propan-1-ol (intermediate 5) (102 mg, 0,25 mmol) and tributylphosphine (203 mg, 1.0 mmol) in THF (10 ml) at 0° C. The reaction mixture was stirred for 10 min after which (4-mercapto-2-methyl-phenoxy)-acetic acid methyl ester (intermediate 1) (213 mg, 1.0 mmol) was added prop wise over 5 min. The reaction mixture was stirred at 0° C. for 2 h and at room temperature for 1 h. Water (20 ml) was added and the reaction mixture was extracted with methylene chloride (3×25 ml). The combined organic phases were dried (MgSO$_4$), filtered and evaporated to give crude product. The residue was purified on column chromatography using methylene chloride:THF (100:1) as eluent to give the title compound in 102 mg (51%) yield.

$^1$H NMR (400 MHz, CDCl$_3$): δ 7.51 (s, 2H); 7.35-7.14 (m, 8H); 6.64 (d, J=8 Hz, 2H); 4.63 (s, 4H); 3.79 (s, 6H); 2.86 (m, 8H); 2.26 (s, 6H); 1.95 (m, 4H).

Example 26

General Procedure D

[4-(3-{4'-[3-(4-Carboxymethoxy-3-methyl-phenyl-sulfanyl)-propyl]-2,2'-bis-trifluoromethyl-biphenyl-4-yl}-propylsulfanyl)-2-methyl-phenoxy]-acetic acid

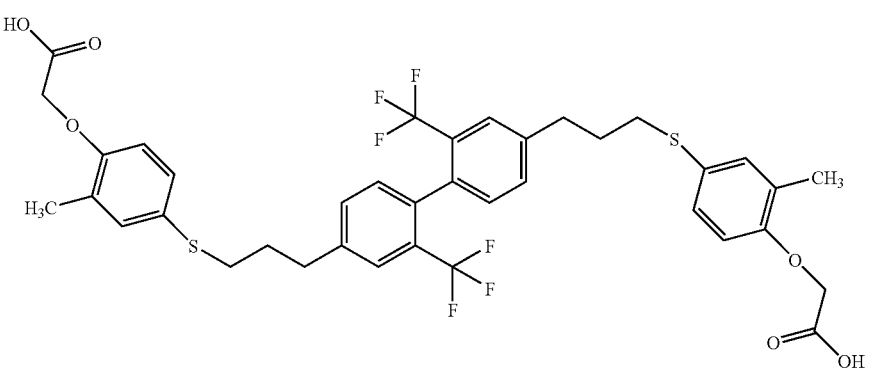

Step A:

To a solution of [4-(3-{4'-[3-(4-methoxycarbonyl-methoxy-3-methyl-phenylsulfanyl)-propyl]-2,2'-bis-trifluoromethyl-biphenyl-4-yl}-propylsulfanyl)-2-methyl-phenoxy]-acetic acid methyl ester (example 25) (102 mg, 0.12 mmol) in ethanol (5 ml) was added aqueous 1N NaOH (0.5 ml). The reaction mixture was stirred for 3 hours at room temperature and the evaporated. Water (10 ml) and 1 N HCl (0.6 ml) was added to the residue and the mixture was extracted with methylene chloride (2×30 ml). The combined organic phases were dried (MgSO₄), filtered and evaporated to give the title compound in 96 mg (98%) yield.

$^1$H NMR (400 MHz, CDCl$_3$): δ 7.51 (s, 2H); 7.32 (d, J=8 Hz, 2H); 7.15 (m, 6H); 6.65 (d, J=8 Hz, 2H); 4.64 (s, 4H); 2.85 (m, 8H); 2.25 (s, 6H); 1.95 (m, 4H).

Example 27

General Procedure A

[4-(3-{4'-[3-(4-Methoxycarbonylmethoxy-3-methyl-phenylsulfanyl)-propyl]-3,3'-bis-trifluoromethyl-biphenyl-4-yl}-propylsulfanyl)-2-methyl-phenoxy]-acetic acid methyl ester

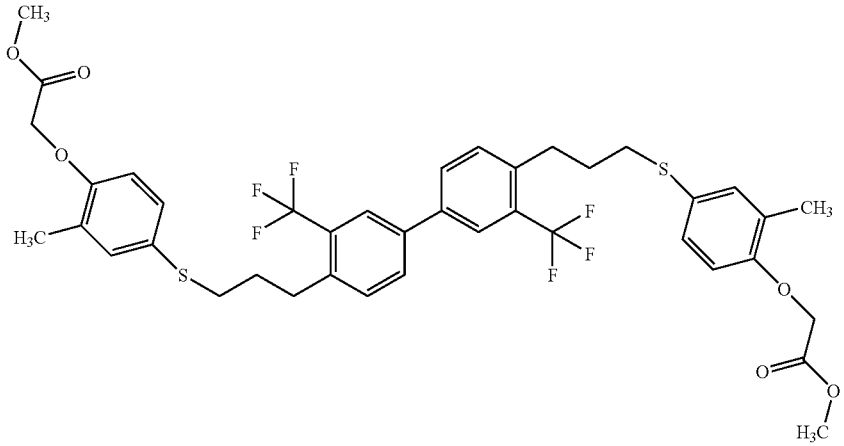

Step D-E:

Was synthesized as described under example 25 step D-E using 3-[4'-(3-hydroxy-propyl)-3,3'-bis-trifluoromethyl-biphenyl-4-yl]-propan-1-ol (intermediate 6) (102 mg, 0.25 mmol) instead of 3-[4'-(3-hydroxy-propyl)-2,2'-bis-trifluoromethyl-biphenyl-4-yl]-propan-1-ol to give the title compound in 130 mg (65%) yield.

$^1$H NMR (400 MHz, CDCl$_3$): δ 7.77 (s, 2H); 7.65 (d, J=8 Hz, 2H); 7.37 (d, J=8 Hz, 2H); 7.22 (m, 4H); 6.64 (d, J=8 Hz, 2H); 4.64 (s, 4H); 3.81 (s, 6H); 2.93 (m, 8H); 2.26 (s, 6H); 1.93 (m, 4H).

Example 28

General Procedure D

[4-(3-{4'-[3-(4-Carboxymethoxy-3-methyl-phenylsulfanyl)-propyl]-3,3'-bis-trifluoromethyl-biphenyl-4-yl}-propylsulfanyl)-2-methyl-phenoxy]-acetic acid

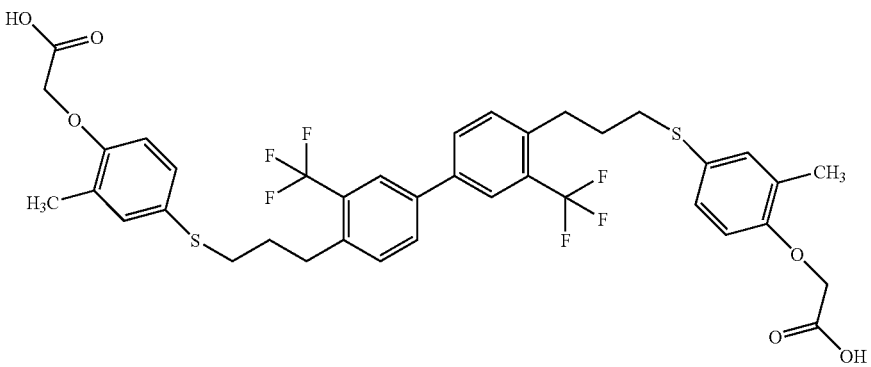

Step A:

Was synthesized as described under example 26 step A using [4-(3-{4'-[3-(4-methoxycarbonylmethoxy-3-methyl-phenylsulfanyl)-propyl]-3,3'-bis-trifluoromethyl-biphenyl-4-yl}-propylsulfanyl)-2-methyl-phenoxy]-acetic acid methyl ester (example 27) to give the title compound in 130 mg (96%) yield.

¹H NMR (400 MHz, MeOD): δ 7.81 (s, 2H); 7.75 (d, J=8 Hz, 2H); 7.43 (J=8 Hz, 2H); 7.17 (m, 4 H); 6.75 (d, J=8 Hz, 2H); 4.64 (s, 4H); 2.90 (m, 8H); 2.24 (s, 6H); 1.87 (m, 4H).

Example 29

General Procedure A

[4-(3-{7-[3-(4-Methoxycarbonylmethoxy-3-methyl-phenylsulfanyl)-propyl]-9H-fluoren-2-yl}-propylsulfanyl)-2-methyl-phenoxy]-acetic acid methyl ester

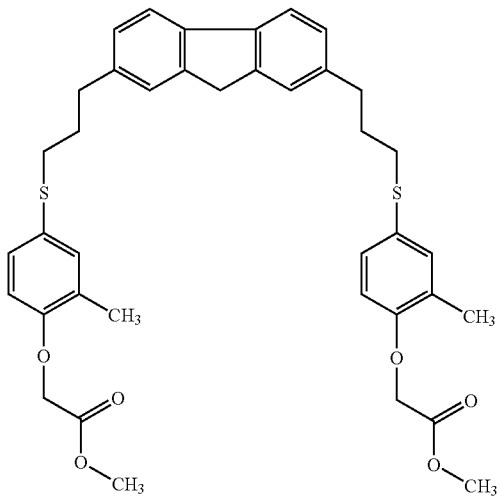

Step D-E:

Was synthesized as described under example 25 step D-E using 3-[7-(3-hydroxy-propyl)-9H-fluoren-2-yl]-propan-1-ol (Intermediate 8) (85mg, 0.3 mmol) instead of 3-[4'-(3-hydroxy-propyl)-2,2'-bis-trifluoromethyl-biphenyl-4-yl]-propan-1-ol to give the title compound in 34 mg (17%) yield after a second column purification using heptane:ethyl acetate (5:2) as eluent.

¹H NMR (400 MHz, CDCl₃): δ 7.64 (d, J=8 Hz, 2H); 7.33 (s, 2H); 7.15 (m, 6H); 6.70 (d, J=8 Hz, 2H); 4.63 (s, 4H); 3.82 (s, 2H); 3.80 (s, 6H); 2.85 (t, J=6 Hz, 4H); 2.79 (t, J=6 Hz, 4H); 2.26 (s, 6H); 1.94 (m, 4H).

Example 30

General Procedure D

[4-(3-{7-[3-(4-Carboxymethoxy-3-methyl-phenylsulfanyl)-propyl]-9H-fluoren-2-yl}-propyl-sulfanyl)-2-methyl-phenoxy]-acetic acid

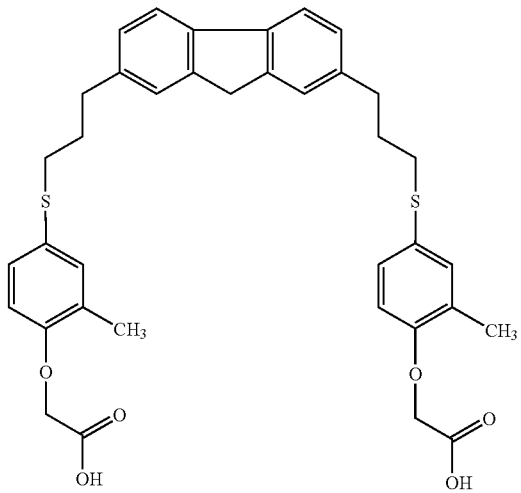

Step A:

Was synthesized as described under example 26 step A using [4-(3-{7-[3-(4-methoxycarbonylmethoxy-3-methyl-phenylsulfanyl)-propyl]-9H-fluoren-2-yl}-propylsulfanyl)-2-methyl-phenoxy]-acetic acid methyl ester (example 29) to give the title compound in 27 mg (73%) yield.

¹H NMR (400 MHz, DMSO): δ 7.73 (d, J=8 Hz, 2H); 7.35 (s, 2H); 7.16 (m, 6H); 6.78 (d, J=8 Hz, 2H); 4.67 (s, 4H); 3.83 (s, 2H); 2.87 (t, J=6 Hz, 4H); 2.75 (t, J=6 Hz, 4H); 2.16 (s, 6H); 1.84 (m, 4H).

Example 31

General Procedure A (4-{2-[2-(3-{4-[2-(4-Methoxycarbonylmethoxy-3-methyl-phenylsulfanyl)-ethyl]-5-methyl-oxazol-2-yl}-phenyl)-5-methyl-oxazol-4-yl]-ethylsulfanyl}-2-methyl-phenoxy)-acetic acid methyl ester

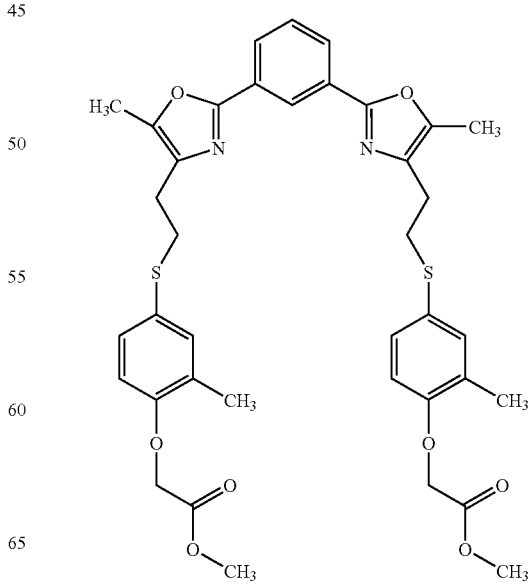

Step D-E:

Was synthesized as described under example 25 step D-E using 2-(2-{3-[4-(2-hydroxy-ethyl)-5-methyl-oxazol-2-yl]-phenyl}-5-methyl-oxazol-4-yl)-ethanol (intermediate 9) (99 mg, 0.3 mmol) instead of 3-[4'-(3-hydroxy-propyl)-2,2'-bis-trifluoromethyl-biphenyl-4-yl]-propan-1-ol to give the title compound in 123 mg (57%) yield after a second column purification using methylene chloride:THF (50:1) as eluent.

$^1$H NMR (400 MHz, CDCl$_3$): δ 8.49 (s, 1H); 7.99 (d, J=8 Hz, 2H); 7.48 (t, J=8 Hz, 1H); 7.23 (s, 2H); 7.17 (d, J=8 Hz, 2H); 6.61 (d, J=8 Hz, 2H); 4.58 (s, 4H); 3.80 (s, 6H); 3.17 (t, J=7 Hz, 4H); 2.78 (t, J=7 Hz, 4H); 2.32 (s, 6H); 2.24 (s, 6H).

Example 32

General Procedure D (4-{2-[2-(3-{4-[2-(4-Carboxymethoxy-3-methyl-phenylsulfanyl)-ethyl]-5-methyl-oxazol-2-yl}-phenyl)-5-methyl-oxazol-4-yl]-ethylsulfanyl}-2-methyl-phenoxy)-acetic acid

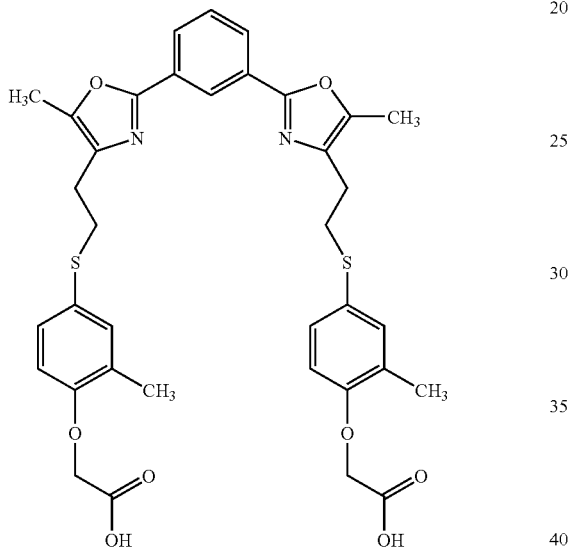

Step A:

Was synthesized as described under example 26 step A using (4-{2-[2-(3-{4-[2-(4-methoxycarbonylmethoxy-3-methyl-phenylsulfanyl)ethyl]-5-methyl-oxazol-2-yl}-phenyl)-5-methyl-oxazol-4-yl]-ethylsulfanyl}-2-methyl-phenoxy)-acetic acid methyl ester (example 31) to give the title compound in 108 mg (92%) yield.

$^1$H NMR (400 MHz, CDCl$_3$): δ 8.37 (s,1 H); 7.95 (d, J=8 Hz, 2H); 7.47 (t, J=8 Hz, 1 H); 7.16 (s, 2H); 7.06 (d, J=8 Hz, 2H); 6.54 (d, J=8 Hz, 2H); 4.52 (s, 4H); 3.15 (t, J=7 Hz, 4H); 2.82 (t, J=7 Hz, 4H); 2.24 (s, 6H); 2.19 (s, 6H).

Example 33

General Procedure A (S,S)-2-Ethoxy-3-[4-(2-{2-[4'-(4-{2-[4-(2-ethoxy-2-isopropoxycarbonyl-ethyl)-phenoxy]-ethyl}-5-methyl-oxazol-2-yl)-biphenyl-4-yl]-5-methyl-oxazol-4-yl}-ethoxy)-phenyl]-propionic acid isopropyl ester

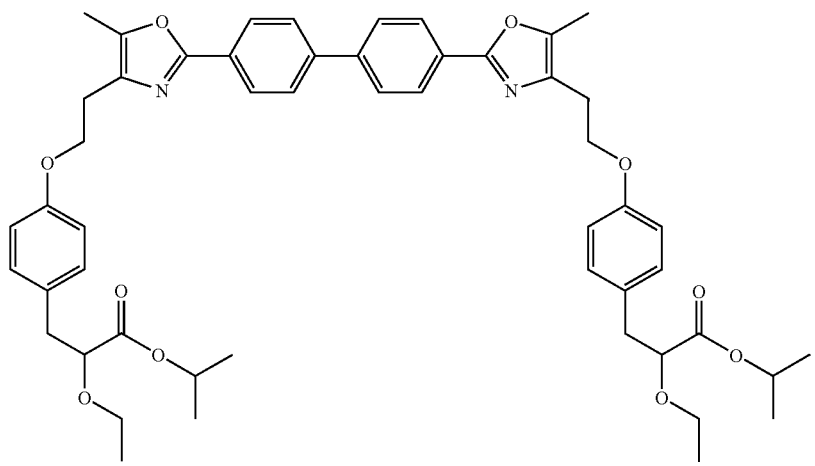

Step D-E:

Was synthesized as described under example 13 step D-E using 2-(2-{4'-[4-(2-hydroxy-ethyl)-5-methyl-oxazol-2-yl]-biphenyl-4-yl}-5-methyl-oxazol-4-yl)-ethanol (intermediate 10) (101 mg, 0.25 mmol) instead of 3-[4'-(3-hydroxy-propyl)-2,2'-bis-trifluoromethyl-biphenyl-4-yl]-propan-1-ol to give the title compound in 5 mg (2%) yield.

$^1$H NMR (400 MHz, CDCl$_3$): δ 8.05 (d, J=8 Hz, 4H); 7.70 (d, J=8 Hz, 4H); 7.15 (d, J=8 Hz, 4H); 6.83 (d, J=8 Hz, 4H); 5.02 (m, 2H); 4.23 (t, J=6 Hz, 4H); 3.94 (t, J=6 Hz, 2H); 3.58 (m, 2H); 3.35 (m, 2H); 2,99 (t, J=6 Hz, 4H); 2.94 (d, J=6 Hz, 4H); 2.39 (s, 6H); 1.24-1.13 (m, 18H).

Example 34

General Procedure D (S,S)-3-[4-(2-{2-[4'-(4-{2-[4-(2-Carboxy-2-ethoxy-ethyl)-phenoxy]-ethyl}-5-methyl-oxazol-2-yl-biphenyl-4-yl]-5-methyl-oxazol-4-yl}-ethoxy)-phenyl]-2-ethoxy-propionic acid Step A:

Was synthesized as described under example 26 step A using (S,S)-2-ethoxy-3-[4-(2-{2-[4'-(4-{2-[4-(2-ethoxy-2-isopropoxycarbonyl-ethyl)-phenoxy]-ethyl}-5-methyl-oxazol-2-yl)-biphenyl-4-yl]-5-methyl-oxazol-4-yl}-ethoxy)-phenyl]-propionic acid isopropyl ester (example 33) to give the title compound in 4 mg (100%) yield.

$^1$H NMR (400 MHz, CDCl$_3$): δ 8.05 (d, J=8 Hz, 4 H); 7.68 (d, J=8 Hz, 4H); 7.12 (m, 4H); 6.83 (d, J=8 Hz, 2H); 6.77 (d, J=8 Hz, 2H); 4.24 (t, J=6 Hz, 4H); 4.05 (m, 2H); 3.58 (m, 2H); 3.48 (m, 2H); 3.12-2.95 (m, 4H); 1.16 (t, J=6 Hz, 6H).

Example 35

General Procedure A (S,S)-2-Ethoxy-3-[4-(2-{2-[3-(4-{2-[4-(2-ethoxy-2-isopropoxycarbonyl-ethyl)-phenoxy]-ethyl}-5-methyl-oxazol-2-yl)-phenyl]-5-methyl-oxazol-4-yl}-ethoxy)-phenyl]-propionic acid isopropyl ester

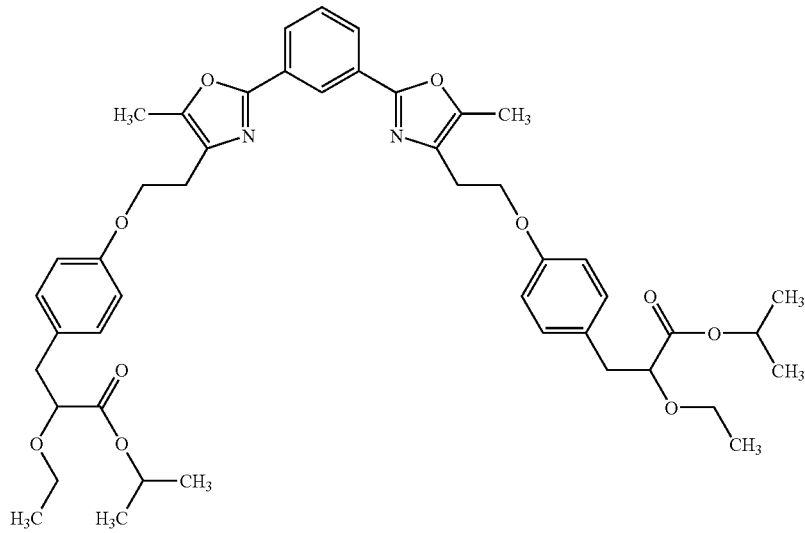

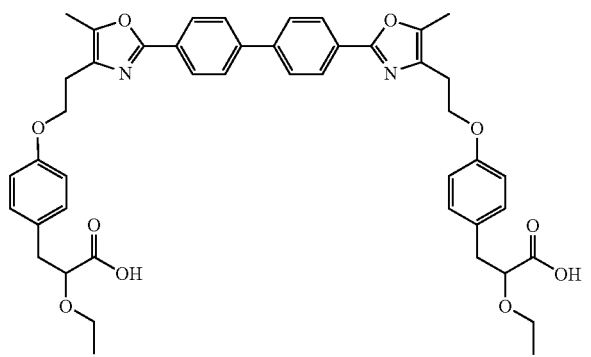

Step D-E:

Was synthesized as described under example 13 step D-E using 2-(2-{3-[4-(2-hydroxy-ethyl)-5-methyl-oxazol-2-yl]-phenyl}-5-methyl-oxazol-4-yl)-ethanol (intermediate 9) (164 mg, 0.5 mmol) instead of 3-[4'-(3-hydroxy-propyl)-2,2'-bis-trifluoromethyl-biphenyl-4-yl]-propan-1 -ol to give the title compound in 313 mg (84%) yield.

$^1$H NMR (400 MHz, CDCl$_3$): δ 8.57 (s, 1H); 8.03 (d, J=8 Hz, 2H); 7.47 (t, J=8 Hz, 1H); 7.14 (d, J=8 Hz, 4H); 6.82 (d, J=8 Hz, 4H); 5.02 (m, 2H); 4.23 (t, J=6 Hz, 4H); 3.93 (t, J=7 Hz, 2H); 3.58 (m, 2H); 3.34 (m, 2H); 2.98 (t, J=6 Hz, 4H); 2.93 (d, J=6 Hz, 4H); 2.38 (s, 6H); 1.30-1.12 (m, 18H).

Example 36

General Procedure D (S,S)-3-[4-(2-{2-[3-(4-{2-[4-(2-Carboxy-2-ethoxy-ethyl)-phenoxy]-ethyl-}-5-methyl-oxazol-2yl-phenyl]-5-methyl-oxazol-4-yl}-ethoxy)-phenyl]-2-ethoxy-propionic acid

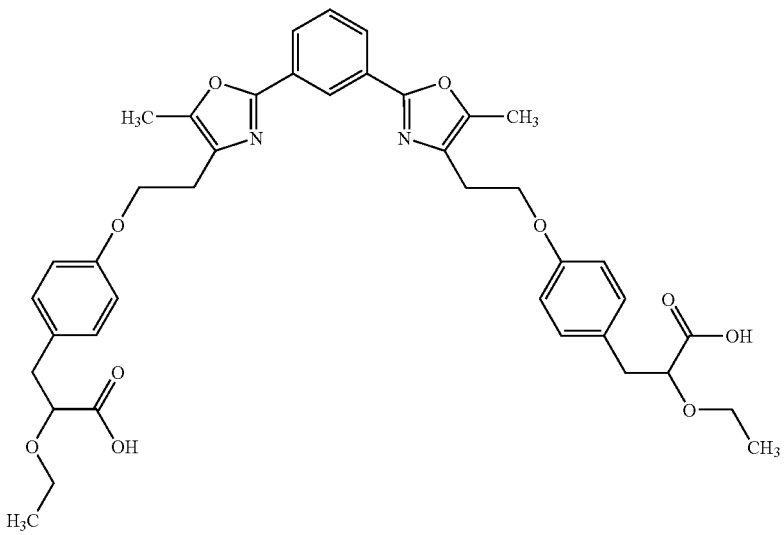

Step A:

Was synthesized as described under example 26 step A using (S,S)-2-ethoxy-3-[4-(2-{2-[3-(4-(2-[4-(2-ethoxy-2-isopropoxycarbonyl-ethyl)-phenoxy]-ethyl)-5-methyl-oxazol-2yl-phenyl]-5-methyl-oxazol-4-yl}-ethoxy)-phenyl]-propionic acid isopropyl ester (example 35) to give the title compound in 150 mg (44%) yield.

$^1$H NMR (400 MHz, CDCl$_3$): δ 8.45 (s, 1H); 7.94 (d, J=8 Hz, 2H); 7.42 (t, J=8 Hz, 1H); 7.06 (d, J=8 Hz, 4H); 6.72 (d, J=8 Hz, 4H); 4.14 (t, J=6 Hz, 4H); 3.94 (m, 2H); 3.32 (m, 2H); 3.02-2.81 (m, 8H); 2.26 (s, 6H); 1.06 (t, J=6 Hz, 6H).

Example 37

General Procedure B

[4-(3-{4'-[3-(4-Carboxymethylsulfanyl-3-chloro-phenylsulfanyl)-propyl]-3,3'-bis-rifluoromethyl-biphenyl-4-yl}-propylsulfanyl)-2-chloro-phenylsulfanyl]-acetic acid

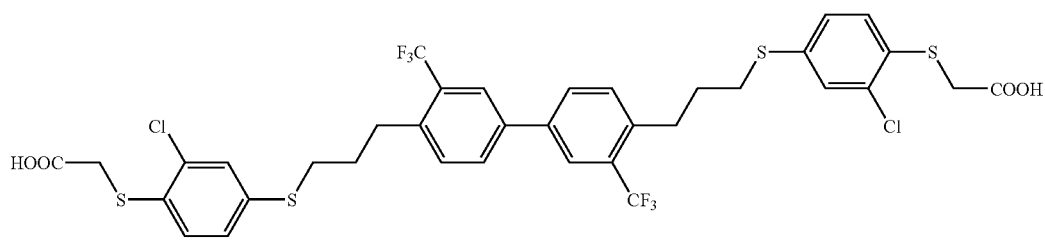

Step A-B:

(2-Chloro-4-mercapto-phenylsulfanyl)-acetic acid ethyl ester (intermediate 13) (3.7 g, 7 mmol) was dissolved in dimethylacetamide (20 mL). Sodium borohydride (0.5 g, 13.2 mmol) was added portionwise at 5° C. and the mixture was stirred for 30 min. 3,3'-Bistrifluoromethyl-4,4'-biphenyidipropanol (intermediate 6) bismethanesulfonate (3.25 g, 5.8 mmol) dissolved in 2-butanone (35 mL) and potassium carbonate (1.4 g, 10 mmol) were added and the mixture was stirred for 48 h at laboratory temperature. Water and benzene were added, the organic layer was separated, dried ($K_2CO_3$), filtered and evaporated to give a residue which was purified by chromatography on silica gel (100 g, benzene). This afforded 3.05 g (59%) of diethyl ester of the title compound.

$^1$H-NMR spectrum ($CDCl_3$): 7.80 (d, J=1.65 Hz, 2 H); 7.66 (dd, J=1.65 and 8.2 Hz, 2 H); 7.38 (d, J=8.2 Hz, 2 H); 7.34 (m, 4 H); 7.16 (dd, J=2.2 and 8.25 2 H); 4.15 (q, J=7.15 Hz, 4H); 3.63 (s, 4 H); 2.97 (m, 8 H); 1.99 (pent, 4 H); 1.22 (t, J=7.15 Hz, 6 H).

General Procedure D:

Step A:

The above diethyl ester (3.0 g, 3.35 mmol) was dissolved in the mixture of ethanol (30 mL) and tetrahydrofuran (30 mL), 20% sodium hydroxide (7 mL)) was added and the mixture was left to stand for 48 h. The solvents were evaporated, the residue was dissolved in water, the mixture was acidified with hydrochloric acid and the product was extracted with chloroform. The organic layer was dried ($MgSO_4$), evaporated and the residue was triturated with methanol yielding 2.17 g (72%) of the title compound as trihydrate.

M.p. 108-112° C.

$R_F$ ($SiO_2$, chloroform/ethanol 10:1) 0.40.

$^1$H NMR spectrum (300 MHz, DMSO-$d_6$): 7.91 (m, 4 H); 7.55 (d, J=7.7 Hz, 2 H); 7.40 (d, J=1.65 Hz, 2 H); 7.28 (m, 4 H); 3.86 (s, 4 H); 3.07 (t, J=7.15 Hz, 4 H); 2.89 (t, J=7.7 Hz, 4 H); 1.85 (m, 4 H).

Example 38

General Procedure B

[4-[3-[4'-[3-(4-Carboxymethoxy-3-trifluoromethylphenylsulfanyl)propyl]biphenyl-4-yl]-propylsulfanyl]-2-trifluoromethylphenoxy]acetic acid Step A:

3-[4'-(3-Hydroxy-propyl)-biphenyl-4-yl]-propan-1-ol (intermediate 14) (5.0 g, 18.5 mmol) was dissolved in dichloromethane (100 mL) and triethylamine (6.0 g, 59 mmol) and subsequently methanesulfonyl chloride (4.6 g, 40 mmol) were added dropwise. The mixture was stirred overnight, washed with water (30 mL), evaporated in vacuo and the residue crystallized from benzene giving 4,4'-biphenyidipropanol bismethanesulfonate.

Yield: 6.8 g (87%).

M.p. 155.5-157° C.

$^1$H NMR spectrum ($CDCl_3$): 7.51 (d, J=8.2 Hz, 4 H); 7.25 (m, 4 H); 4,26 (t, J=6.3 Hz, 4 H); 3.00 (s, 6 H); 2.79 (t, J=7.4 Hz, 4 H); 2.11 (m, 4 H).

Step B:

The 4,4'-dithiobis(2-trifluoromethylphenoxyacetic acid diethyl ester) (intermediate 11) (4.5 9, 8 mmol) was dissolved in N,N-dimethylacetamide (20 mL), sodium borohydride (0.6 g, 15.9 mmol) was added portionwise at 5° C. and the mixture was stirred for 30 min. The solution of above bismethanesulfonate (3.1 g, 7.3 mmol) in 2-butanone (30 ml) and potassium carbonate (1.4 g, 10 mmol) were added and the resulting mixture was stirred overnight at ambient temperature and then refluxed for 3 h. Water (250 mL) and benzene (150 mL) were added, the organic layer was separated, dried with anhydrous potassium carbonate, filtered and evaporated in vacuo. The residue was purified by column chromatography (silica gel Fluka 60, benzene). This afforded of [4-[3-[4'-[3-(4-Carboxymethoxy-3-trifluoromethyl-phenylsulfanyl)propyl]biphenyl-4-yl]-propylsulfanyl]-2-trifluoromethylphenoxy]acetic acid di-ethyl ester.

Yield: 3.35 g (58%).

M.p. 100.5-102.5° C. (benzene).

$^1$H NMR spectrum ($CDCl_3$): 7.61 (d, J=2.2 Hz, 2 H); 7.47 (m, 6 H); 7.21 (d, J=8.3 Hz, 4 H); 6.80 (d, J=8.8 Hz, 2 H); 4.70 (s, 4 H); 4.25 (q, J=7.2 Hz, 4 H); 2.88 (t, J=7.3 Hz, 4 H); 2.77 (t, J=7.2 Hz, 4 H); 1.94 (m, 4 H); 1.28 (t, J=7.2 Hz, 6 H).

General Procedure D:

Step A:

The above diethyl ester (3.25 g, 4.1 mmol) was dissolved in a mixture of ethanol (30 mL) and tetrahydrofuran (50 mL), 20% aqueous solution of sodium hydroxide (5 mL) was added and the mixture was left to stand for 48 h. The solvents were

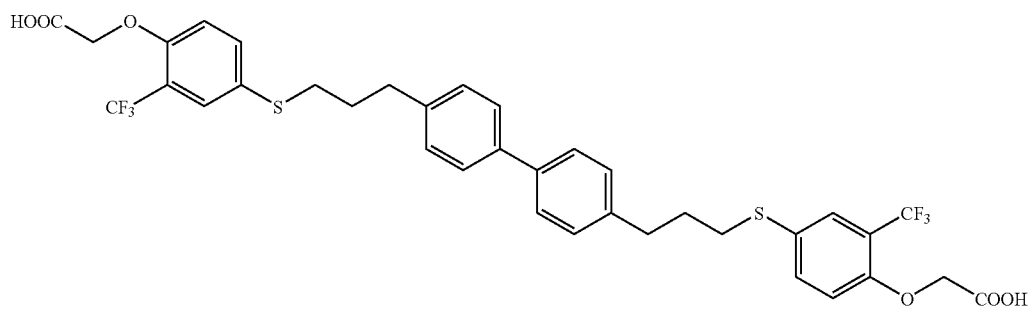

evaporated, the residue dissolved in water and precipitated with acetic acid: The title compound was filtered, washed with water and dried.

Yield: 2.9 g (96%).

M.p. 208-218° C.

$^1$H NMR spectrum (300 MHz, DMSO-$d_6$): 7.48-7.58 (m, 8 H); 7.21 (d, J=8.0 Hz, 4 H); 7.05 (d, J=8.5 Hz, 2 H); 4.76 (s, 4 H); 2.90 (t, J=7.2 Hz, 4 H); 2.70 (t, J=7.4 Hz, 4H); 1.81 (m, 4 H).

Example 39

General Procedure B

[4-[3-[4'-[3-(4-Carboxymethoxy-3-chlorophenylsulfanyl)propyl]-3,3'-bis-trifluoromethylbiphenyl-4-yl]propylsulfanyl]-2-chlorophenoxy]acetic acid

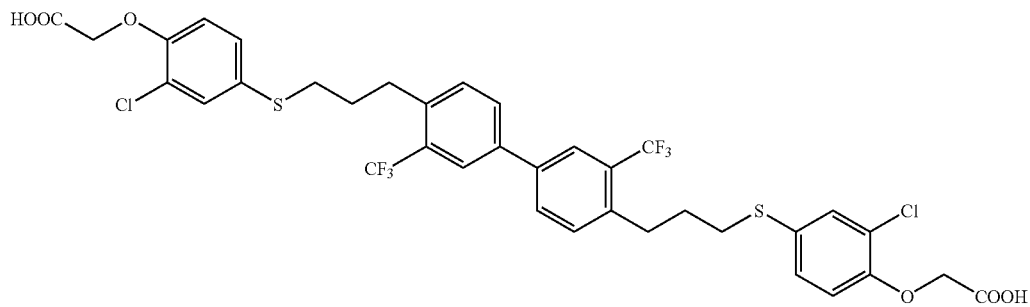

Step A:

To a solution of 3-[4'-(3-hydroxy-propyl)-3,3'-bis-trifluoromethyl-biphenyl-4-yl]-propan-1-ol (intermediate 6) (5.4 g, 13.3 mmol) in dichloromethane (40 mL) triethylamine (2.5 g, 24.7 mmol) and methanesulfonyl chloride (2.7g, 23.6 mmol) were added dropwise. The mixture was stirred overnight, diluted with dichloromethane (50 mL) and washed with water (2×15 mL). Evaporation of the organic solution gave 3,3'-bistrifluoromethyl-4,4'-biphenyl-dipropanol bismethanesulfonate.

Yield: 6.6 g (88%).

$^1$H NMR spectrum (CDCl$_3$): 7.81 (s, 2 H); 7.70 (d, J=8.0 Hz, 2 H); 7.44 (d, J=8.0 Hz, 2 H); 4.31 (t, J=6.1 Hz, 4 H); 3.04 (s, 6 H); 2.96 (t, J=7.8 Hz, 4 H); 2.11 (m, 4 H).

Step B:

4,4'-Dithiobis(2-chlorophenoxyacetic acid diethyl ester) (intermediate 12) (3.7 g, 7.5 mmol) was dissolved in N,N-dimethylacetamide (50 mL), sodium borohydride (0.55 g, 14.5 mmol) was added portionwise at 5° C. and the mixture was stirred for 30 min. A solution of the above bismethanesulfonate (3.25 g, 5.8 mmol) in 2-butanone (15 mL) and potassium carbonate (1.4 g, 10 mmol) were added to the mixture and the resulting suspension was stirred overnight at ambient temperature and subsequently refluxed for 3 h. Water (300 mL) and benzene (100 mL) were added, the organic layer was separated, dried with anhydrous potassium carbonate, filtered an d evaporated in vacuo. The residue was purified by column chromatography (silica gel Fluka 60, benzene) yielded [4-[3-[4'-[3-(4-Carboxymethoxy-3-chlorophenylsulfanyl)propyl]-3,3'-bis-trifluoromethylbiphenyl-4-yl]propylsulfanyl]-2-chloro-phenoxy]acetic acid diethyl ester.

Yield: 2.86 g (60%).

$^1$H NMR spectrum (CDCl$_3$): 7.79 (d, J=1.7 Hz, 2 H); 7.65 (dd, J=1.7 and 8.0 Hz, 2 H); 7.42 (d, J=2.2 Hz, 2 H); 7.37 (d, J=8.0 Hz, 2 H); 7.22 (dd, J=2.2 and 8.5 Hz, 2 H); 6.78 (d, J=8.5 Hz, 2 H); 4.68 (s, 4 H); 4.26 (q, J=7.2 Hz, 4 H); 2.93 (t, J=7.2 Hz, 8 H); 1.94 (m, 4 H); 1.29 (t, J=7.2 Hz, 6 H).

General Procedure D:

Step A:

The above diethyl ester (2.8 g, 3.5 mmol) was dissolved in ethanol (30 mL) and tetrahydrofuran (30 mL). 20% Aqueous solution of sodium hydroxide (7 mL) was added, the mixture was left to stand for 48 h and then evaporated in vacuo. The residue was dissolved in water and the title product was precipitated with hydrochloric acid. The solid mass was filtered, washed with water and dried.

Yield: 2.3 g (85%).

M.p. 143-152° C.

$^1$H NMR spectrum (300 MHz, DMSO-$d_6$): 7.89 (m, 4 H); 7.53 (d, J=7.7 Hz, 2 H); 7.43 (d, J=2.2 Hz, 2 H); 7.27 (dd, J=2.2 and 8.5 Hz, 2 H); 6.97 (d, J=8.5 Hz, 2 H); 4.77 (s, 4 H); 3.00 (t, J=7.1 Hz, 4 H); 2.86 (m, 4 H); 1.80 (m, 4 H).

Example 40

General Procedure B

[4-(3-{4'-[3-(4-Carboxymethoxy-3-chloro-phenylsulfanyl)-propyl]-biphenyl-4-yl}-propylsulfanyl)-2-chloro-phenoxy]-acetic acid

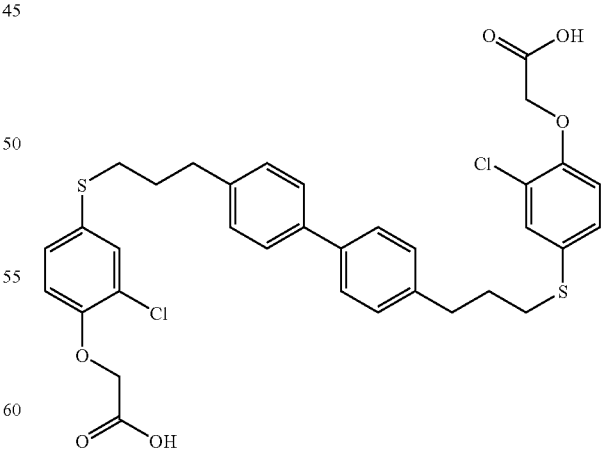

Step B:

The 4,4'-dithiobis-(2-chloromethylphenoxyacetic acid diethyl ester) (intermediate 12) (2.5 g, 5.1 mmol) was dissolved in 20 mL N,N-dimethylacetamide, sodium borohydride (0.50 g, 13.2 mmol) was added portionwise at 5° C. and the mixture was stirred for 30 min. 4,4'-Biphenyldipropanol bismethanesulfonate (example38) (2.1 g, 4.95 mmol) dissolved in 2-butanone (20 mL) and potassium carbonate (1.4 g, 10 mmol) were added and the mixture was stirred overnight at ambient temperature and then refluxed for 3 h. Water and benzene were added, the organic layer was dried ($K_2CO_3$), filtered and evaporated to give a residue which was purified by chromatography on silica gel (Fluka 60, 60 g, benzene). This afforded 2.3 g (64%) of diethyl ester of the title compound.

$^1$H-NMR spectrum (CDCl$_3$): 7.49 (d, 4H, J=8.0); 7.40 (d, 2H, J=2.2); 7.36 (m,2H); 7.22 (m, 4H);6.76 (d, 2H, J=8.5); 4.67 (s, 4H); 4.26 (q, 4H, J=7.15); 2.87 (t, 4H); 1.95 (pent, 4H); 1.29 (t, 6H, J=7.15).

General Procedure D:

Step A:

The above diethyl ester (2.2 g, 2.9 mmol) was dissolved in 50 mL ethanol, 20% solution of sodium hydroxide (5 mL) was added and the mixture was left to stand for 48 h. The solvents were evaporated, the residue dissolved in water and the product precipitated with HCl. The solid was filtered with suction, washed with water and dried yielding 1.95 g (96%) of the title compound which was recrystallized from dioxane/water to give 1.44 g of the solvate with ½ mol dioxane.

M.p. 181.5-184.5° C.

R$_F$ (free acid, SiO$_2$, ethyl acetate) 0.53.

$^1$H NMR spectrum (300 MHz, DMSO-d$_6$): 13.10 (s, 2 H); 7.52 (d, J=8.2 Hz, 4 H); 7.41 (d, J=2.2 Hz, 2 H); 7.26 (dd, J=2.2 and 8.8 Hz, 2 H); 7.22 (d, J=8.2 Hz, 4 H); 6.97 (d, J=8.8 Hz, 2 H); 4.79 (s, 4 H); 2.88 (t, J=7.15 Hz, 4 H); 2.69 (t, J=7.15 Hz, 4 H); 1.80 (p, 4 H); dioxane 3.55 (s).

Example 41

General Procedure B

[4-(3-{4'-[3-(4-Carboxymethoxy-3-methoxy-phenyl-sulfanyl)-propyl]-biphenyl-4-yl}-propylsulfanyl)-2-methoxy-phenoxy]-acetic acid

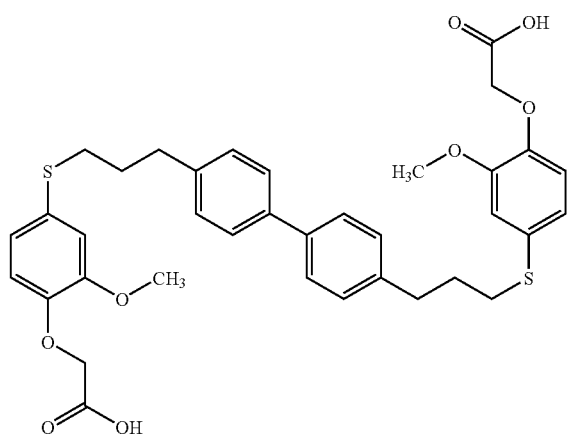

Step B:

A mixture of methyl 4-mercapto-2-methoxyphenoxyacetate (Intermediate 15) (1.6 g,7 mmol), 4,4'-biphenyidipropanol bismethanesulfonate (example 38)(1.48 g,3.5 mmol), potassium carbonate (1.38 g, 10 mmol) and 2-butanone (40 mL) was refluxed under stirring for 8 h. Water and ethyl acetate were added, organic phase was separated, dried ($K_2CO_3$) and evaporated. The residue was purified by chromatography on silica gel (25 g, ethyl acetate) and then recrystallized from diethyl ether yielding 1.60 g (66%) of the dimethyl ester of the title compound.

M.p.108.5-110.5° C.

$^1$H-NMR spectrum (DMSO): 7.51 (d, J=8.0 Hz, 4 H); 7.22 (d, J=8.0 Hz, 4 H); 6.93 (s, 2 H); 6.82 (m, 4 H); 4.73 (s, 4 H); 3.73 (s, 6 H); 3.66 (s, 6 H); 2.88 (t, 4 H); 2.70 (t, 4 H); 1.82 (m, 4 H).

General Procedure D:

Step A:

The above dimethyl ester (1.52 g, 2.2 mmol) was dissolved in the mixture of ethanol (25 mL) and tetrahydrofuran (25 mL) under reflux, 20% solution of sodium hydroxide (3 mL)) was added and the mixture was left to stand at laboratory temperature for 48 h. The solvents were evaporated, water was added to the residue and the product was precipitated with HCl. The solid was filtered with suction, washed with water and dried yielding 1.45 g (95%) of the title compound as sesquihydrate.

M.p. 178-180° C.

R$_F$(free acid, SiO$_2$, ethyl acetate) 0.50.

$^1$H NMR spectrum (300 MHz, DMSO-d$_6$): 13.0 (bs, 2 H); 7.51 (d, J=8.2 Hz, 4 H); 7.22 (d, J=8.2 Hz, 4 H); 6.93 (d, J=1.8 Hz, 2 H); 6.85 (dd, J=1.8 and 8.4 Hz, 2 H); 6.78 (d, J=8.4 Hz, 2 H); 4.60 (s, 4 H); 3.73 (s, 6 H); 2.88 (t, J=7.3 Hz, 4 H); 2.70 (t, J=7.3 Hz, 4 H); 1.81 (p, 4 H).

Example 42

General Procedure B

{4-[3-(4-{4-[3-(4-Carboxymethoxy-3-trifluorom-ethyl-phenylsulfanyl)-propyl]-2-trifluoromethyl-phenylsulfanyl}-3-trifluoromethyl-phenyl)-propyl-sulfanyl]-2-trifluoromethyl-phenoxy}-acetic acid

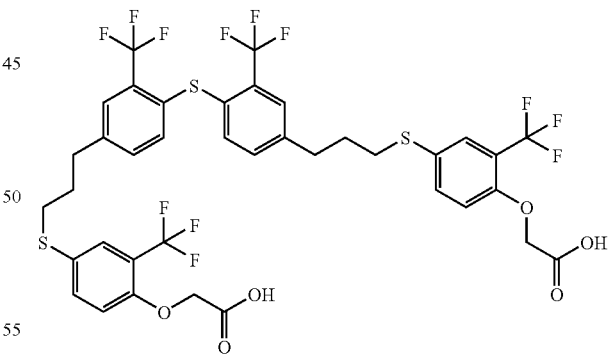

Step A:

To the solution of 3-{4-[4-(3-hydroxy-propyl)-2-trifluoromethyl-phenylsulfanyl]-3-trifluoromethyl-phenyl}-propan-1-ol (intermediate 16) (4.0 g, 9.1 mmol) and triethylamine (2.5 g, 24.7 mmol) in dichloromethane (50 mL) methanesulfonyl chloride (2.5 g, 21.8 mmol) was added dropwise. The mixture was stirred overnight at room temperature, then washed with water and dichloromethane was evaporated. This afforded 5.4 g (99.5%) of methanesulfonic acid 3-{4-[4-(3-methanesulfonyloxy-propyl)-2-trifluoromethyl-phenylsulfanyl]-3-trifluoromethyl-phenyl}-propyl ester as an oil.

$^1$H NMR spectrum (300 MHz, CDCl$_3$): 7.54 (s, 2 H); 7.25 (dd, J=1.1 and 7.15 Hz, 2 H); 7.14 (d, J=8.0 Hz, 2 H); 4.23 (t, J=6.2 Hz, 4 H); 3.00 (s, 6 H); 2.79 (t, J=7.0 Hz, 4 H); 2.07 (m, 4 H).

Step B:

The 4,4'-dithiobis-(2-trifluoromethylphenoxyacetic acid diethyl ester) (intermediate 11) (2.6 g, 4.65 mmol) was dissolved in 15 mL dimethylacetamide, sodium borohydride (0.4 g, 10.6 mmol) was added portionwise at 5° C. and the mixture was stirred for 30 min. The solution of above bis-methanesulfonate (2.3 g, 3.87 mmol) in acetone (30 mL) and potassium carbonate (1.4 9, 10 mmol) were added and the mixture was stirred overnight at ambient temperature and then refluxed for 7 h. Water and benzene were added, the organic layer was dried (K$_2$CO$_3$), filtered and evaporated to give a residue which was purified by chromatography on silica gel (100 g, benzene). This afforded 3.1 g (85%) of diethyl ester of the title compound.

$^1$H NMR spectrum (300 MHz, CDCl$_3$): 7.59 (d, 2H, J=2.2); 7.50 (d, 2H, J=1.5); 7.45 (dd, 2H, J=2.2;8.5); 7.19 (dd, 2H, J=1.5;8.0); 7.11 (d, 2H, J=8.0); 6.80 (d, 2H, J=8.5); 4.70 (S, 4H); 4.25 (q, 4H, J=7.15); 2.84 (t, 4H, J=7.15); 2.76 (t, 4H, J=7.15); 1.89 (pent, 4H); 1.27 (t, 6H, J=7.15)

General Procedure D:

Step A:

The above diethyl ester (3.0 g, 3.3 mmol) was dissolved in 100 mL ethanol, 20% NaOH (5 mL) was added and the mixture was refluxed for 5 h. The solvent was evaporated, the residue dissolved in water and the product precipitated with conc. hydrochloric acid and extracted with chloroform. The organic layer was dried (MgSO$_4$), filtered and evaporated affording a residue which was purified by chromatography on silica gel (30 g, chloroform/ethanol 95:5). The yield of the title compound was 1.82g (61%).

M.p. 58-64° C.

R$_F$ (SiO$_2$, ethyl acetate): 0.62

$^1$H NMR spectrum (300 MHz, DMSO-d$_6$): 7.60 (d, J=2.2 Hz, 2 H); 7.50 (d, J=1.6 Hz, 2 H); 7.43 (dd, J=8.5 and 2.2 Hz, 2 H); 7.17 (dd, J=8.0 and 1.6 Hz, 2 H); 7.11 (d, J=8.0 Hz, 2 H); 6.81 (d, J=8.5 Hz, 2 H); 4.76 (s, 4 H); 2.85 (t, J=7.15 Hz, 4 H); 2.76 (t, J=7.15 Hz, 4 H); 1.89 (m, 4 H).

Using a combination of the above methods, or methods analogous hereof, various compounds may be made within the scope of the present invention.

Pharmacological Methods

In vitro PPARalpha, PPARgamma and PPARdelta Activation Activity

The PPAR transient transactivation assays are based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seededin 96-well plates the day before transfection to give a confluency of 50-80% at transfection. A total of 0,8 μg DNA containing 0,64 μg pM1α/γLBD, 0,1 μg pCMVβGal, 0,08 μg pGL2(Gal4)$_5$ and 0,02 μg pADVANTAGE was transfected per well using FuGene transfection reagent according to the manufacturers instructions (Roche). Cells were allowed to express protein for 48 h followed by addition of compound.

Plasmids: Human PPAR α, γ and δ was obtained by PCR amplification using cDNA synthesized by reverse transcription of mRNA from human liver, adipose tissue and plancenta respectively. Amplified cDNAs were cloned into pCR2.1 and sequenced. The ligand binding domain (LBD) of each PPAR isoform was generated by PCR (PPARα: aa 167-C-terminus; PPARγ: aa 165-C-terminus; PPARδ: aa 128-C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5× CGGAG-TACTGTCCTCCG(AG)) (Webster et al. (1988), Nucleic Acids Res. 16, 8192) into the vector pGL2 promotor (Promega) generating the plasmid pGL2(GAL4)$_5$. pCMVβ-Gal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 μM. Cells were treated with compound for 24 h followed by luciferase assay. Each compound was tested in at least two separate experiments.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting on a Packard LumiCounter. To measure β-galactosidase activity 25 μl supernatant from each transfection lysate was transferred to a new microplate. 0-galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as means±SD.

The invention claimed is:
1. A compound selected from the group consisting of:
- (S,S)-2-Ethoxy-3-{4-[3-(4'-{3-[4-(2-ethoxy-2-isopropoxycarbonyl-ethyl)-phenoxy]-propyl}-2,2'-bis-trifluoromethyl-biphenyl-4-yl)-propoxy]-phenyl}-propionic acid;
- (S,S)-3-{4-[3-(4'-{3-[4-(2-Carboxy-2-ethoxy-ethyl)-phenoxy]-propyl}-2,2'-bis -trifluoromethyl-biphenyl-4-yl)-propoxy]-phenyl}-2-ethoxy-propionic acid;
- (S,S)-2-Ethoxy-3-{4-[3-(4'-{3-[4-(2-ethoxy-2-isopropoxycarbonyl-ethyl)-phenoxy]-propyl}-3,3'-bis-trifluoromethyl-biphenyl-4-yl)-propoxy]-phenyl}-propionic acid;
- (S,S)-3-{4-[3-(4'-{3-[4-(2-Carboxy-2-ethoxy-ethyl)-phenoxy]-propyl}-3,3'-bis -trifluoromethyl-biphenyl-4-yl)-propoxy]-phenyl}-2-ethoxy-propionic acid;
- (S,S)-3-{3-Bromo-4-[3-(4'-{3-[2-bromo-4-(2-ethoxy-2-isopropoxycarbonyl-ethyl) -phenoxy]-propyl}-2,2'-bis-trifluoromethyl-biphenyl-4-yl)-propoxy]-phenyl}-2-ethoxy -propionic acid;
- (S,S) -3-{3-Bromo-4-[3-(4'-{3-[2-bromo-4-(2-carboxy-2-ethoxy-ethyl)-phenoxy]-propyl}-2,2'-bis-trifluoromethyl-biphenyl-4-yl)-propoxy]-phenyl}-2-ethoxy-propionic acid;
- (S,S)-3-{3-Bromo-4-[3-(4'-{3-[2-bromo-4-(2-ethoxy-2-isopropoxycarbonyl-ethyl)-phenoxy]-propyl}-3,3'-bis-trifluoromethyl-biphenyl-4-yl)-propoxy]-phenyl}-2-ethoxy -propionic acid;
- (S,S)-3-{3-Bromo-4-[3-(4'-{3-[2-bromo-4-(2-carboxy-2-ethoxy-ethyl)-phenoxy]-propyl}-3,3'-bis-trifluoromethyl-biphenyl-4-yl)-propoxy]-phenyl}-2-ethoxy-propionic acid;
- [4-(3-{4'-[3-(4-Methoxycarbonylmethoxy-3-methyl-phenylsulfanyl)-propyl]-2 ,2'-bis -trifluoromethyl-biphenyl-4-yl}-propylsulfanyl)-2-methyl-phenoxy]-acetic acid;
- [4-(3-{4'-[3-(4-Methoxycarbonylmethoxy-3-methyl-phenylsulfanyl)-propyl]-3,3'-bis -trifluoromethyl-biphenyl-4-yl}-propylsulfanyl)-2-methyl-phenoxy]-acetic acid;
- [4-(3-{4'-[3-(4-Carboxymethoxy-3-methyl-phenylsulfanyl)-propyl]-3,3'-bis -trifluoromethyl-biphenyl-4-yl}-propylsulfanyl)-2-methyl-phenoxy]-acetic acid;
- (4-{2-[2-(3-{4-[2-(4-Methoxycarbonyl methoxy-3-methyl-phenylsulfanyl)-ethyl]-5-methyl-oxazol-2-yl}-phenyl)-5-methyl-oxazol-4-yl]-ethylsulfanyl}-2-methyl-phenoxy) -acetic acid;
- (4-{2-[2-(3-{4-[2-(4-Carboxymethoxy-3-methyl -phenyl-sulfanyl)-ethyl]-5-methyl -oxazol-2-yl}-phenyl)-5-methyl-oxazol-4-yl]-ethylsulfanyl}-2-methyl-phenoxy)-acetic acid;
- (S,S)-2-Ethoxy-3-[4-(2-{2-[4'-(4-{2-[4-(2-ethoxy-2-isopropoxycarbonyl-ethyl) -phenoxy]-ethyl}-5-methyl-oxazol-2-yl)-biphenyl-4-yl]-5-methyl-oxazol-4-yl}-ethoxy)-phenyl]-propionic acid;
- (S,S)-3-[4-(2-{2-[4'-(4-{2-[4-(2-Carboxy-2-ethoxy-ethyl)-phenoxy]-ethyl}-5-methyl-oxazol-2-yl)-biphenyl-4-yl]-5-methyl-oxazol-4-yl}-ethoxy)-phenyl]-2-ethoxy -propionic acid;
- (S,S)-2-Ethoxy-3-[4-(2-{2-[3-(4-{2-[4-(2-ethoxy-2-isopropoxycarbonyl-ethyl)-phenoxy]-ethyl}-5-methyl-oxazol-2-yl)-phenyl]-5-methyl -oxazol-4-yl}-ethoxy) -phenyl]-propionic acid; and
- (S,S)- 3-[4-(2-{2-[3-(4-{2-[4-(2-Carboxy-2-ethoxy-ethyl)-phenoxy]-ethyl}-5-methyl-oxazol-2-yl)-phenyl]-5-methyl-oxazol-4-yl}-ethoxy)-phenyl]-2-ethoxy-propionic acid; or
- a salt thereof with a pharmaceutically acceptable acid or base, or any optical isomer or mixture of optical isomers, racemic mixture, or any tautomeric forms.

2. A compound which is selected from the group consisting of:
- (S,S)-2-Ethoxy-3-{4-[3-(4'-{3-[4-(2-ethoxy-2-isopropoxycarbonyl-ethyl)-phenoxy]-propyl}-2,2'-bis-trifluoromethyl-biphenyl-4-yl)-propoxy]-phenyl}-propionic acid isopropyl ester;
- (S,S)-2-Ethoxy-3-{4-[3-(4'-{3-[4-(2-ethoxy-2-isopropoxycarbonyl-ethyl)-phenoxy]-propyl}-3,3'-bis-trifluoromethyl-biphenyl-4-yl)-propoxy]-phenyl}-propionic acid isopropyl ester;
- (S,S)-3-{3-Bromo-4-[3-(4'-{3-[2-bromo-4-(2-ethoxy-2-isopropoxycarbonyl-ethyl)-phenoxy]-propyl}-2,2'-bis-trifluoromethyl-biphenyl-4-yl)-propoxy]-phenyl}-2-ethoxy-propionic acid isopropyl ester;
- (S,S)-3-{3-Bromo-4-[3-(4'-{3-[2-bromo-4-(2-ethoxy-2-isopropoxycarbonyl-ethyl)-phenoxy]-propyl}-3,3'-bis-trifluoromethyl-biphenyl-4-yl)-propoxy]-phenyl}-2-ethoxy-propionic acid isopropyl ester;
- [4-(3-{4'-[3-(4-Methoxycarbonylmethoxy-3-methyl-phenylsulfanyl)-propyl]-2,2'-bis-trifluoromethyl-biphenyl-4-yl}-propylsulfanyl)-2-methyl-phenoxy]-acetic acid methyl ester;
- [4-(3-{4'-[3-(4-Carboxymethoxy-3-methyl-phenylsulfanyl)-propyl]-2,2'-bis-trifluoromethyl-biphenyl-4-yl}-propylsulfanyl)-2-methyl-phenoxy]-acetic acid;
- [4-(3-{4'-[3-(4-Methoxycarbonylmethoxy-3-methyl-phenylsulfanyl)-propyl]-3,3'-bis-trifluoromethyl-biphenyl-4-yl}-propylsulfanyl)-2-methyl-phenoxy]-acetic acid methyl ester;
- (4-{2-[2-(3-{4-[2-(4-Methoxycarbonyl methoxy-3-methyl-phenylsulfanyl)-ethyl]-5-methyl-oxazol-2-yl}-phenyl)-5-methyl-oxazol-4-yl]-ethylsulfanyl}-2-methyl-phenoxy)-acetic acid methyl ester;
- (S,S)-2-Ethoxy-3-[4-(2-{2-[4'-(4-{2-[4-(2-ethoxy-2-isopropoxycarbonyl-ethyl)-phenoxy]-ethyl}-5-methyl-oxazol-2-yl)-biphenyl-4-yl]-5-methyl-oxazol-4-yl}-ethoxy)-phenyl]-propionic acid isopropyl ester; and
- (S,S)-2-Ethoxy-3-[4-(2-{2-[3-(4-{2-[4-(2-ethoxy-2-isopropoxycarbonyl-ethyl)-phenoxy]-ethyl}-5-methyl-oxazol-2-yl)-phenyl]-5-methyl -oxazol-4-yl}-ethoxy)-phenyl]-propionic acid isopropyl ester; or
- a salt thereof with a pharmaceutically acceptable acid or base, or any optical isomer or mixture of optical isomers, racemic mixture, or any tautomeric forms.

3. A compound which is selected from the group consisting of:
- 3-[4-(2-{2-[3-(4-{2-[4-(2-Carboxy-2-ethoxy-ethyl)-phenoxy]-ethyl}-5-methyl-oxazol-2-yl)-phenyl]-5-methyl-oxazol-4-yl}-ethoxy)-phenyl]-2-ethoxy-propionic acid;
- (4-{2-[2-(3-{4-[2-(4-Carboxymethoxy-3-methyl -phenylsulfanyl)-ethyl]-5-methyl-oxazol-2-yl}-phenyl)-5-methyl-oxazol-4-yl]-ethylsulfanyl}-2-methyl-phenoxy)-acetic acid;
- (4-{2-[2-(3-{4-[2-(4-Carboxymethoxy-3-methyl-phenoxy)-ethyl]-5-methyl-oxazol-2-yl}-phenyl)-5-methyl-oxazol-4-yl]-ethoxy}-2-methyl-phenoxy)-acetic acid;
- (4-{2-[2-(3-{4-[2-(4-Carboxymethoxy -phenoxy)-ethyl]-5-methyl-oxazol-2-yl}-phenyl)-5-methyl-oxazol-4-yl]-ethoxy}-phenoxy)-acetic acid;

(4-{2-[2-(3-{4-[2-(4-Carboxymethoxy -phenylsulfanyl)-ethyl]-5-methyl-oxazol-2-yl}-phenyl)-5-methyl-oxazol-4-yl]-ethylsulfanyl}-phenoxy)-acetic acid;

3-[4-(2-{2-[3-(4-{2-[4-(2-Carboxy-2-ethoxy-ethyl)-phensulfanyl]-ethyl}-5-methyl-oxazol-2-yl)-phenyl]-5-methyl-oxazol-4-yl}-ethylsulfanyl)-phenyl]-2-ethoxy-propionic acid;

3-{4-[3-(4'-{3-[4-(2-Carboxy-2-ethoxy-ethyl)-phenoxy]-propyl}-2 ,2'-bis-trifluoromethyl-biphenyl-4-yl)-propoxy]-phenyl}-2-ethoxy-propionic acid; 3-{4-[3-(4'-{3-[4-(2-Carboxy-2-ethoxy-ethyl )-phenoxy]-propyl}-3,3'-bis-trifluoromethyl-biphenyl-4-yl)-propoxy]-phenyl}-2-ethoxy-propionic acid; 3-{3-Bromo-4-[3-(4'-{3-[2-bromo-4-(2-carboxy-2-ethoxy-ethyl)-phenoxy]-propyl}-2,2'-bis-trifluoromethyl-biphenyl-4-yl)-propoxy]-phenyl}-2-ethoxy -propionic acid;

3-{3-Bromo-4-[3-(4'-{3-[2-bromo-4-(2-carboxy-2-ethoxy-ethyl)-phenoxy]-propyl}-3,3'-bis-trifluoromethyl-biphenyl-4-yl)-propoxy]-phenyl}-2-ethoxy -propionic acid;

[4-(3-{4'-[3-(4-Carboxymethoxy-3-methyl -phenylsulfanyl)-propyl]-3,3'-bis-trifluoromethyl-biphenyl-4-yl}-propylsulfanyl)-2-methyl-phenoxy]-acetic acid; [4-(3-{4'-[3-(4-Carboxymethoxy-phenylsulfanyl)-propyl]-3,3'-bis-trifluoromethyl-biphenyl-4-yl}-propylsulfanyl)-phenoxy]-acetic acid; [4-(3-{4'-[3-(4-Carboxymethoxy-phenoxy)-propyl]-3,3'-bis-trifluoromethyl-biphenyl-4-yl}-propoxy)-phenoxy]-acetic acid;

[4-(3-{4'-[3-(4-Carboxymethoxy-3-methyl -phenoxy)-propyl]-3,3'-bis-trifluoromethyl-biphenyl-4-yl}-propoxy)-2-methyl-phenoxy]-acetic acid;

[4-(3-{4'-[3-(4-Carboxymethoxy-3-methyl -phenylsulfanyl)-propyl]-2,2'-bis-trifluoromethyl-biphenyl-4-yl}-propylsulfanyl)-2-methyl-phenoxy]-acetic acid;

[4-(3-{4'-[3-(4-Carboxymethoxy-3-methyl -phenoxy)-propyl]-2 ,2'-bis-trifluoromethyl-biphenyl-4-yl}-propoxy)-2-methyl-phenoxy]-acetic acid; and 3-[4-(2-{2-[4'-(4-{2-[4-(2-Carboxy-2-ethoxy-ethyl)-phenoxy]-ethyl}-5-methyl-oxazol-2-yl)-biphenyl-4-yl]-5-methyl-oxazol-4-yl}-ethoxy)-phenyl]-2-ethoxy-propionic acid; or a salt thereof with a pharmaceutically acceptable acid or base, or any optical isomer or mixture of optical isomers, racemic mixture, or any tautomeric forms.

4. A pharmaceutical composition comprising, as an active ingredient, at least one compound according to claim 1 together with one or more pharmaceutically acceptable carriers or excipients.

5. A pharmaceutical composition according to claim 4 in unit dosage form, comprising from about 0.05 mg to about 1000 mg of compound.

6. A pharmaceutical composition according to claim 4 formulated for oral, nasal, transdermal, pulmonal, or parenteral administration.

7. A pharmaceutical composition comprising, as an active ingredient, at least one compound according to claim 2 together with one or more pharmaceutically acceptable carriers or excipients.

8. A pharmaceutical composition according to claim 7 in unit dosage form, comprising from about 0.05 mg to about 1000 mg of compound.

9. A pharmaceutical composition comprising, as an active ingredient, at least one compound according to claim 3 together with one or more pharmaceutically acceptable carriers or excipients.

10. A pharmaceutical composition according to claim 9 in unit dosage form, comprising from about 0.05 mg to about 1000 mg of compound.

* * * * *